(12) United States Patent
Pilarski et al.

(10) Patent No.: US 8,329,696 B2
(45) Date of Patent: Dec. 11, 2012

(54) SOLID STATE FORMS OF SITAGLIPTIN SALTS

(75) Inventors: Gideon Pilarski, Holon (IL); Nurit Perlman, Kfar Saba (IL); Ariel Mittelman, Elad (IL); Nada Kosutic Hulita, Zagreb (HR); Marina Kalujny, Ariel (IL); Revital Ramaty, Ramat-Hasharon (IL)

(73) Assignee: Teva Pharmaceuticals Industries Ltd., Petach-Tikva (IL)

( * ) Notice: Subject to any disclaimer, the term of this patent is extended or adjusted under 35 U.S.C. 154(b) by 144 days.

(21) Appl. No.: 12/749,486

(22) Filed: Mar. 29, 2010

(65) Prior Publication Data

US 2010/0249140 A1   Sep. 30, 2010

Related U.S. Application Data

(60) Provisional application No. 61/164,563, filed on Mar. 30, 2009, provisional application No. 61/170,697, filed on Apr. 20, 2009, provisional application No. 61/174,073, filed on Apr. 30, 2009, provisional application No. 61/182,772, filed on Jun. 1, 2009, provisional application No. 61/186,031, filed on Jun. 11, 2009, provisional application No. 61/302,626, filed on Feb. 9, 2010, provisional application No. 61/304,615, filed on Feb. 15, 2010, provisional application No. 61/309,024, filed on Mar. 1, 2010, provisional application No. 61/312,376, filed on Mar. 10, 2010, provisional application No. 61/315,149, filed on Mar. 18, 2010.

(51) Int. Cl.
*A61K 31/495* (2006.01)
(52) U.S. Cl. ......................... 514/249; 544/350
(58) Field of Classification Search ................... 514/249; 544/350
See application file for complete search history.

(56) References Cited

FOREIGN PATENT DOCUMENTS

| WO | WO 2004/085378 | 10/2004 |
|----|---------------|---------|
| WO | WO 2004/085661 | 10/2004 |
| WO | WO 2004/087650 | 10/2004 |
| WO | WO 2005/003135 | 1/2005 |
| WO | WO 2005/020920 | 3/2005 |
| WO | WO 2005/030127 | 4/2005 |
| WO | WO 2005/072530 | 8/2005 |
| WO | WO 2006/033848 | 3/2006 |
| WO | WO 2007/035198 | 3/2007 |
| WO | WO 2009/070314 | 6/2009 |
| WO | WO2009/085990 | 7/2009 |
| WO | WO2010/000469 | 1/2010 |
| WO | WO2010/012781 | 2/2010 |

*Primary Examiner* — Douglas M Willis
(74) *Attorney, Agent, or Firm* — Arent Fox LLP

(57) ABSTRACT

Solid state forms of Sitagliptin salts (e.g. Sitagliptin sulfate, Formula I), processes for preparing the solid state forms, and pharmaceutical compositions thereof, are provided. These compounds are of a class of dipeptidyl peptidase IV enzyme inhibitors which are useful, for example, for the manufacture of a medicament for the treatment of type 2 diabetes mellitus.

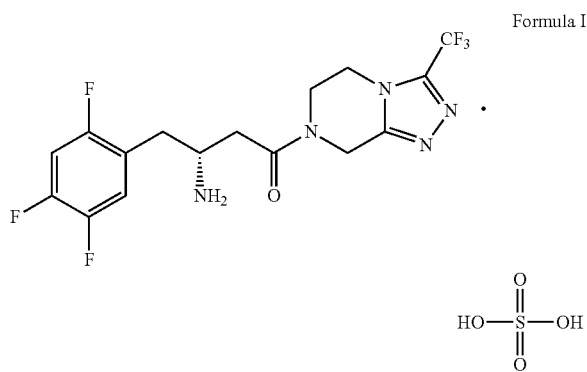

Formula I

10 Claims, 70 Drawing Sheets

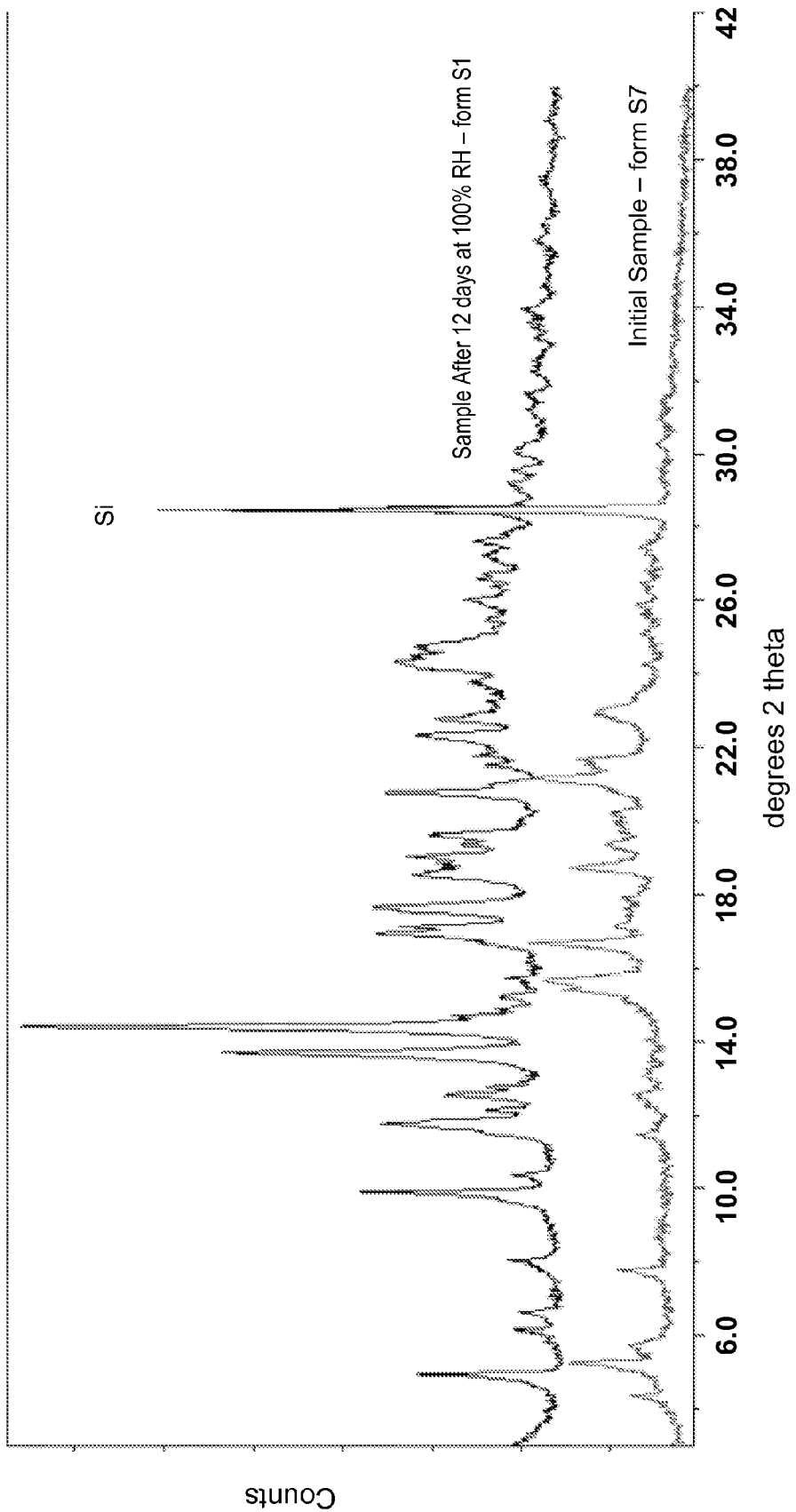

SOLID STATE FORMS OF SITAGLIPTIN SALTS

CROSS-REFERENCE TO RELATED APPLICATIONS

This application claims the benefit of U.S. Provisional Patent Application Ser. Nos. 61/164,563, filed Mar. 30, 2009; 61/170,697, filed Apr. 20, 2009; 61/174,073, filed Apr. 30, 2009; 61/182,772, filed Jun. 1, 2009; 61/186,031, filed Jun. 11, 2009; 61/302,626, filed Feb. 9, 2010; 61/304,615, filed Feb. 15, 2010; 61/309,024, filed Mar. 1, 2010; 61/312,376, filed Mar. 10, 2010; and 61/315,149, filed Mar. 18, 2010, which are incorporated herein by reference.

FIELD OF THE INVENTION

The invention relates to crystalline and amorphous forms of Sitagliptin salts, processes for preparing the crystalline forms, and pharmaceutical compositions thereof.

BACKGROUND OF THE INVENTION

Sitagliptin, (3R)-3-amino-1-[9-(trifluoromethyl)-1,4,7,8-tetrazabicyclo-[4.3.0]nona-6,8-dien-4-yl]-4-(2,4,5-trifluorophenyl)butan-1-one, has the following chemical structure:

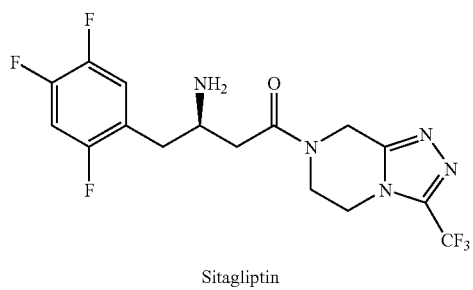

Sitagliptin

Sitagliptin phosphate is a glucagon-like peptide 1 metabolism modulator, hypoglycemic agent, and dipeptidyl peptidase IV inhibitor. Sitagliptin is currently marketed in the United States as its phosphate salt in its monohydrate form under the trade name JANUVIA™. JANUVIA™ is indicated to improve glycemic control in patients with type 2 diabetes mellitus.

The following PCT Publications describe the synthesis of Sitagliptin via stereoselective reduction: WO 2004/087650, WO 2004/085661, and WO 2004/085378.

Several crystalline forms of Sitagliptin phosphate are described in the literature. WO 2005/020920 describes crystalline forms I, II, III and an ethanol solvate; WO 2005/030127 describes crystalline form IV; WO 2005/003135 describes a monohydrate form, and WO 2006/033848 described the amorphous form.

Crystalline forms of Sitagliptin salts are described in PCT publications nos. WO2009/085990, WO2010/000469, and WO2010/012781.

Polymorphism, the occurrence of different crystal forms, is a property of some molecules and molecular complexes. A single molecule may give rise to a variety of polymorphs having distinct crystal structures and physical properties like melting point, thermal behaviours (e.g. measured by thermogravimetric analysis—"TGA", or differential scanning calorimetry—"DSC"), x-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Sitagliptin (or a salt thereof).

The present invention discloses solid state forms of Sitagliptin salts.

SUMMARY OF THE INVENTION

The present invention provides crystalline forms of Sitagliptin salts, and processes for preparing them.

The invention further provides a pharmaceutical formulation comprising the below described crystalline forms of Sitagliptin salts. This pharmaceutical composition may additionally comprise at least one pharmaceutically acceptable excipient.

The invention further provides the use of the solid state forms described below for the manufacture of a medicament for the treatment of type 2 diabetes mellitus.

BRIEF DESCRIPTION OF THE FIGURES

FIG. 1l shows a DSC thermogram of the heating process of Sitagliptin sulfate form S2 to obtain form S8.

FIG. 1q shows a transformation of Form S7 to S1 at 100% relative humidity. The peak at 28.5° is attributes to silicon powder.

FIG. 11l shows a solid state $^{13}$C NMR spectrum of Sitagliptin (S)-(+)-mandelate Form N2 in the 0-200 ppm range.

DETAILED DESCRIPTION OF THE INVENTION

The present application relates to new polymorphic forms of Sitagliptin salts. In some embodiments, the polymorphs of Sitagliptin salts of the invention are substantially free of any other polymorphic forms. By "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of any other polymorph. In other embodiments, the polymorphs of Sitagliptin salts of the invention contain from 1% to 20% (w/w), from 5% to 20% (w/w), or from 5% to 10% (w/w) of any other polymorph.

A crystal form may be referred to herein as being characterized by graphical data "as shown in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, the term "room temperature" refers to a temperature of about 20° C. to about 35° C., or about 25° C. to about 35° C., or about 25° C. to about 30° C., for example, about 25° C.

As used herein, the term "overnight" refers to a time interval from about 14 hours to about 24 hours, or about 14 hours to about 20 hours, for example, about 16 hours.

Unless indicated otherwise, the solid state forms of the present invention can be dried. Drying may be carried out, for example, at elevated temperature under reduced pressure. The crystalline form can be dried at a temperature from about 40° C. to about 60° C., or about 40° C. and about 50° C., for example, about 40° C. The drying can be carried out under reduced pressure (i.e., less than 1 atmosphere, for example, about 10 mbar to about 100 mbar, or about 10 mbar to about 25 mbar). The drying can take place over a period of about 8 hours to about 36 hours, or about 10 hours to about 24 hours, for example, about 16 hours. Drying can be carried out overnight.

Sitagliptin base, used in the present application, can be prepared, for example, by hydrogenating of (Z)-3-amino-1-(3-(trifluoromethyl)-5,6-dihydro-[1,2,4]triazolo[4,3-a]pyrazyn-7(8H)-yl)-4-(2,4,5-trifluorophenyl)but-2-en-1-one using a Rhodium-based catalyst, in the presence of a $C_1$-$C_4$ alcohol, for example, methanol, e.g. as indicated in Example 1 herein.

The present invention relates to crystalline forms of Sitagliptin sulfate, referred herein as Form S2, Form S6, and From S7.

Figure 1A:
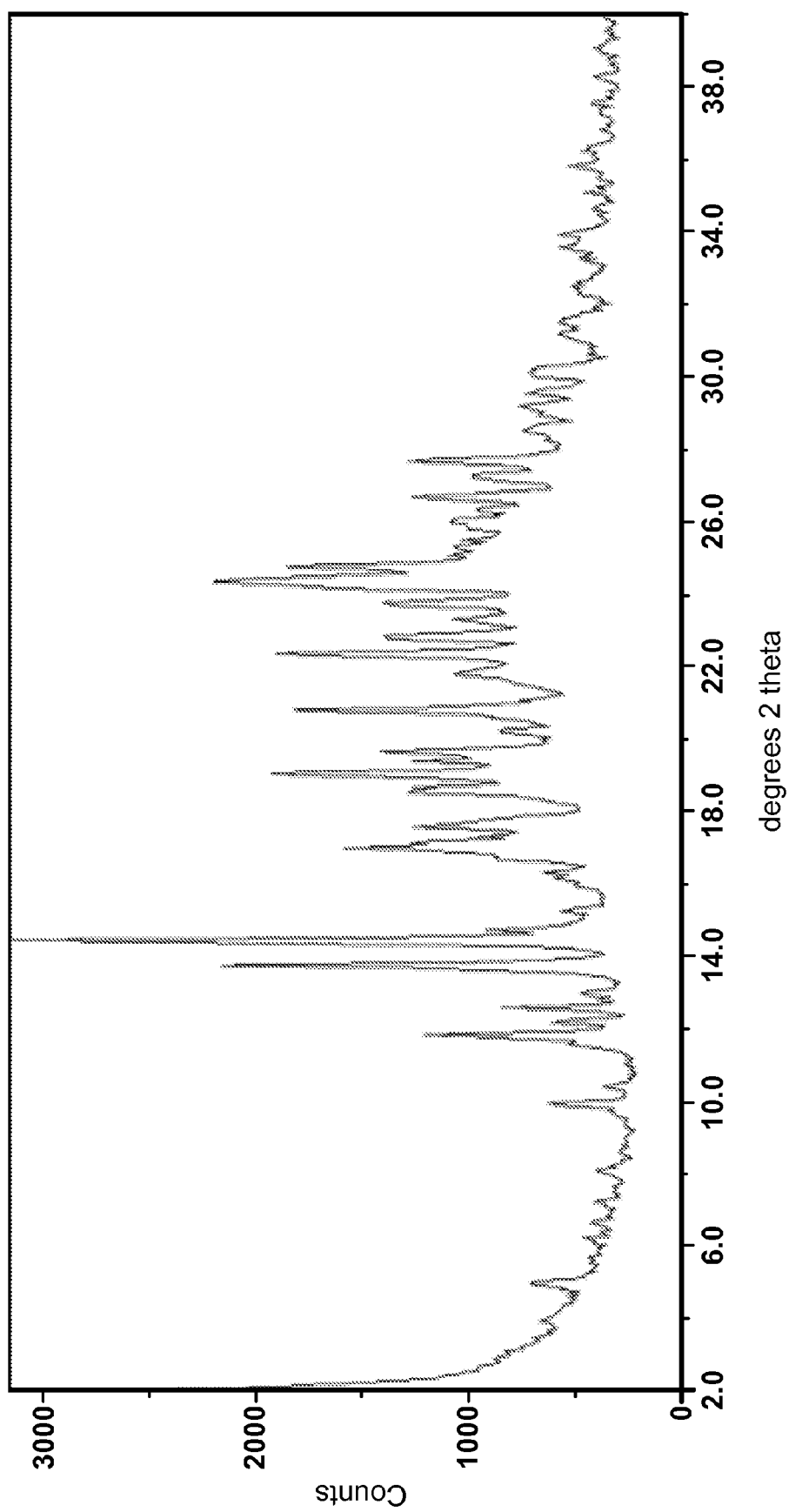
FIG. 1a shows a powder XRD pattern of crystalline Form S1 of Sitagliptin sulfate.
Figure 1B:
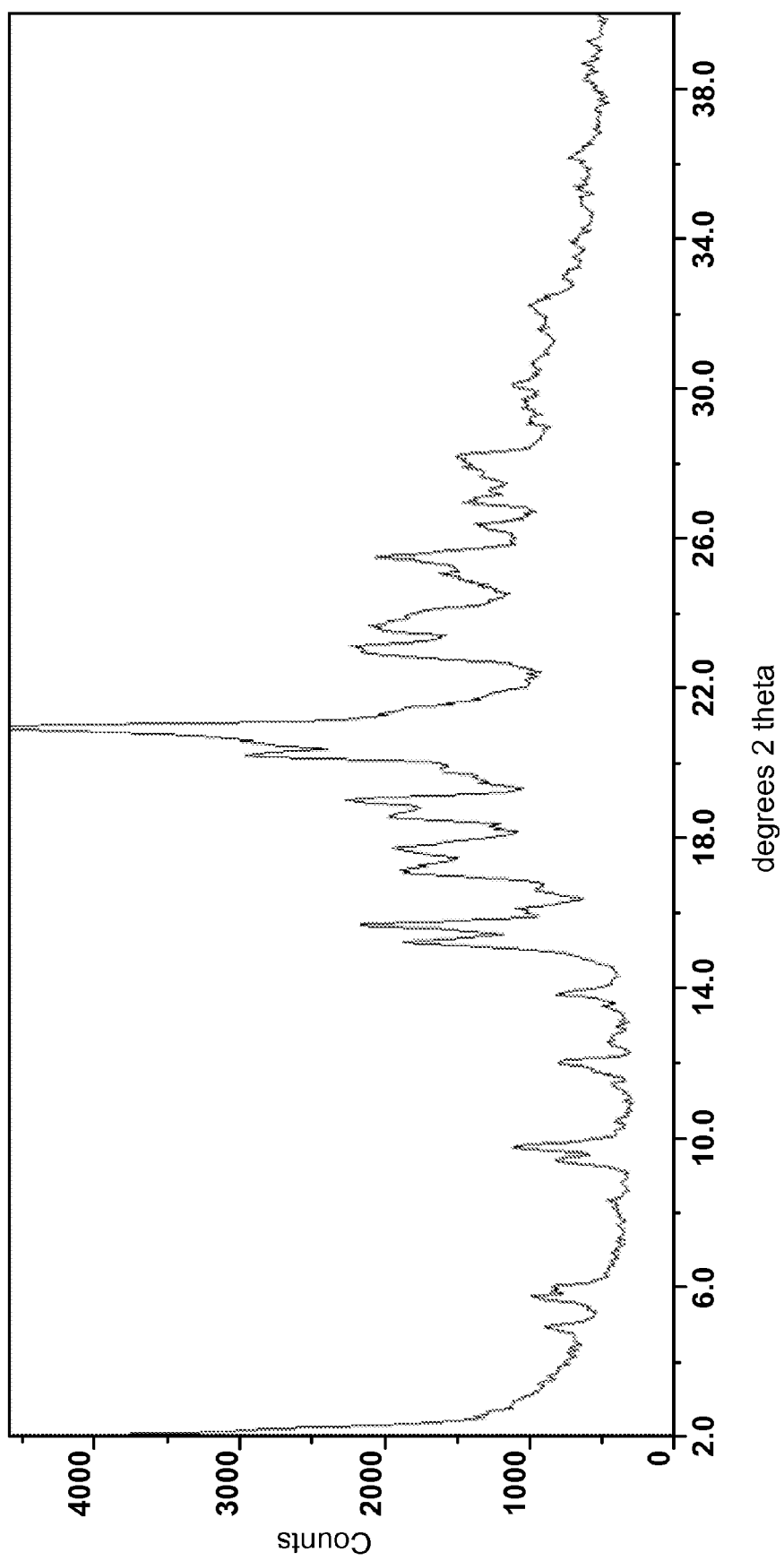
FIG. 1b shows a powder XRD pattern of crystalline Form S2 of Sitagliptin sulfate.
Figure 1C:
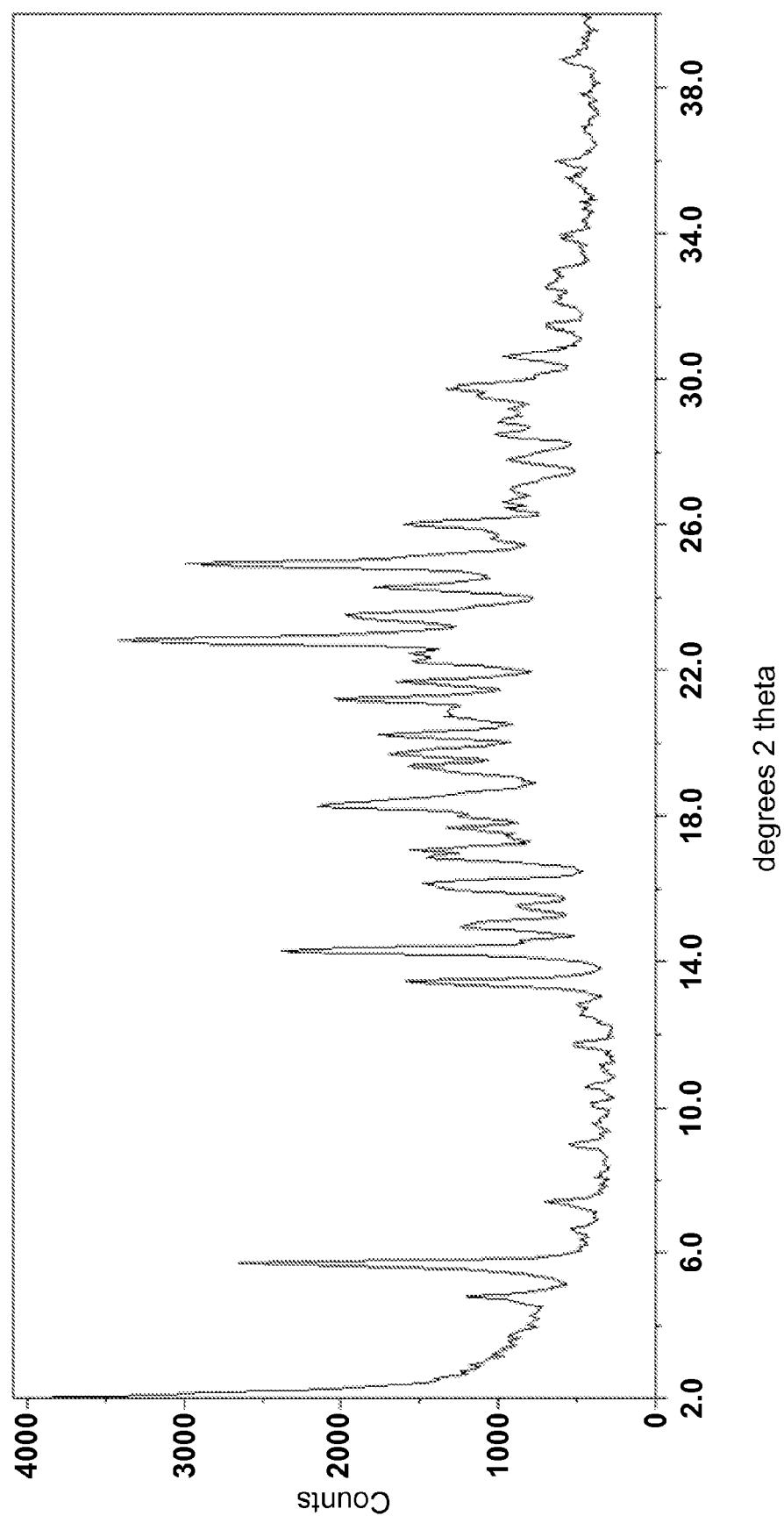
FIG. 1c shows a powder XRD pattern of crystalline Form S3 of Sitagliptin sulfate.
Figure 1D:
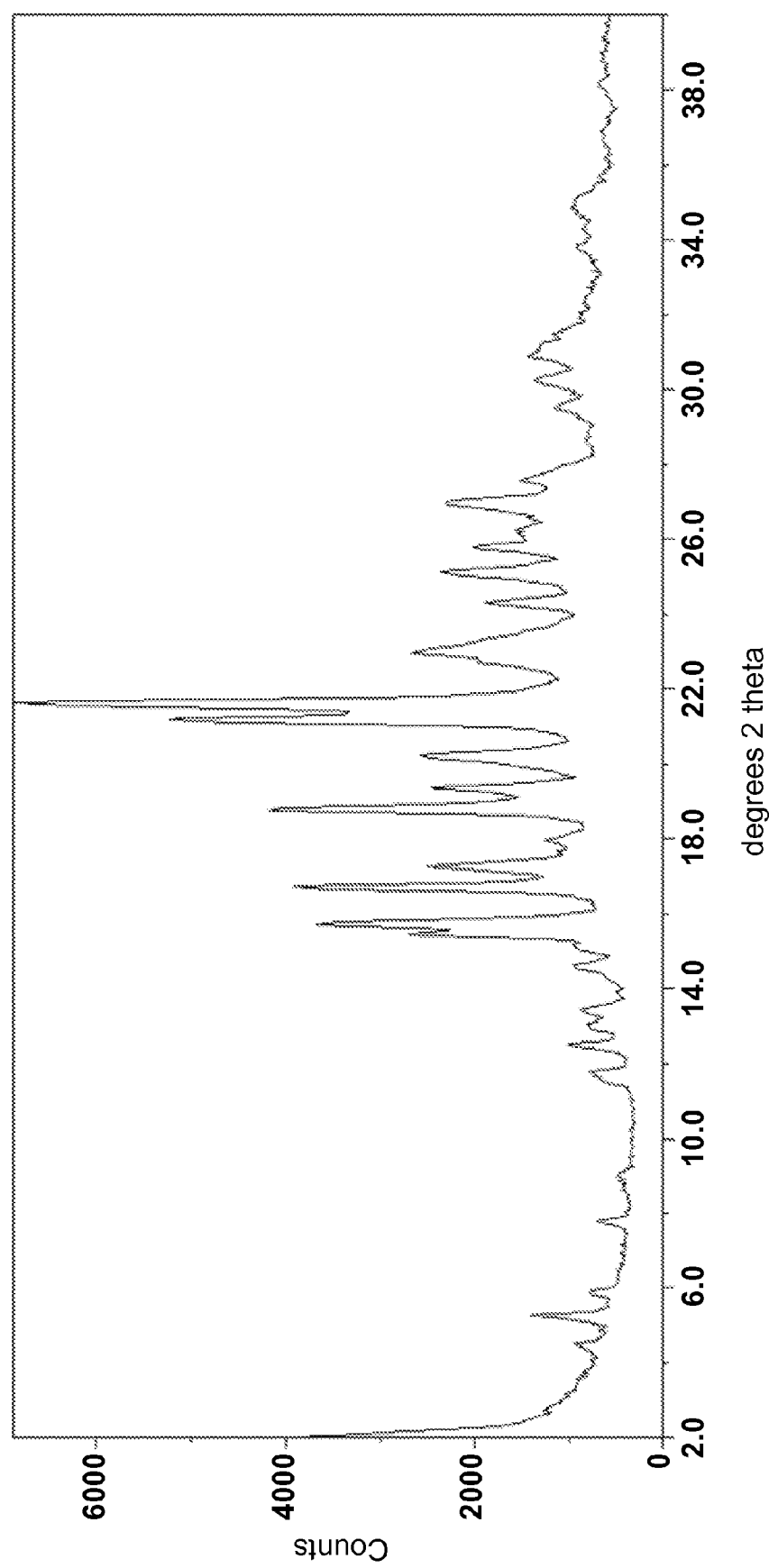
FIG. 1d shows a powder XRD pattern of crystalline Form S4 of Sitagliptin sulfate.
Figure 1E:
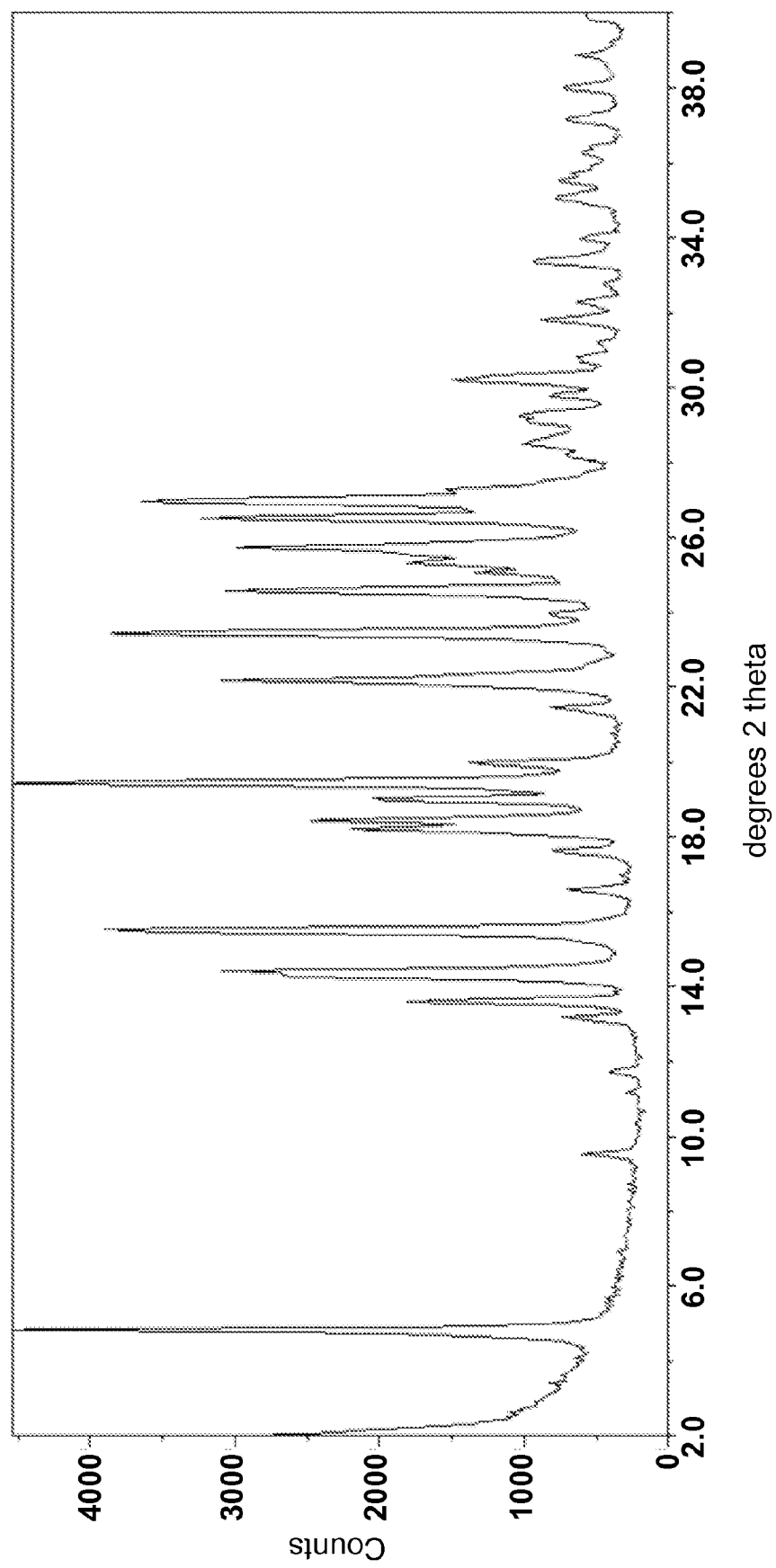
FIG. 1e shows a powder XRD pattern of crystalline Form S5 of Sitagliptin sulfate.
Figure 1F:
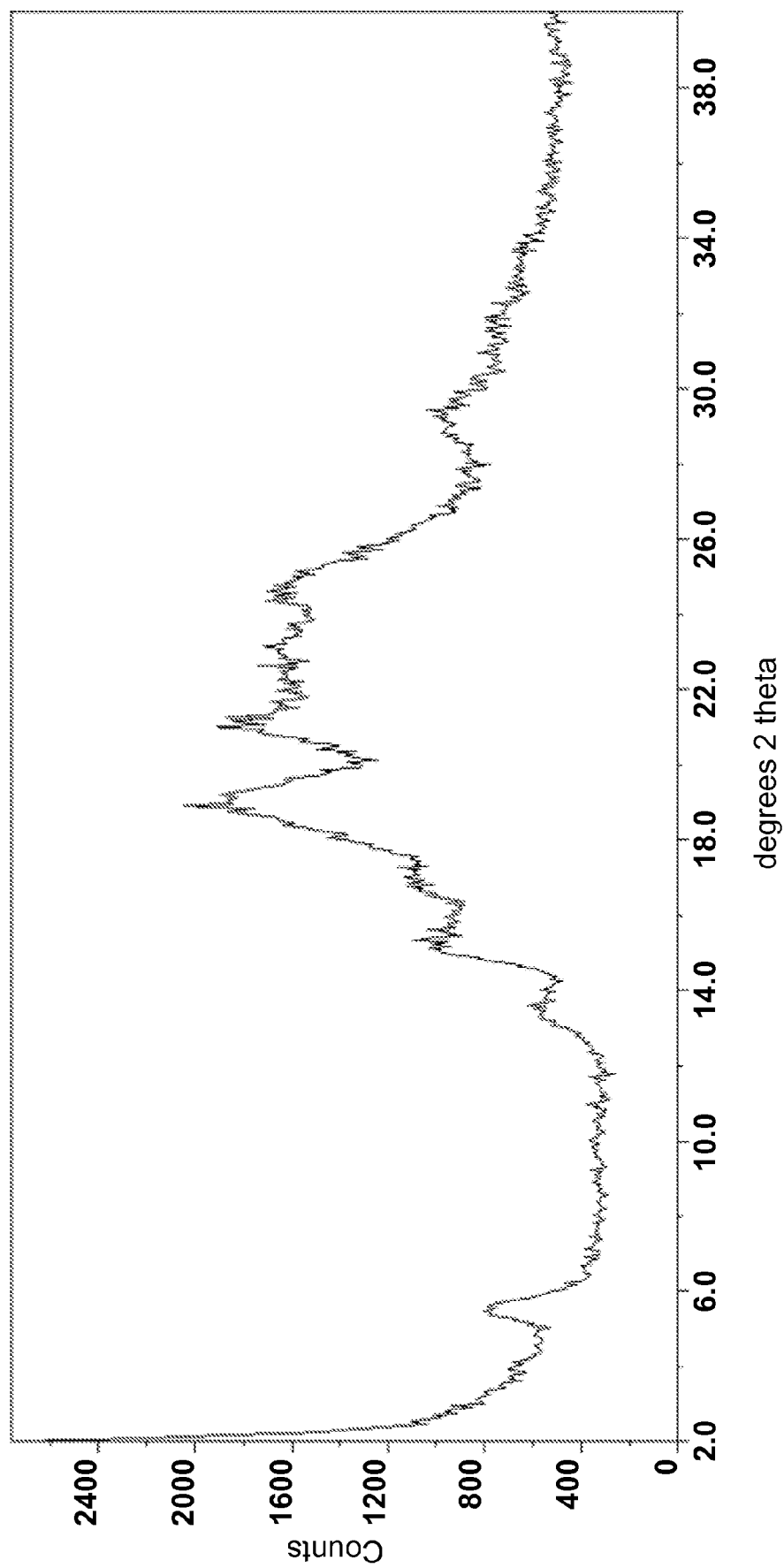
FIG. 1f shows a powder XRD pattern of crystalline Form S6 of Sitagliptin sulfate.
Figure 1G:
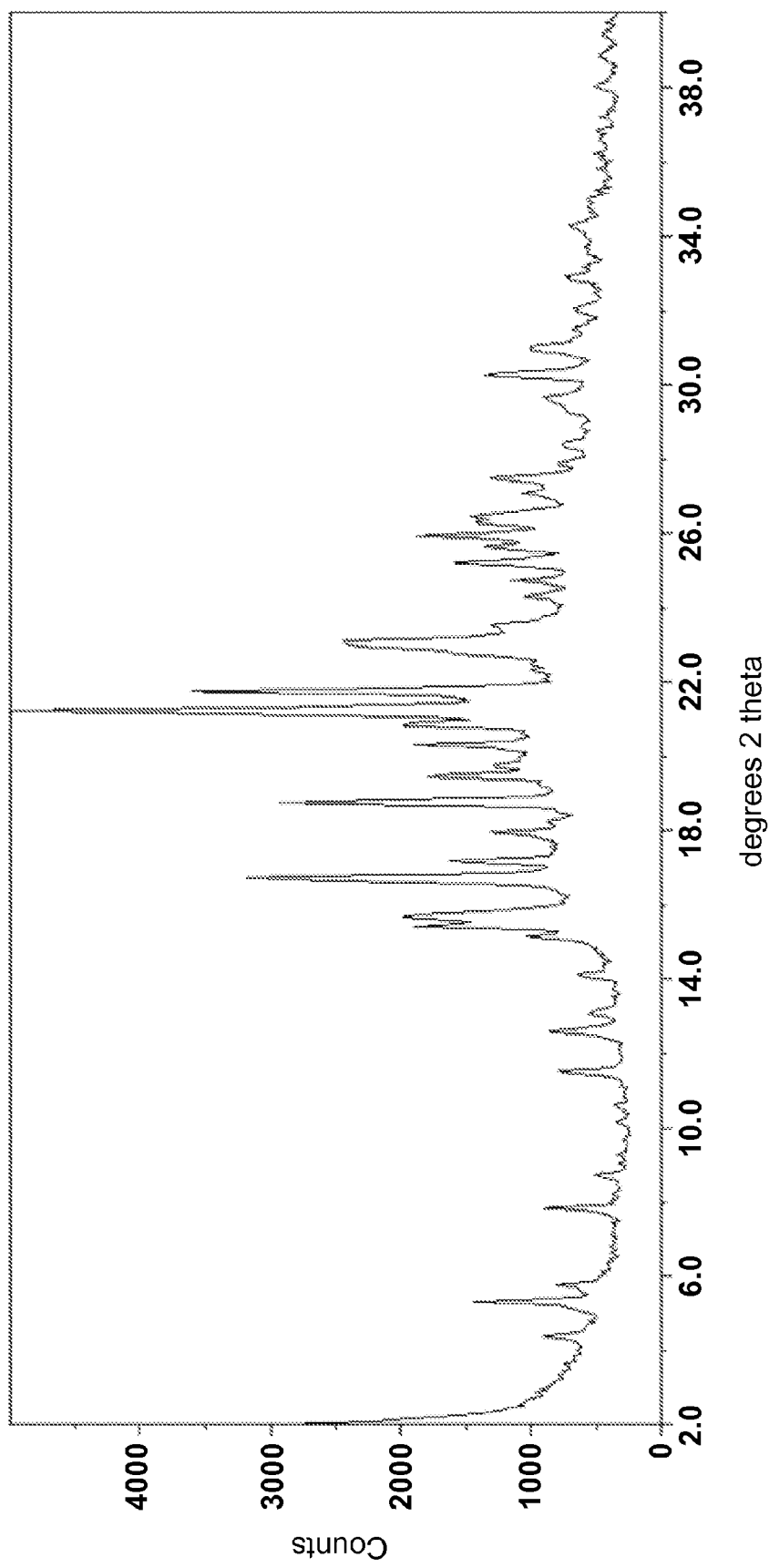
FIG. 1g shows a powder XRD pattern of crystalline Form S7 of Sitagliptin sulfate.
Figure 1H:
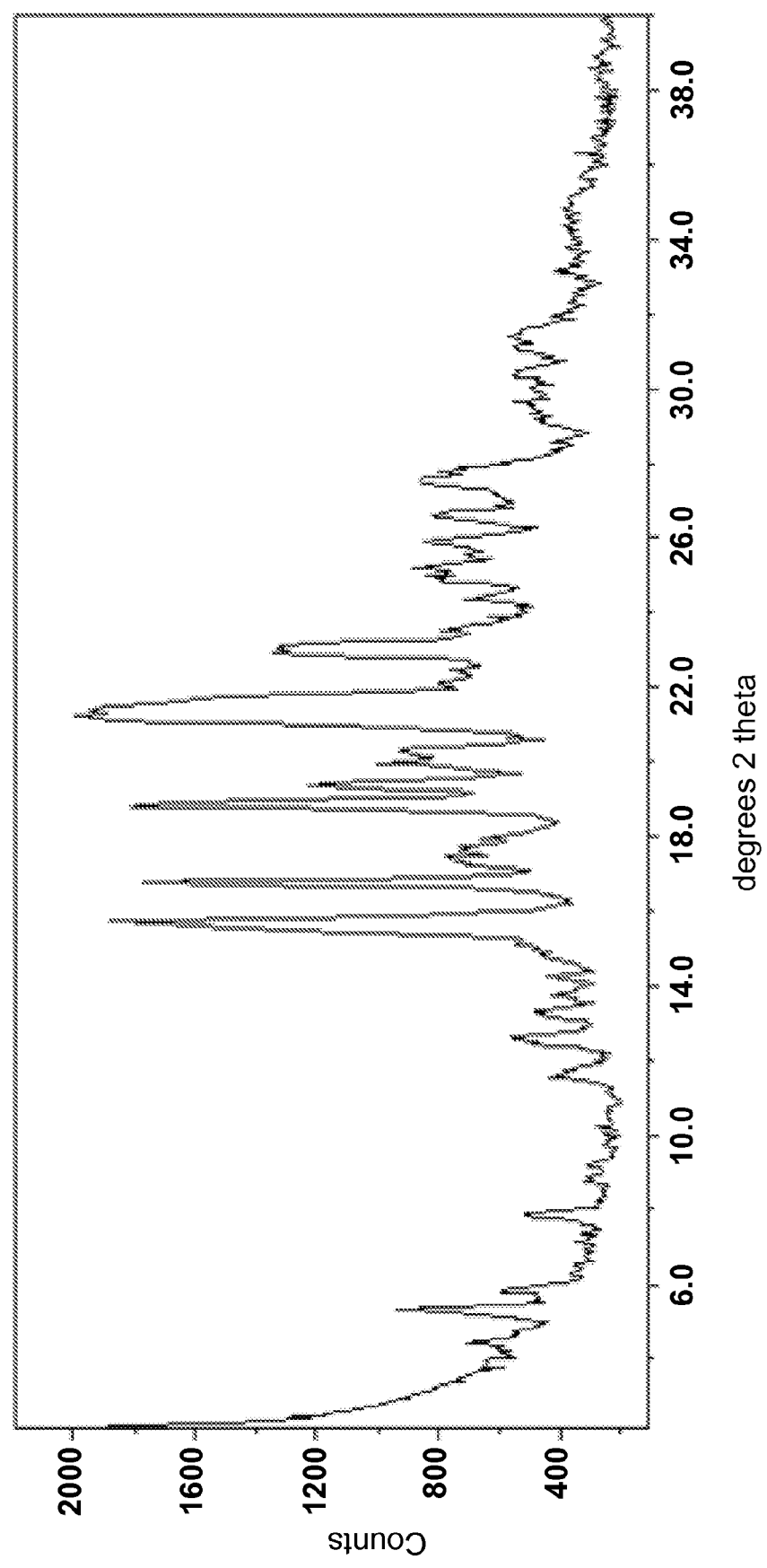
FIG. 1h shows a powder XRD pattern of crystalline Form S7 of Sitagliptin sulfate.
Figure 1I:
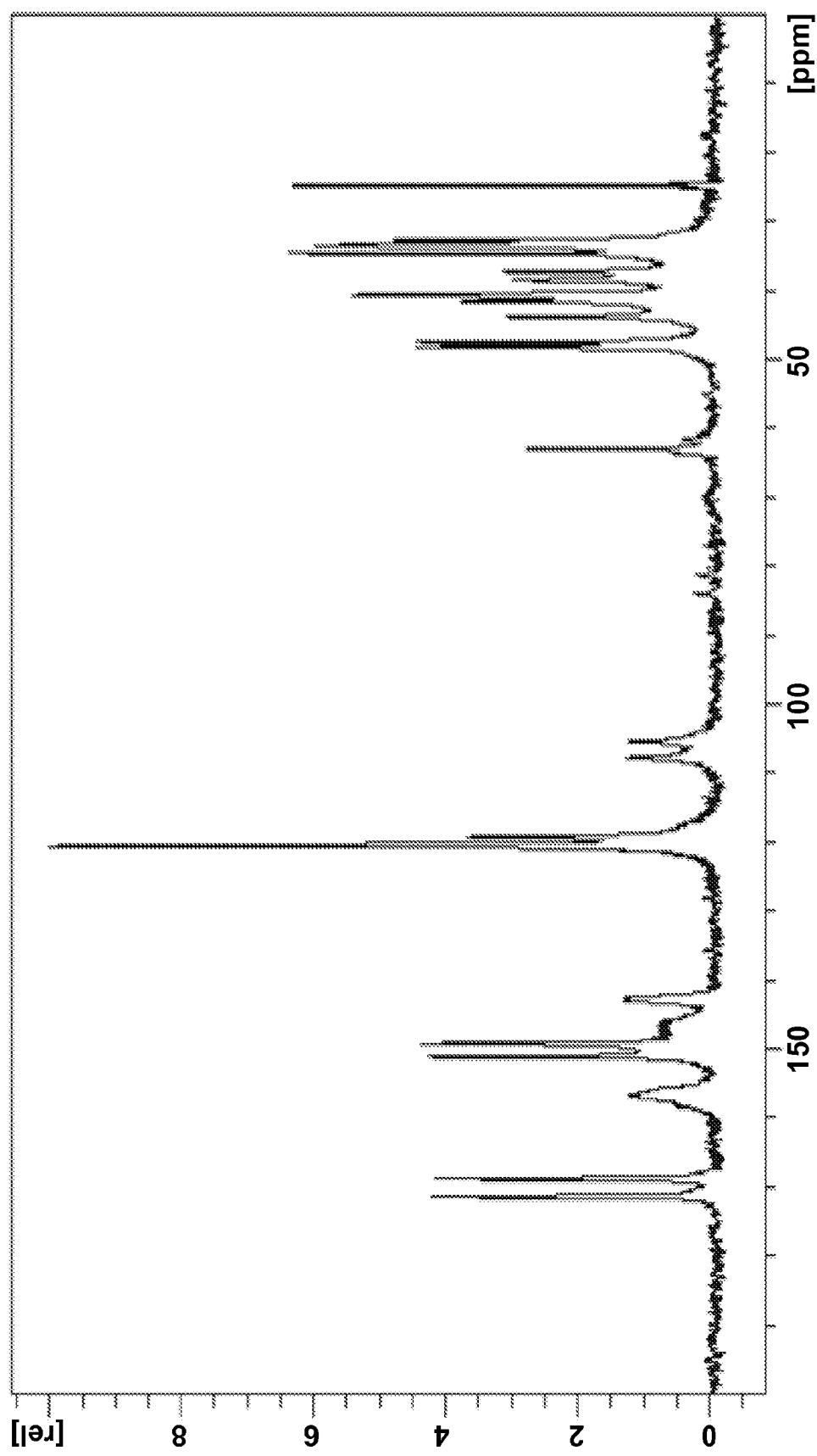
FIG. 1i shows a solid state $^{13}$C NMR spectrum of Sitagliptin sulfate Form S7 in the 0-200 ppm range.
Figure 1J:
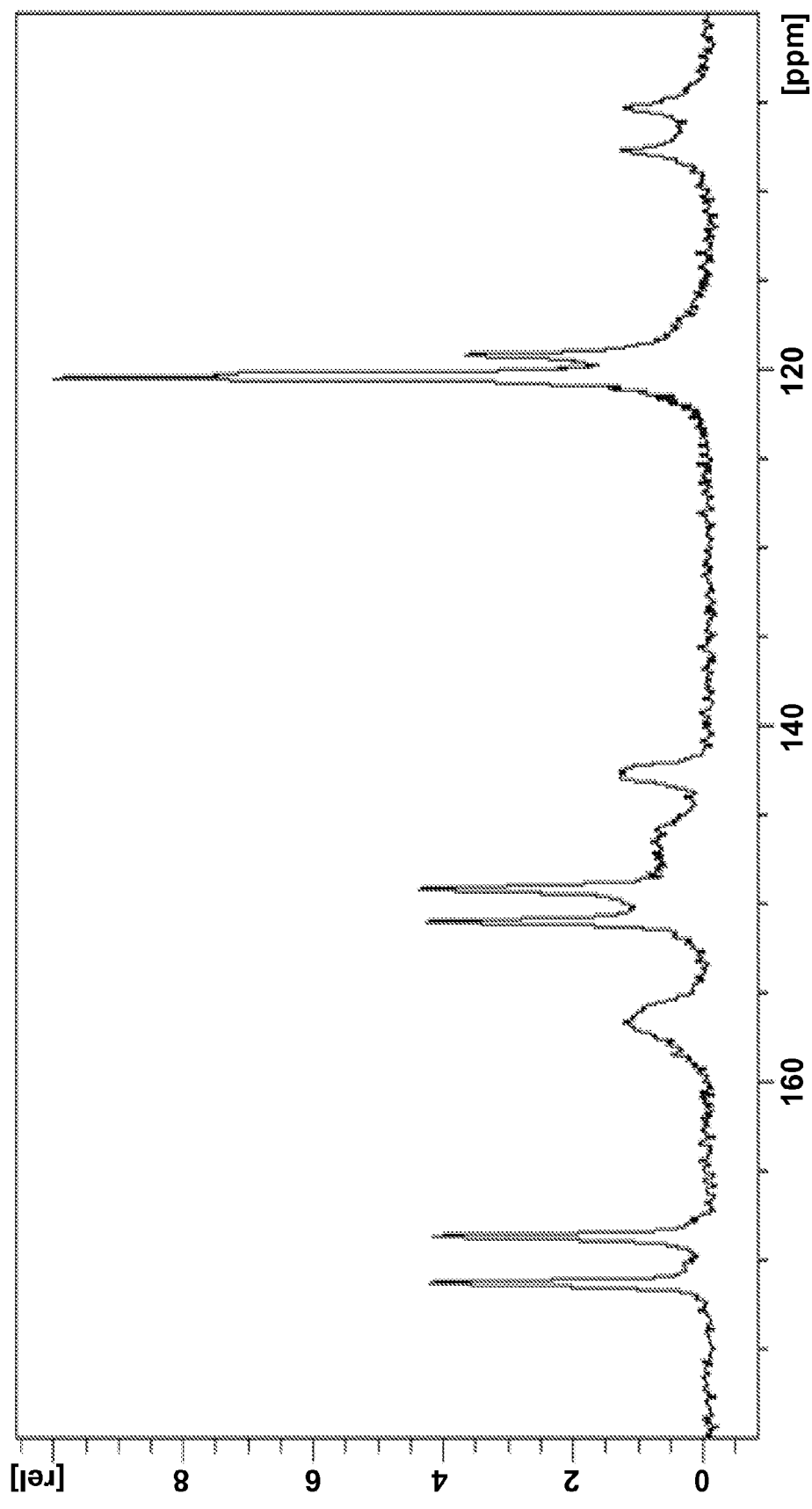
FIG. 1j shows a solid state $^{13}$C NMR spectrum of Sitagliptin sulfate Form S7 in the 100-180 ppm range.
Figure 1K:
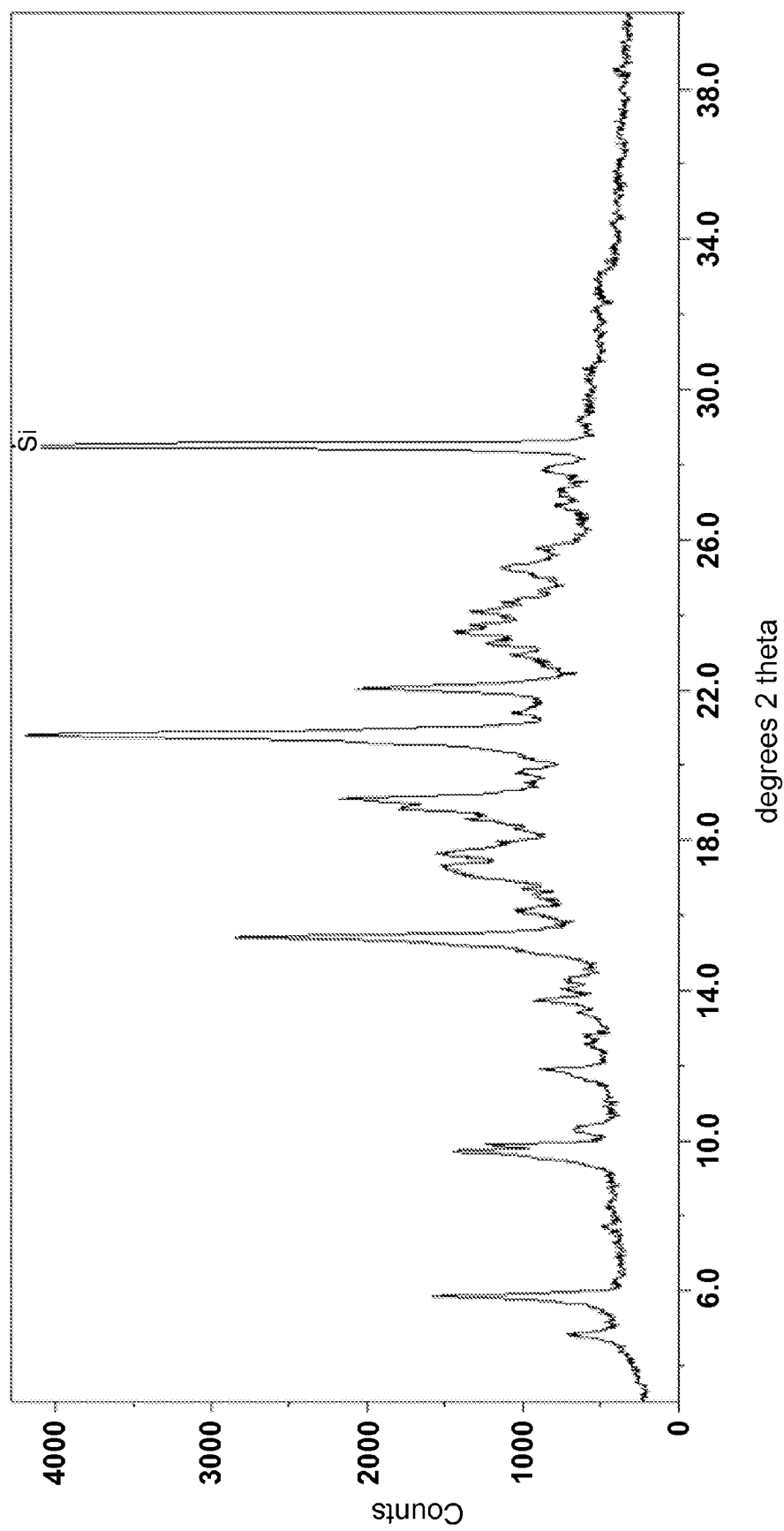
FIG. 1k shows a powder XRD pattern of crystalline Form S8 of Sitagliptin sulfate. The peak at 28.5° is attributed to silicon powder, added to the sample as internal standard.
Figure 1I:
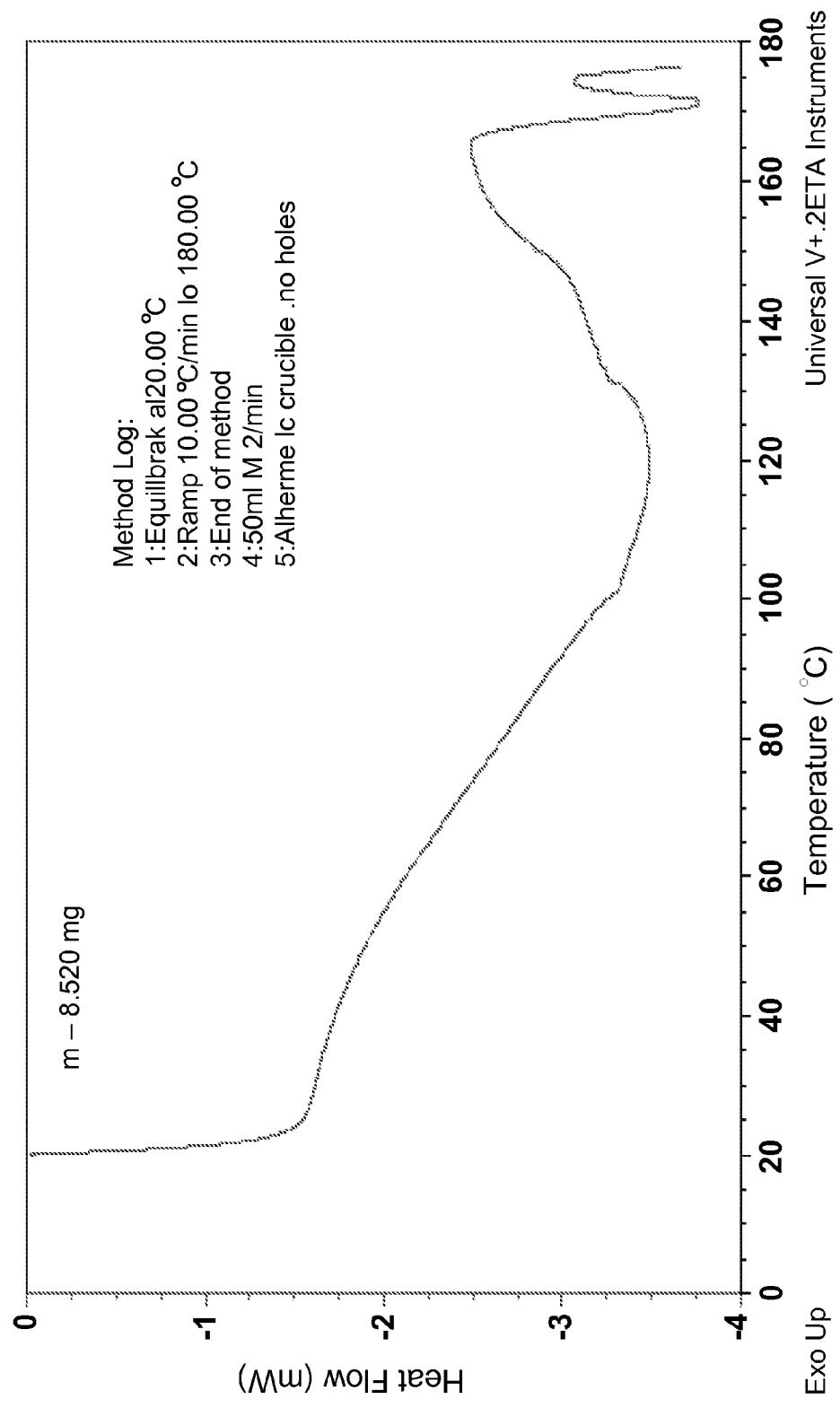
Figure 1M:
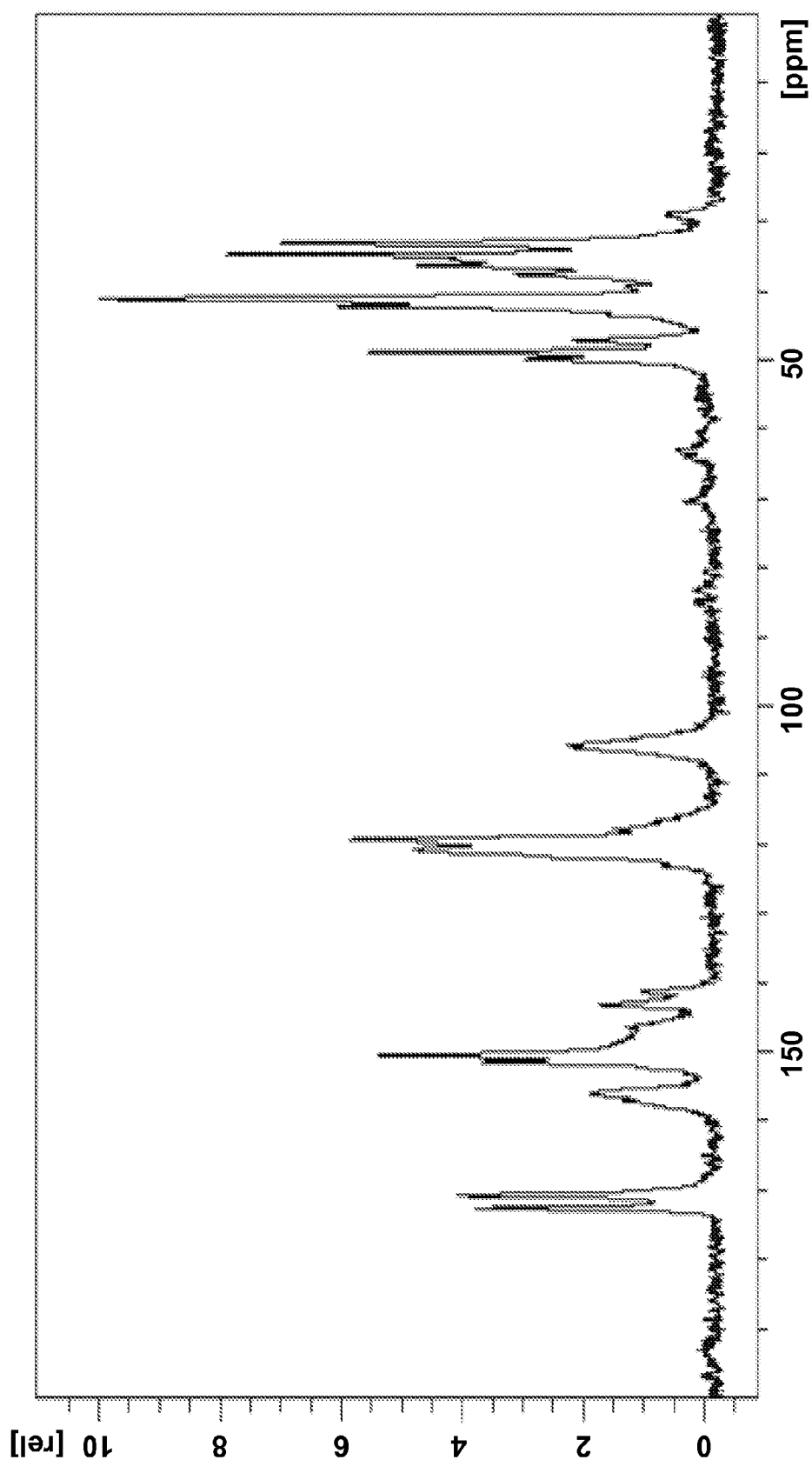
FIG. 1m shows a solid-state $^{13}$C NMR spectrum of Sitagliptin sulfate Form S2 in the 0-200 ppm range.
Figure 1N:
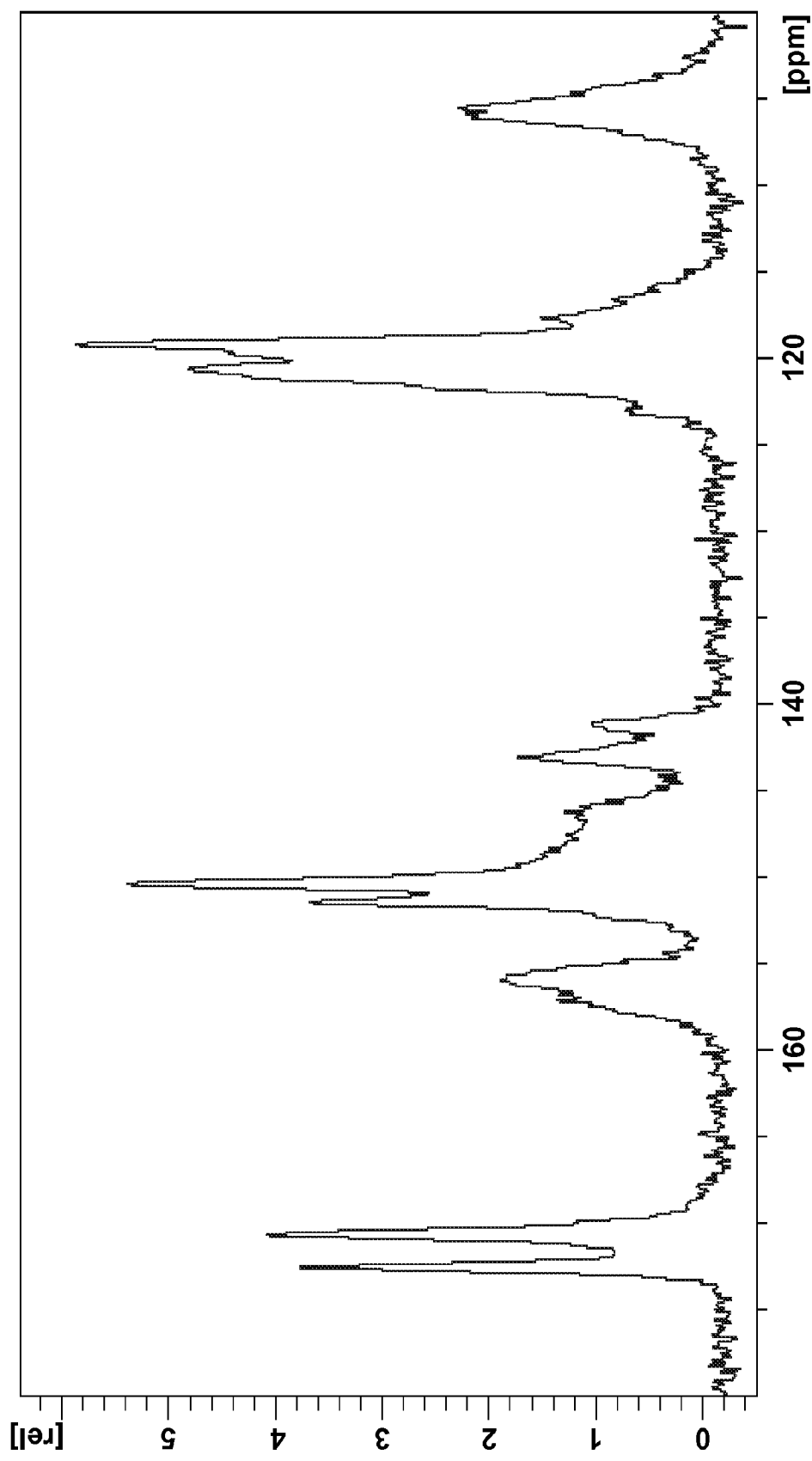
FIG. 1n shows a solid-state $^{13}$C NMR spectrum of Sitagliptin sulfate Form S2 in the 100-180 ppm range.

In one embodiment, the present invention provides a crystalline Sitagliptin sulfate, designated Form S2, characterized by data selected from: a powder XRD pattern with peaks at 9.3°, 9.7°, 15.2°, 15.6° and 25.4°±0.2° 2θ; a powder XRD pattern as shown in FIG. 1b; a solid-state $^{13}$C NMR spectrum with signals at 119.2, 150.3 and 170.6±0.2 ppm; a solid-state $^{13}$C NMR spectrum having chemical shifts differences between the signal exhibiting the lowest chemical shift and another in the chemical shift range of 100 to 180 ppm of 13.7, 44.8 and 65.1±0.1 ppm; a $^{13}$C NMR spectrum as depicted in FIGS. 1m and 1n; and combinations thereof. The signal exhibiting the lowest chemical shift in the chemical shift area of 100 to 180 ppm is typically at 105.5±1 ppm.

Sitagliptin sulfate Form S2 can be also characterized by a powder XRD pattern with peaks at 9.3°, 9.7°, 11.9°, 15.2°, 15.6°, 17.6°, 18.5°, 18.9°, 20.9° and 25.4°±0.2° 2θ.

Sitagliptin sulfate Form S2 preferably has advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density. In particular, Form S2 may have at least one of: high crystallinity, good mechanical stability, thermal stability, flowability, and solubility over a wide range of pH.

Sitagliptin sulfate crystalline Form S2 can be prepared by a process comprising forming a solution of Sitagliptin base in acetonitrile; combining the solution with sulfuric acid to form a precipitate; and isolating the obtained precipitate. Preferably, the sulfuric acid is used at a mol ratio of about 1:0.5 of Sitagliptin base to sulfuric acid.

In another embodiment, the present invention provides a crystalline Sitagliptin sulfate, designated Form S6, characterized by data selected from: a powder XRD pattern with peaks at 5.5°, 13.4°, 15.1°, 19.0° and 21.1°±0.3° 2θ; a powder XRD diffractogram shown in FIG. 1f; and combinations thereof.

Sitagliptin sulfate Form S6 preferably has advantageous properties selected from at least one of: solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density. In particular, Form S6 may have at least one of: good mechanical stability, thermal stability, flowability, and solubility over a wide range of pH.

Sitagliptin sulfate crystalline Form S6 can be prepared by a process comprising forming a solution of Sitagliptin base in ethyl acetate; combining the solution with sulfuric acid to form a precipitate; and isolating the obtained precipitate. The obtained precipitate can be further dried. Preferably, the sulfuric acid is used at a mol ratio of about 1:0.5 of Sitagliptin base to sulfuric acid.

In another embodiment, the present invention provides a crystalline Sitagliptin sulfate isopropanol solvate, designated Form S7, characterized by data selected from: a powder XRD pattern with peaks at 5.2°, 15.6°, 16.6°, 18.7° and 21.1°±0.2° 2θ; a powder XRD diffractogram shown in FIG. 1g; a solid-state $^{13}$C NMR spectrum with signals at 120.4, 149.1 and 171.2±0.2 ppm; a solid-state $^{13}$C NMR spectrum having chemical shifts differences between the signal exhibiting the lowest chemical shift and another in the chemical shift range of 100 to 180 ppm of 15.1, 43.8 and 65.9±0.1 ppm; and a $^{13}$C NMR spectrum as depicted in FIGS. 1i and 1j; and combinations thereof. The signal exhibiting the lowest chemical shift in the chemical shift area of 100 to 180 ppm is typically at 105.3±1 ppm.

Alternatively, Form S7 can be characterized a powder XRD pattern with peaks at 5.2°, 15.6°, 16.6°, 17.1°, 18.7°, 19.4°, 17.0°, 20.2°, 21.1°, 21.7° and 22.9°±0.2° 2θ.

Figure 1O:
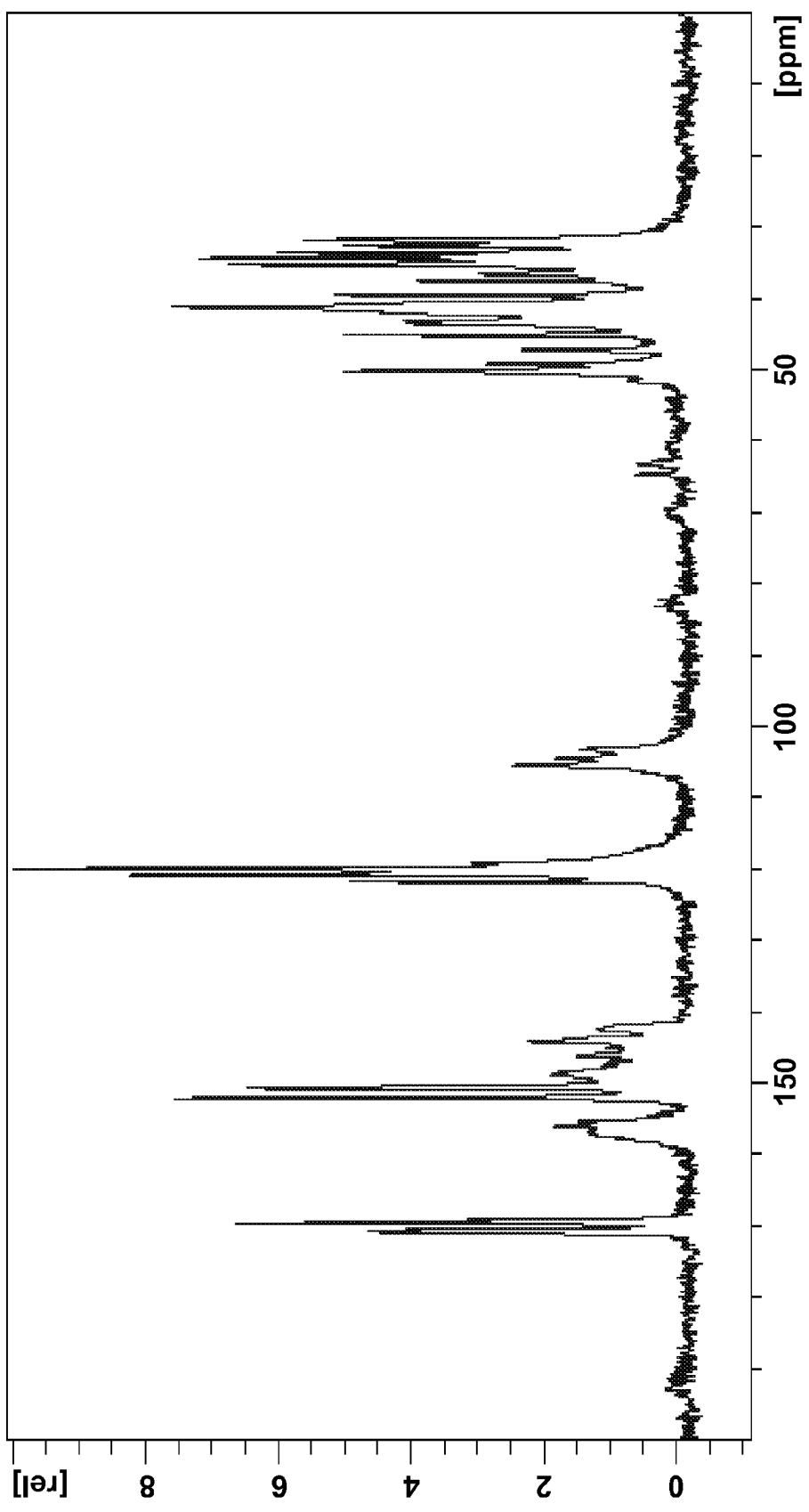
FIG. 1o shows a solid-state $^{13}$C NMR spectrum of Sitagliptin sulfate Form S3 in the 0-200 ppm range.
Figure 1P:
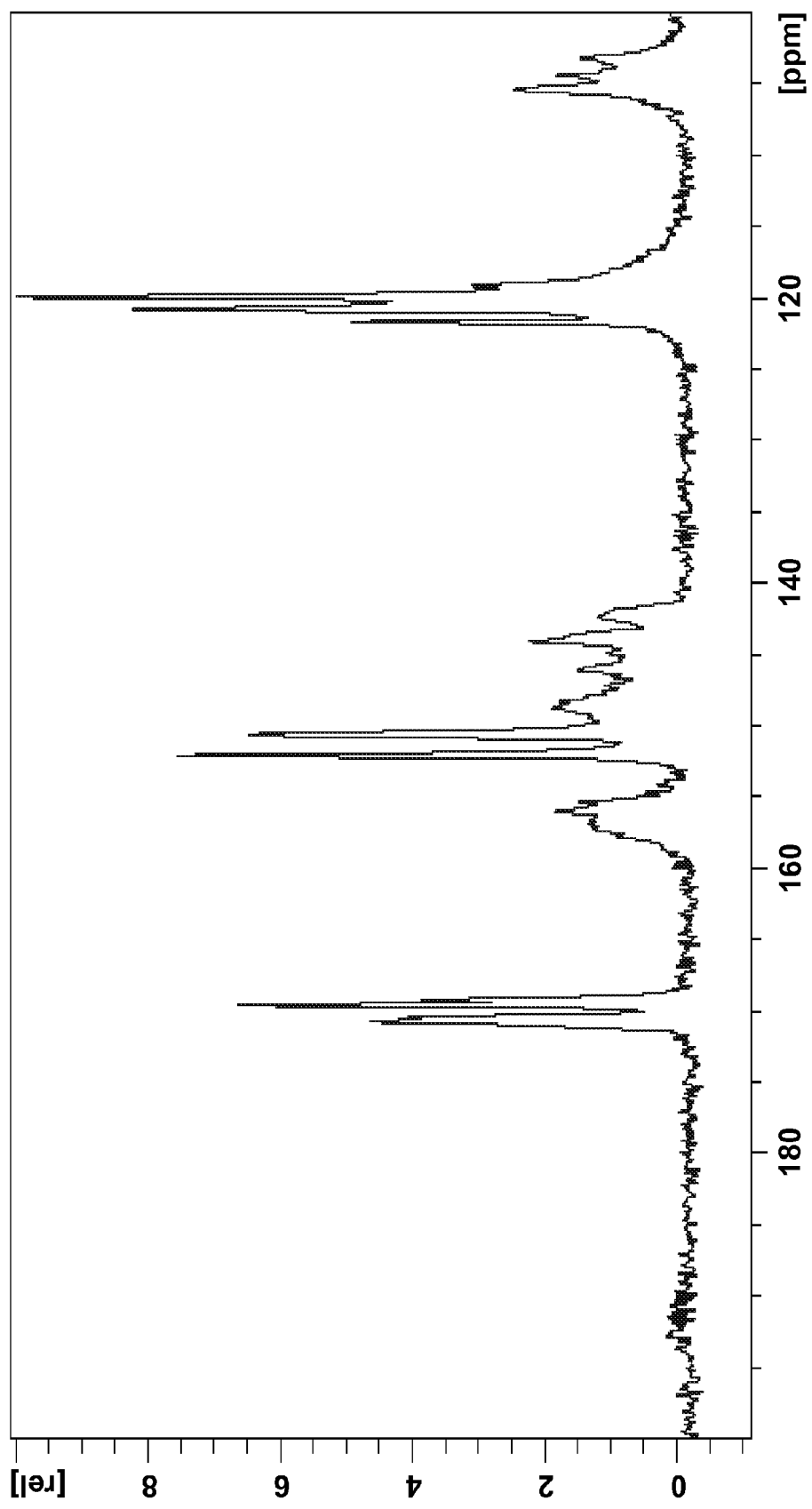
FIG. 1p shows a solid-state $^{13}$C NMR spectrum of Sitagliptin sulfate Form S3 in the 100-200 ppm range.
Figure 1R:
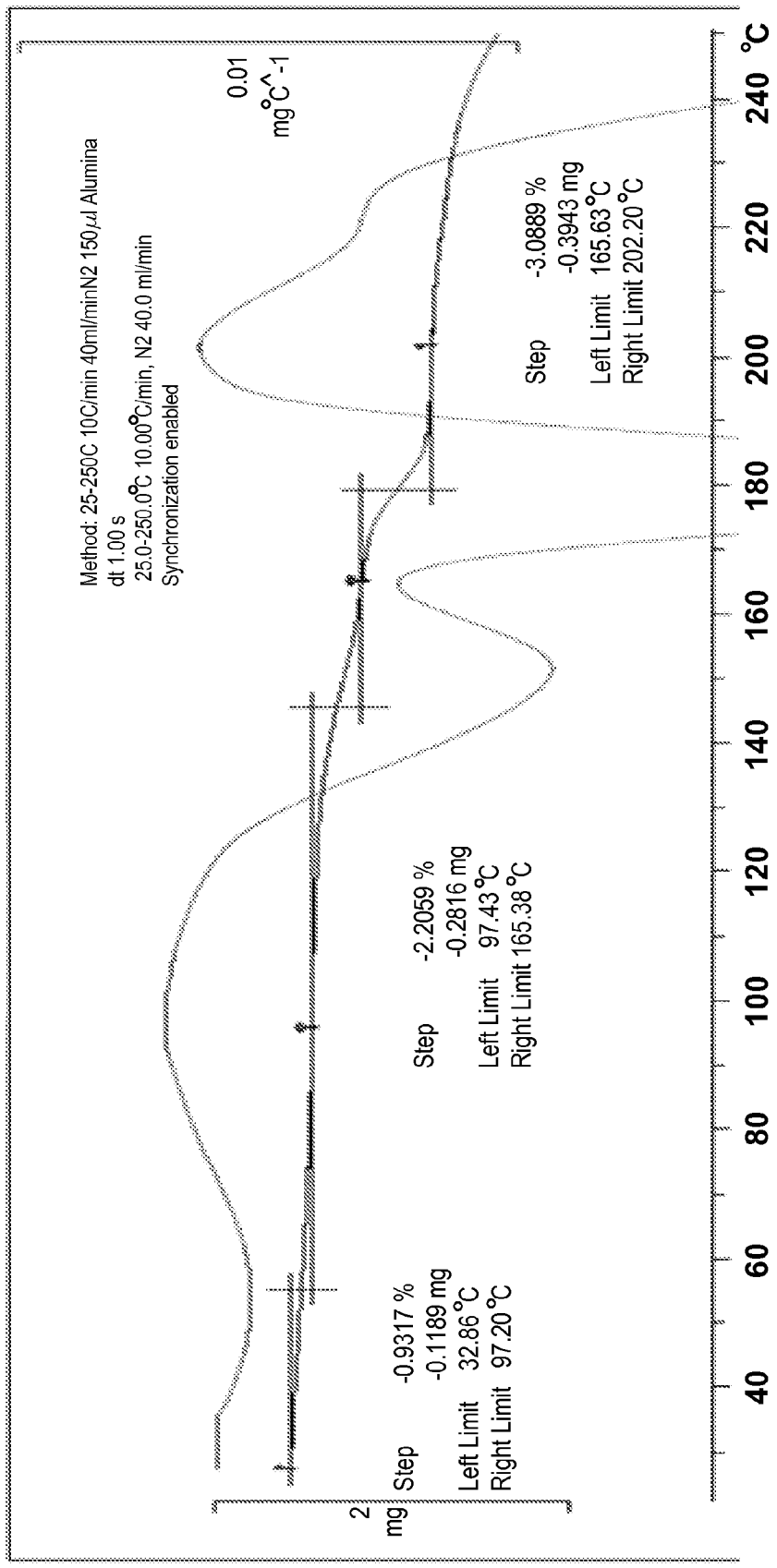
FIG. 1r shows a TGA termogram of Sitagliptin sulfate isopropanol solvate Form S7.

Sitagliptin sulfate Form S7 can be characterized by the TGA thermogram as shown in FIG. 1r.

Sitagliptin sulfate Form S7 preferably has advantageous properties selected from at least one of: solubility, dissolution rate, morphology, thermal and mechanical stability to polymorphic conversion and/or to dehydration, storage stability, a lower degree of hygroscopicity, flowability, and advantageous processing and handling characteristics such as compressibility, and bulk density. In particular, Form S7 may have at least one of: good mechanical stability, thermal stability, flowability, and solubility over a wide range of pH.

Sitagliptin sulfate crystalline Form S7 can be prepared by a process comprising forming a solution of Sitagliptin base in isopropanol; combining the solution with sulfuric acid to form a precipitate; and isolating the obtained precipitate. The obtained precipitate can be further dried. Preferably, the sulfuric acid is used at a mol ratio of about 1:0.5 of Sitagliptin base to sulfuric acid.

In another embodiment, the present invention provides a crystalline Sitagliptin sulfate designated Form S1, characterized by data selected from: a powder XRD pattern with peaks at 11.8°, 13.7°, 14.4°, 17.0° and 17.5°±0.2° 2θ; a powder XRD diffractogram as shown in FIG. 1a; and combinations thereof.

Sitagliptin sulfate Form S1 can be also characterized by a powder XRD pattern with peaks at 5.0°, 9.9°, 11.8°, 12.6°, 13.7°, 14.4°, 17.0°, 17.5° 19.0° and 20.8°±0.2° 2θ.

Sitagliptin sulfate Form S1 preferably has advantageous properties selected from at least one of: solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density. In particular, Form S6 may have at least one of: good mechanical stability, thermal stability, and flowability.

Sitagliptin sulfate crystalline Form S1 can be prepared by a process comprising forming a solution of Sitagliptin base in isopropanol; combining that solution with sulfuric acid to form a precipitate; and isolating the obtained precipitate. Preferably, the sulfuric acid is used at a mol ratio of about 1:1 of Sitagliptin base to sulfuric acid.

In this process, and in the processes for the preparation of any of the crystalline Sitagliptin sulfate, after combining with sulfuric acid, the solution can be maintained at a temperature from about room temperature to about 50° C., or at about room temperature, for example overnight. The precipitate is recovered by any conventional method known in the art, for example, by filtration. The precipitate may be dried at about 30° C. to about 60° C., or about 40° C. and about 50° C., for example, about 40° C. The drying can be carried out under reduced pressure (i.e., less than 1 atmosphere, for example, about 10 mbar to about 100 mbar, or about 10 mbar to about 25 mbar). The drying can take place over a period of about 8 hours to about 36 hours, about 10 hours to about 24 hours, for example, about 16 hours, or can be carried out overnight.

The present invention relates to crystalline form of Sitagliptin acetate, referred herein as Form E1.

Figure 9A:
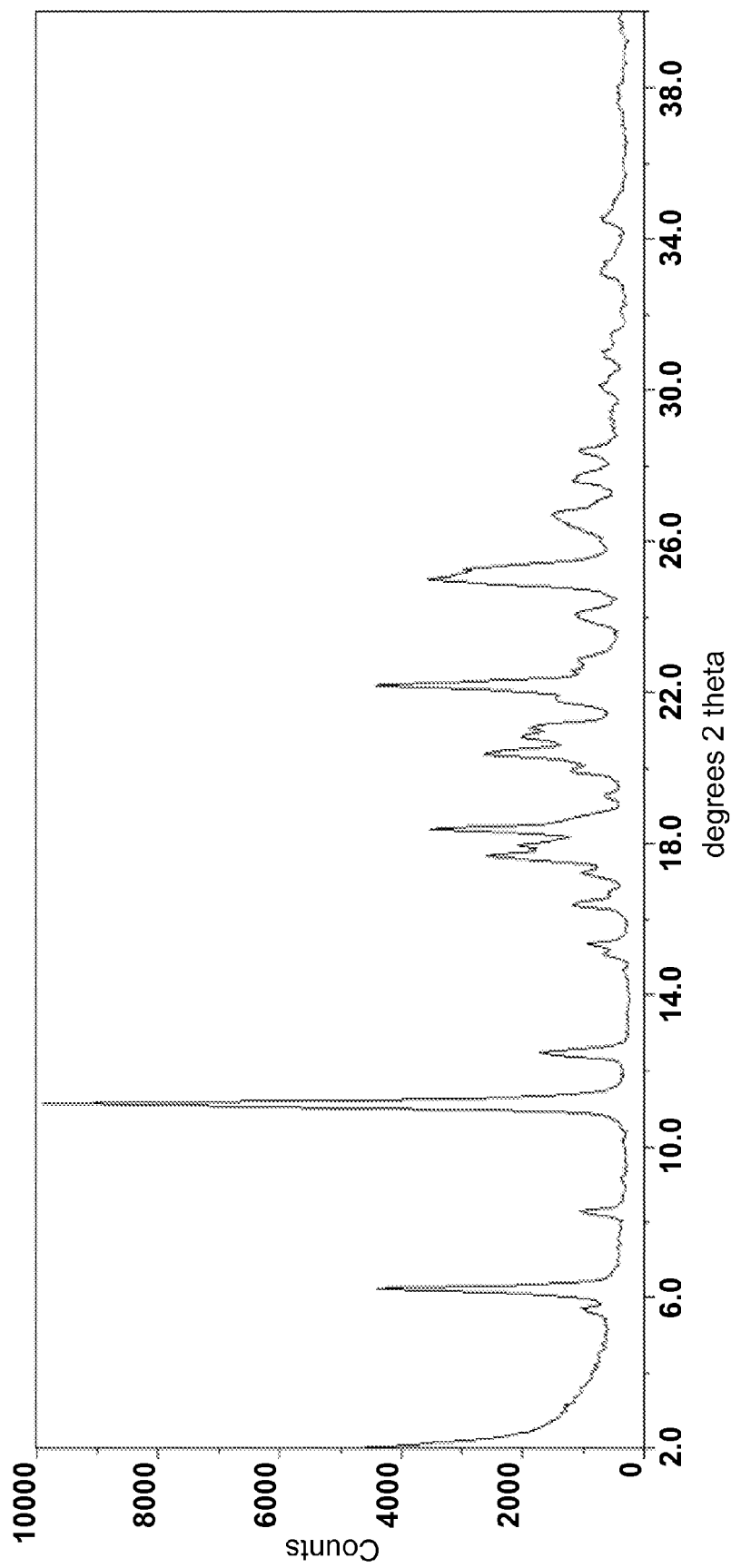
FIG. 9a shows a powder XRD pattern of crystalline Form E1 of Sitagliptin acetate.
Figure 9B:
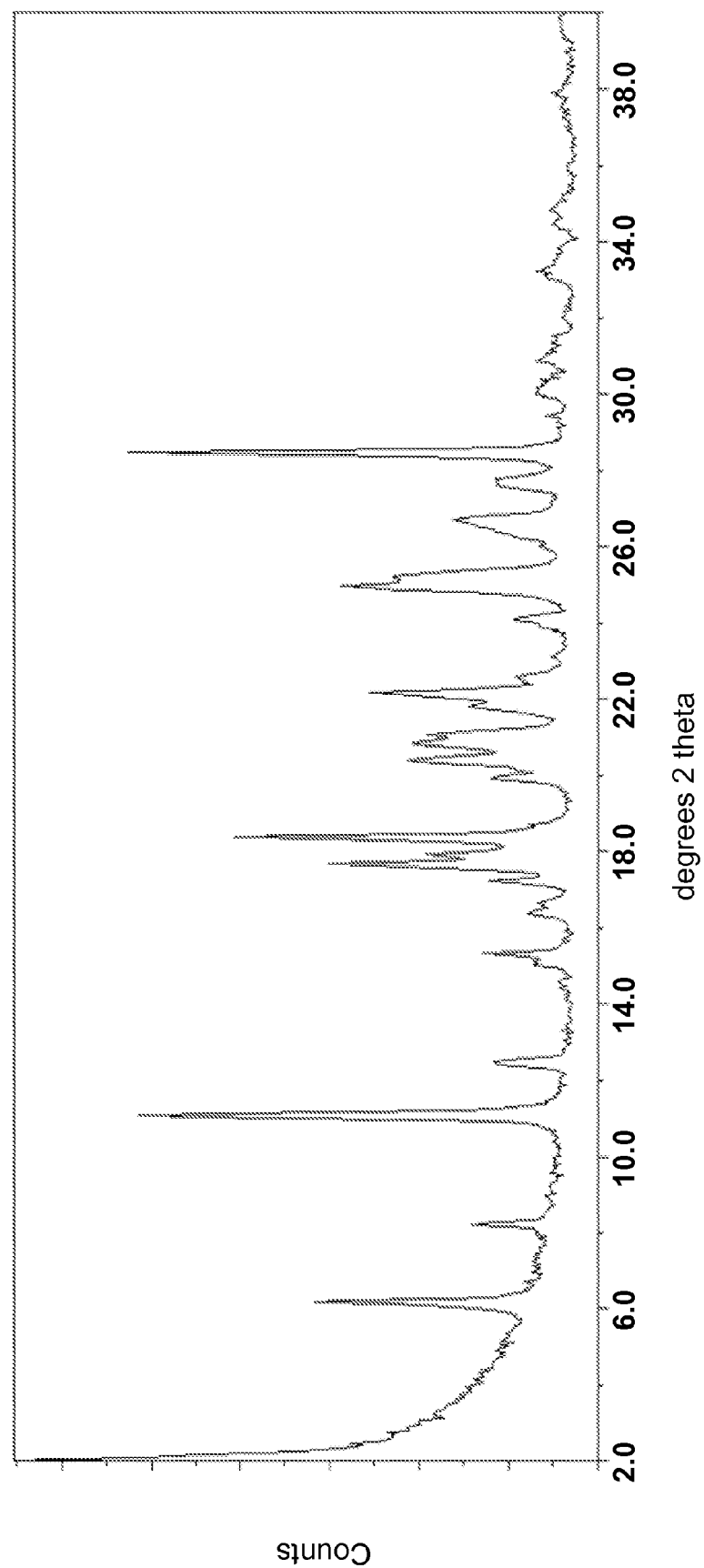
FIG. 9b shows a XRD diffractogram of Acetate form E1 pure from peaks at 5.7°, 19.2° and 22.8° 2theta. The peak at 28.5° is attributed to silicon powder, added to the sample as internal standard.
Figure 9C:
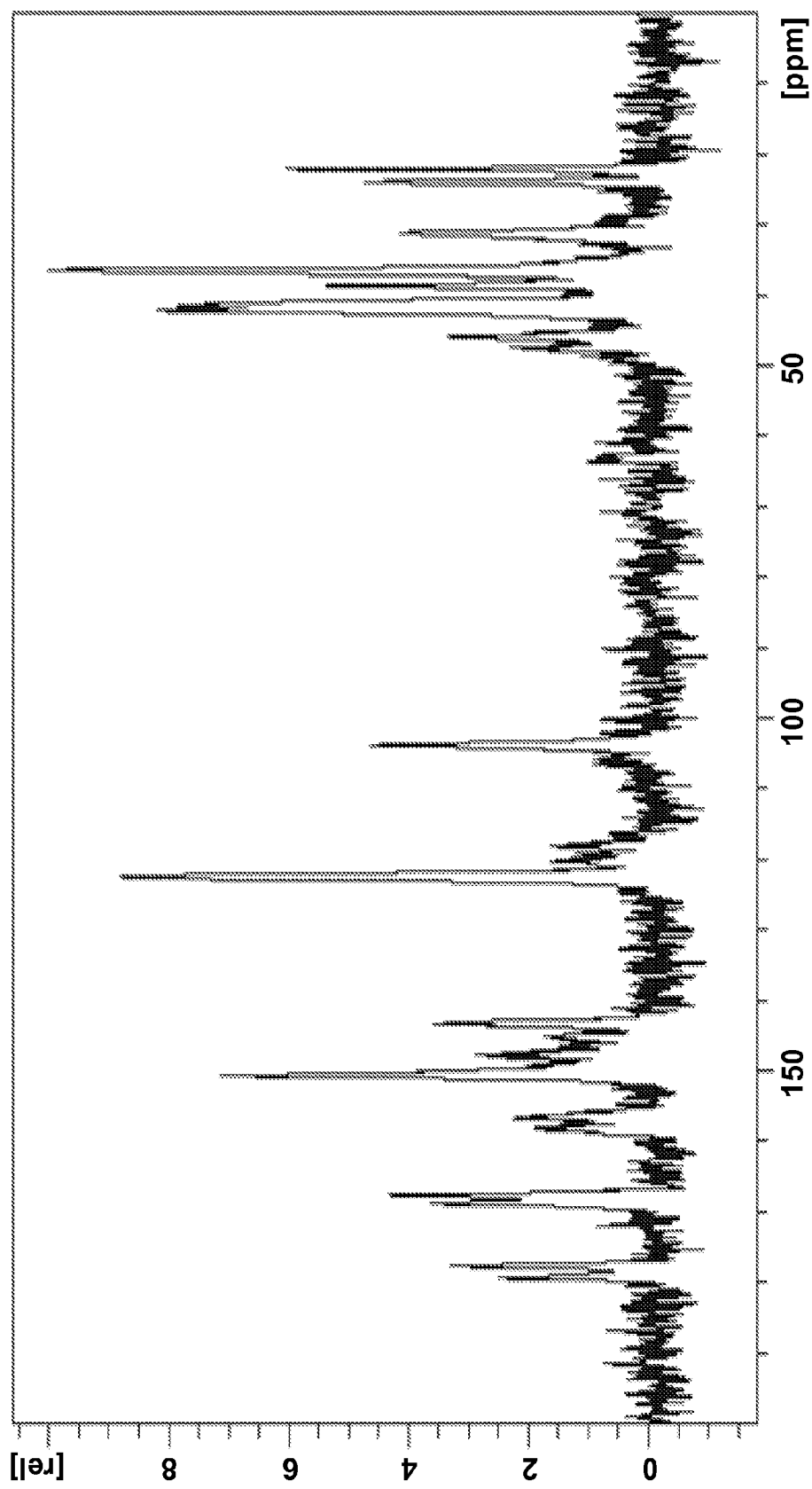
FIG. 9c shows a solid-state $^{13}$C NMR spectrum of Sitagliptin acetate Form E1 in the 0-200 ppm range.
Figure 9D:
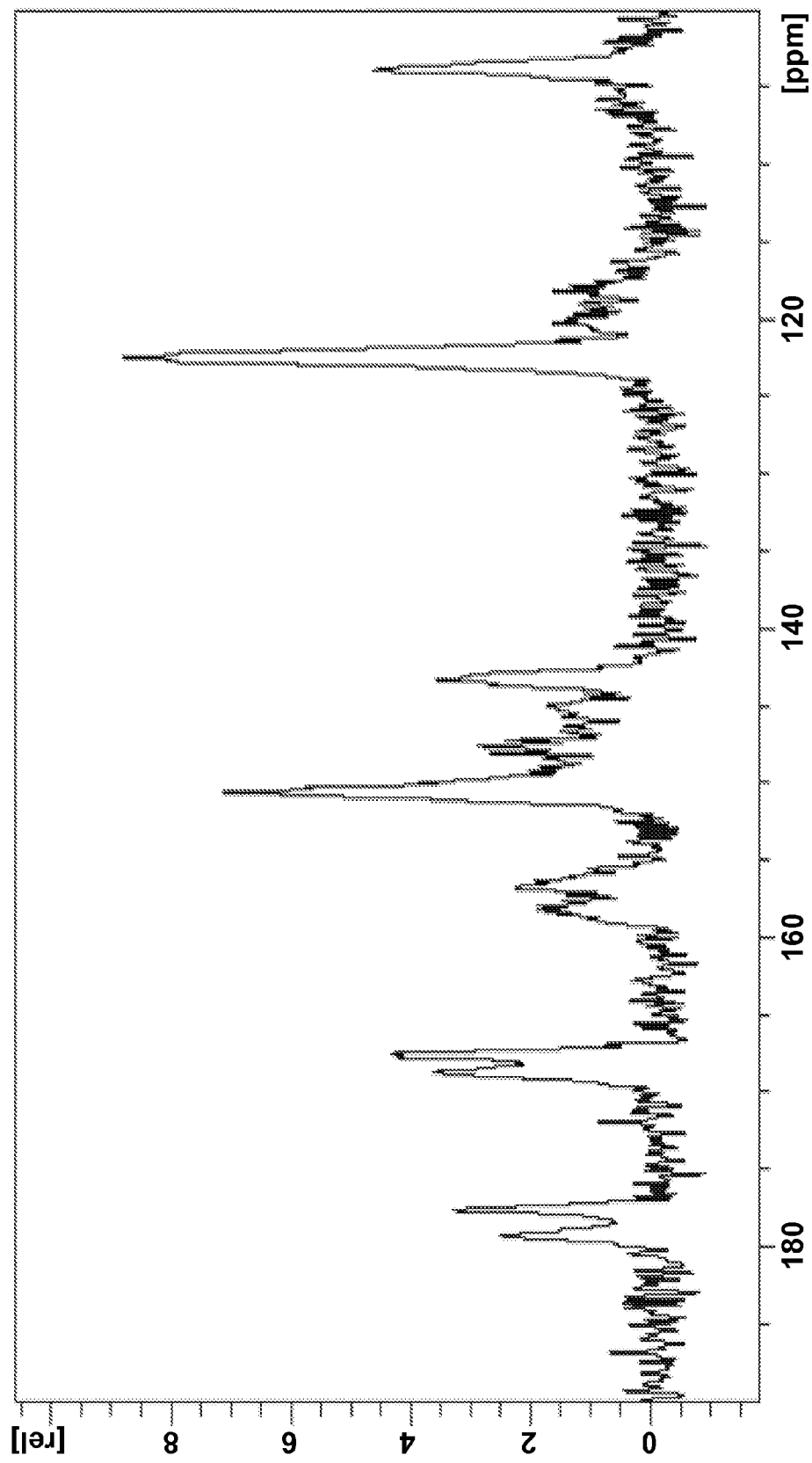
FIG. 9d shows a solid-state $^{13}$C NMR spectrum of Sitagliptin acetate Form E1 in the 100-190 ppm range.

In one embodiment, the present invention provides a crystalline Sitagliptin acetate, designated Form E1, characterized by data selected from: a powder XRD pattern with peaks at 6.2°, 11.1°, 12.5°, 17.7°, and 18.4°±0.2° 2θ; a powder XRD pattern as shown in FIG. 9a; a solid-state $^{13}C$ NMR spectrum with signals at 122.3, 150.5 and 167.4±0.2 ppm; a solid-state $^{13}C$ NMR spectrum having chemical shifts differences between the signal exhibiting the lowest chemical shift and another in the chemical shift range of 100 to 190 ppm of 18.5, 46.7 and 63.6±0.1 ppm; and a $^{13}C$ NMR spectrum as depicted in FIGS. 9c and 9d; and combinations thereof. The signal exhibiting the lowest chemical shift in the chemical shift area of 100 to 180 ppm is typically at 103.8±1 ppm.

Sitagliptin acetate Form E1 can be also characterized by a powder XRD pattern with peaks at 6.2°, 8.3°, 11.1°, 12.5°, 15.3°, 16.4°, 17.7°, 18.4°, 20.4°, and 22.2°±0.2° 2θ.

Sitagliptin acetate Form E1 preferably has advantageous properties selected from at least one of: good crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density. In particular, Form E1 may have at least one of: good mechanical stability, thermal stability, flowability, and solubility over a wide range of pH.

Sitagliptin acetate crystalline Form E1 can be prepared by a process comprising forming a solution or a slurry of Sitagliptin base in ethyl acetate; combining the solution or the slurry with acetic acid to form a precipitate; and isolating the obtained precipitate. The obtained precipitate can be further dried. Preferably, the acetic acid is used at a mol ratio of about 1:1 of Sitagliptin base to acetic acid.

After the addition of the acid, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

The present invention relates to crystalline form of Sitagliptin L-malate, referred herein as Form I1.

Figure 4A:
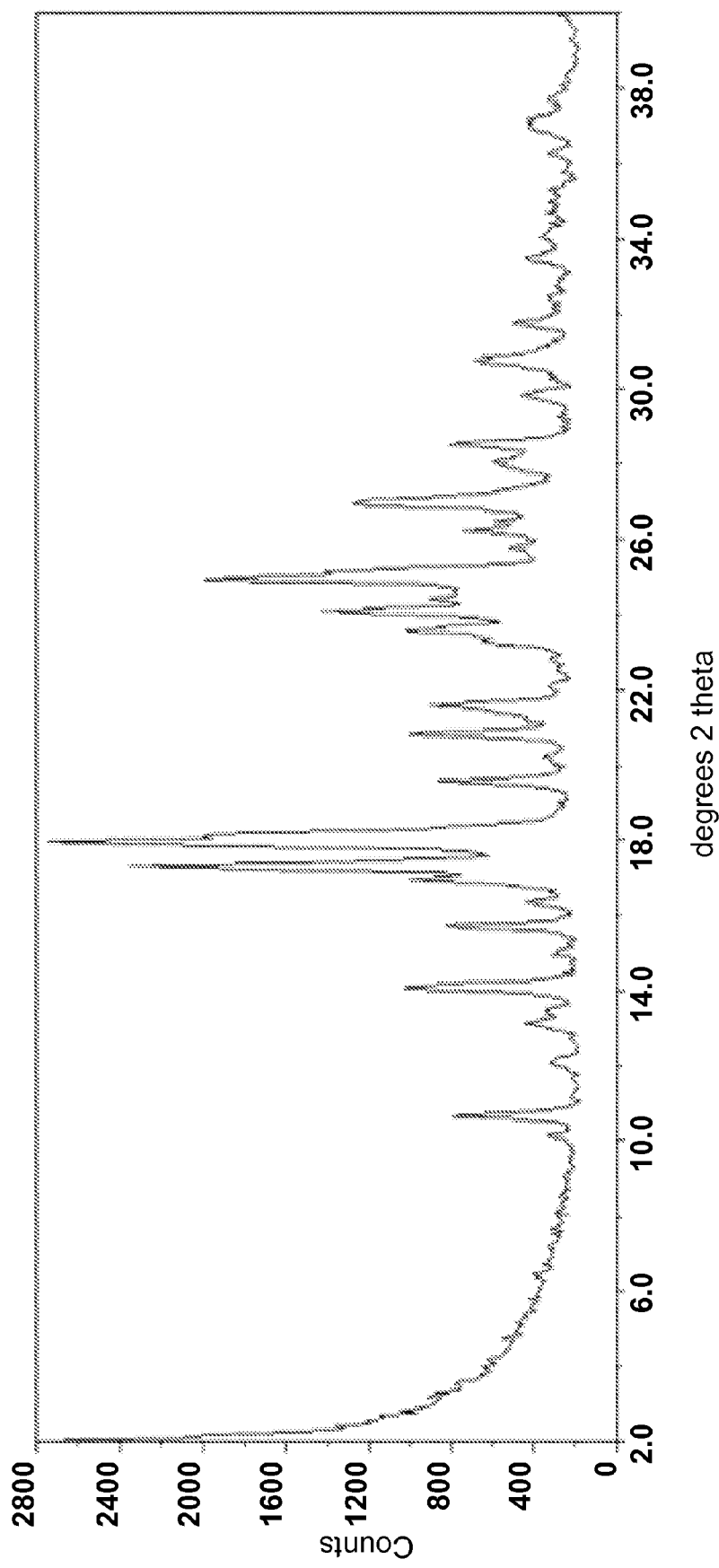
FIG. 4a shows a powder XRD pattern of crystalline Form M1 of Sitagliptin (D)-(+)-malate.
Figure 4B:
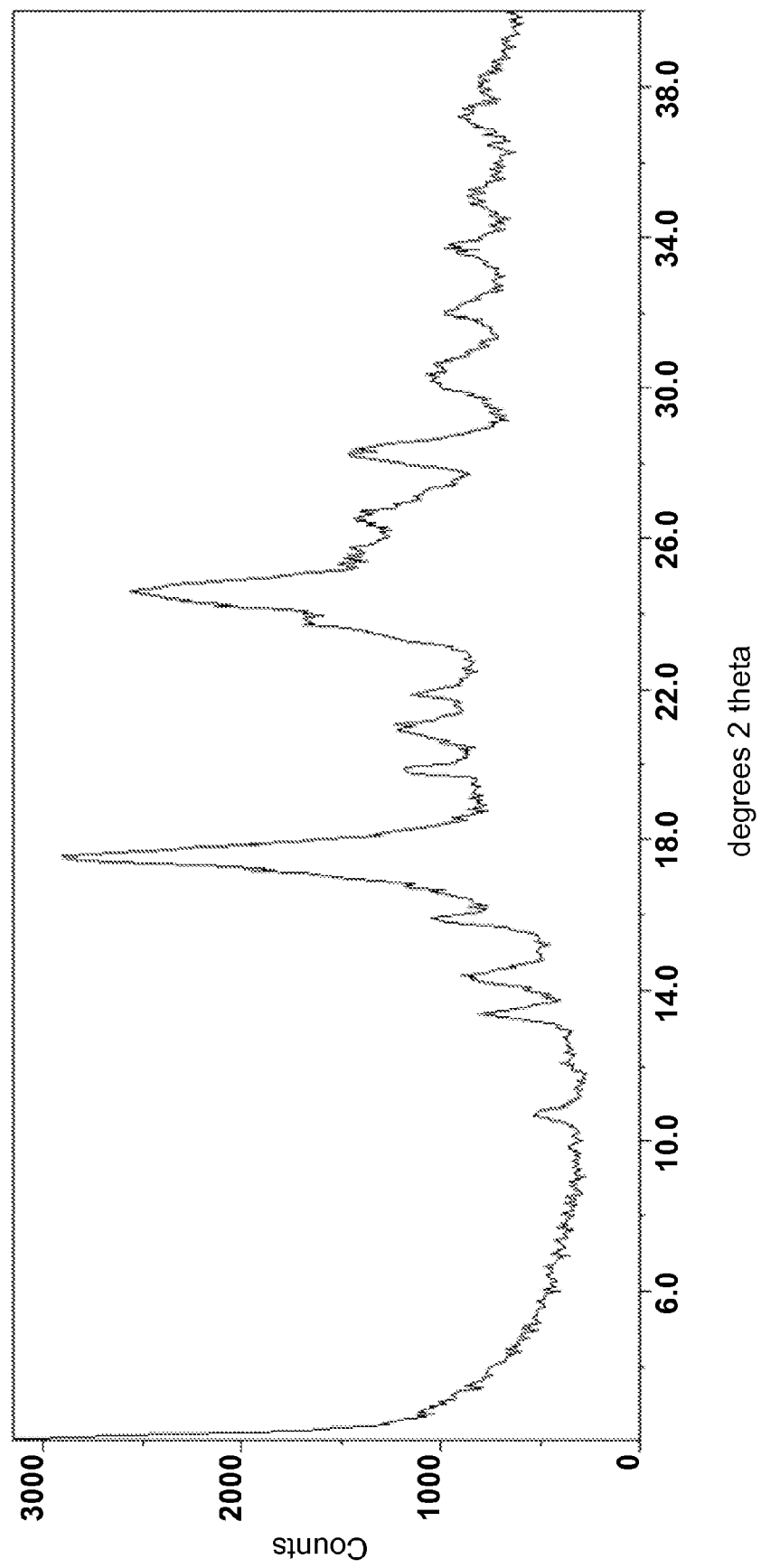
FIG. 4b shows a powder XRD pattern of crystalline Form M2 of Sitagliptin (D)-(+)-malate.
Figure 4C:
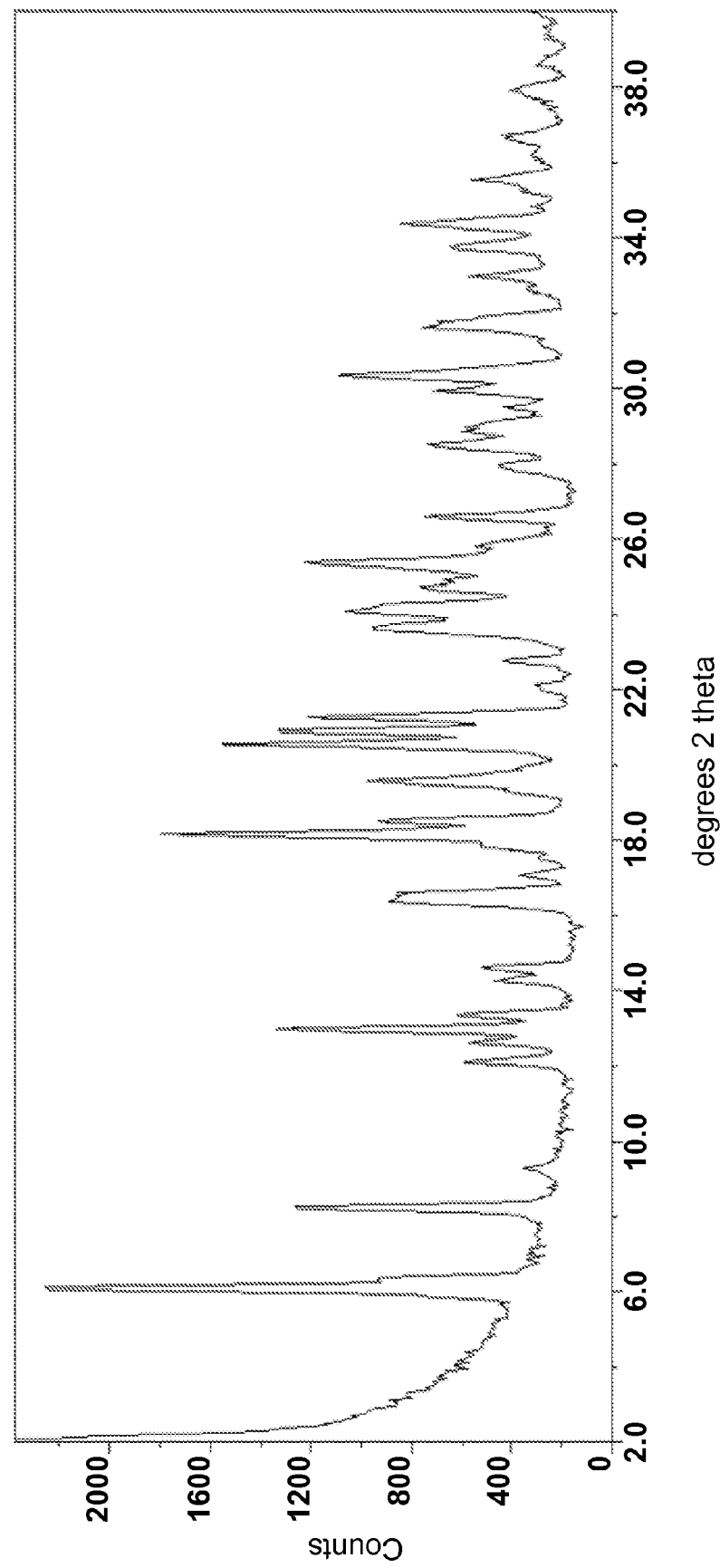
FIG. 4c shows a powder XRD pattern of crystalline Form I1 of Sitagliptin L-malate.
Figure 4D:
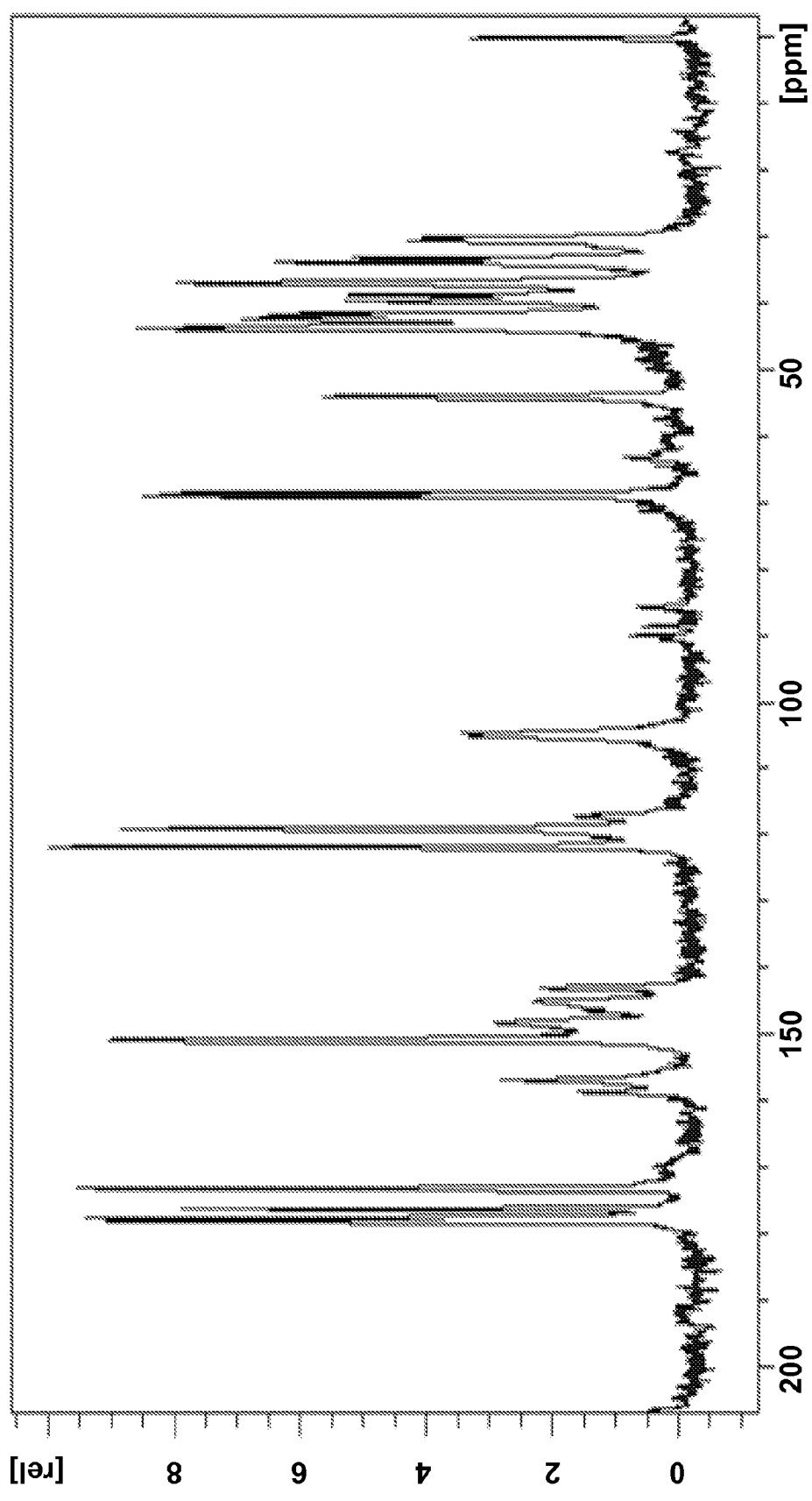
FIG. 4d shows a solid-state $^{13}$C NMR spectrum of Sitagliptin L-malate Form I1 in the −10-200 ppm range.
Figure 4E:
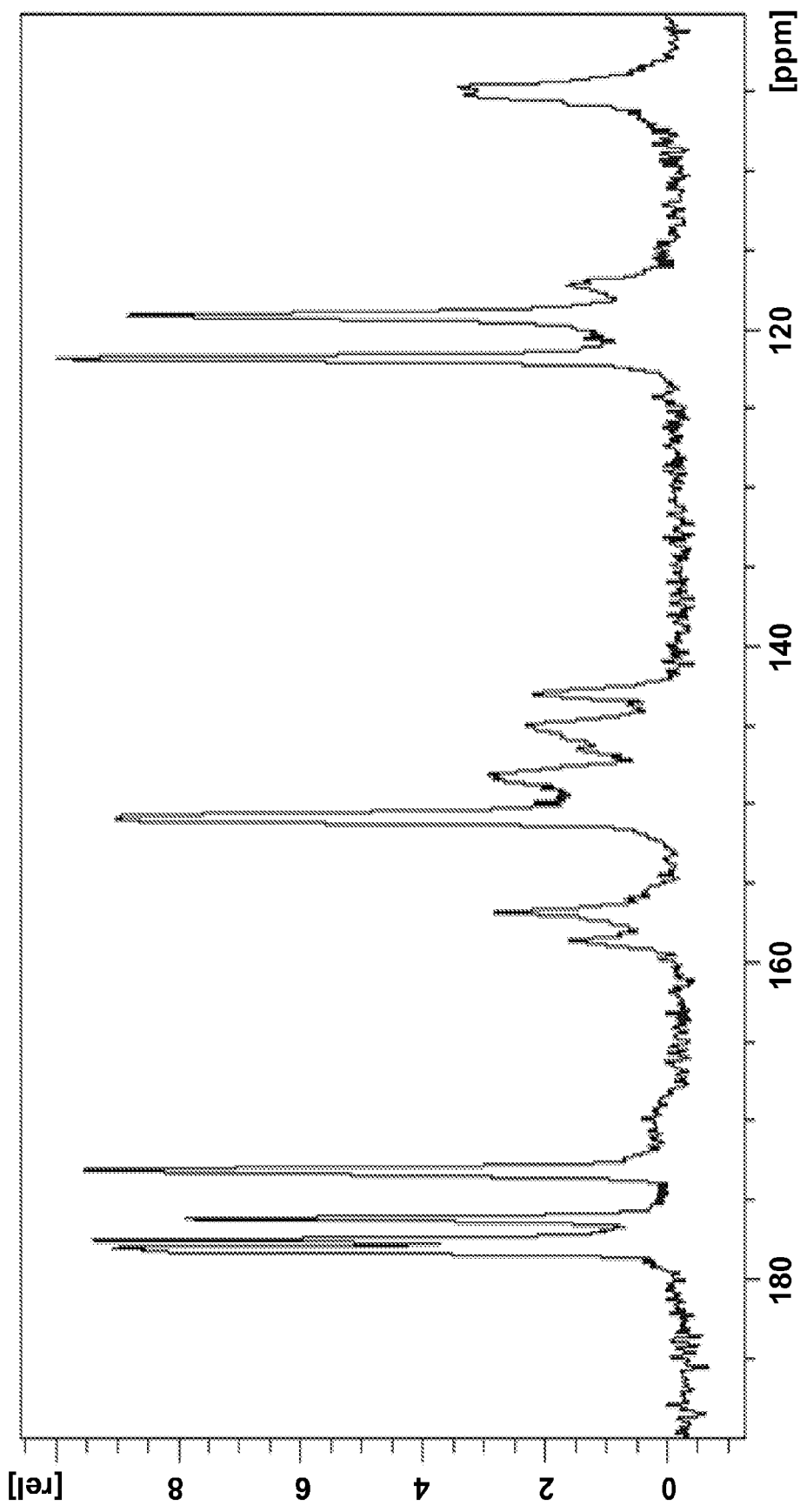
FIG. 4e shows a solid-state $^{13}$C NMR spectrum of Sitagliptin L-malate Form I1 in the 100-190 ppm range.
Figure 4F:
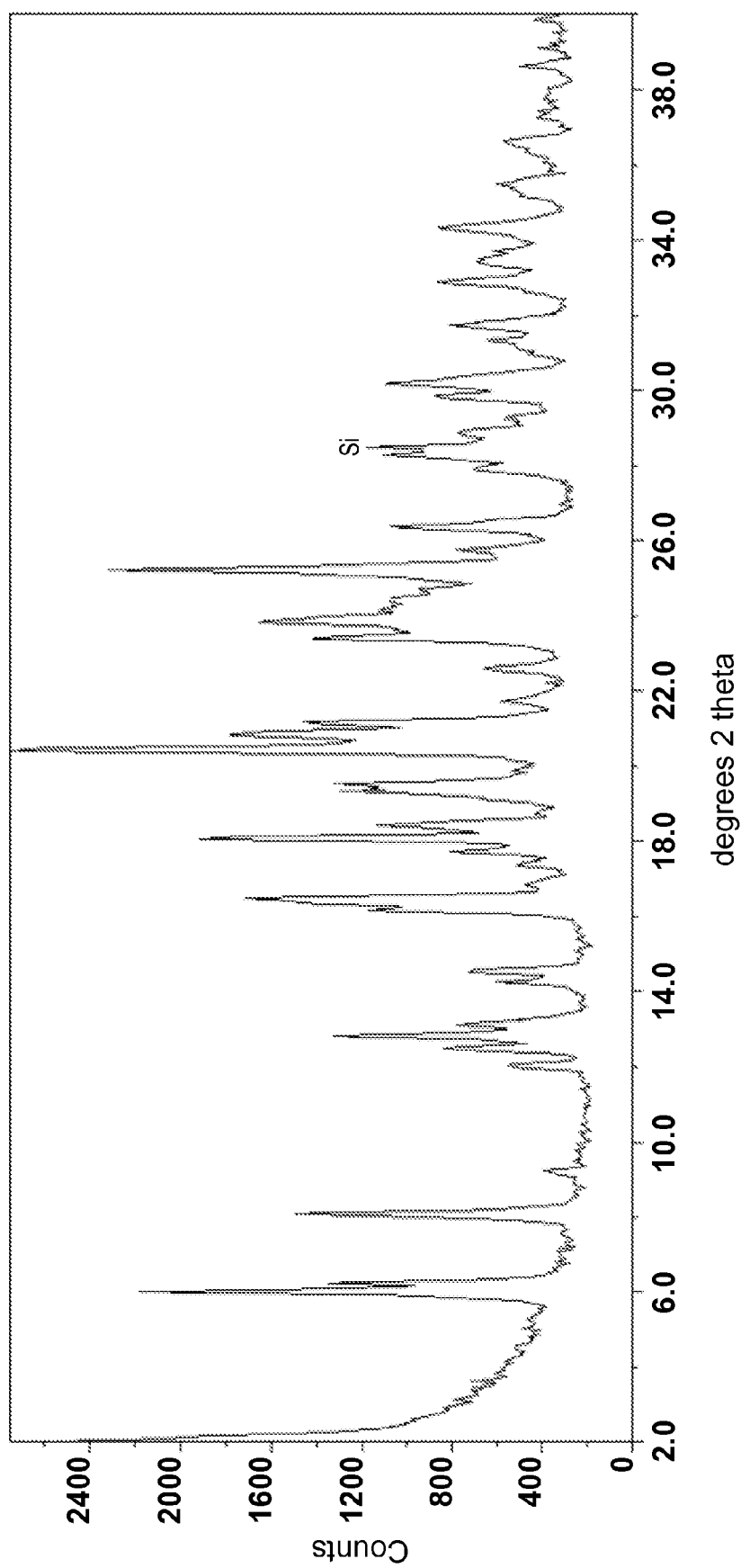
FIG. 4f shows a powder XRD pattern of crystalline Form I1. The peak at 28.5° is attributed to silicon powder.

In one embodiment, the present invention provides a crystalline Sitagliptin L-malate, designated Form I1, characterized by data selected from: a powder XRD pattern with peaks at 6.0°, 8.0°, 12.8°, 18.0° and 20.4°±0.2° 2θ; a powder XRD diffractogram shown in FIG. 4f; a solid-state $^{13}C$ NMR spectrum with signals at 121.7, 150.8 and 173.0±0.2 ppm; a solid-state $^{13}C$ NMR spectrum having chemical shifts differences between the signal exhibiting the lowest chemical shift and another in the chemical shift range of 100 to 190 ppm of 17.2, 46.3 and 68.5±0.1 ppm; and a $^{13}C$ NMR spectrum as depicted in FIGS. 4d and 4e; and combinations thereof. The signal exhibiting the lowest chemical shift in the chemical shift area of 100 to 180 ppm is typically at 104.5±1 ppm.

Form I1 can be also characterized by a powder XRD pattern with peaks at 6.1°, 8.2°, 13.0°, 18.1° and 20.5°±0.2° 2θ.

Form I1 can be also characterized by a powder XRD pattern with peaks at 6.0°, 8.0°, 12.0°, 12.8°, 14.5°, 16.3°, 18.0°, 19.4°, 20.4° and 21.1°±0.2° 2θ.

Form I1 can be also characterized by a powder XRD pattern with peaks at 6.1°, 8.2°, 12.1°, 13.0°, 14.6°, 16.4°, 18.1°, 19.5°, 20.5° and 21.2°±0.2° 2θ.

Sitagliptin L-malate Form I1 preferably has advantageous properties selected from at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

Form I1 can be prepared by a process comprising forming a solution of Sitagliptin base in acetonitrile; combining the solution with L-malic acid to form a precipitate; and isolating the obtained precipitate. The obtained precipitate can be further dried. Preferably, the sulfuric acid is used at a mol ratio of about 1:1 of Sitagliptin base to L-malic acid.

The present invention relates to crystalline form of Sitagliptin quinate, referred herein as Form Q1.

Figure 6A:
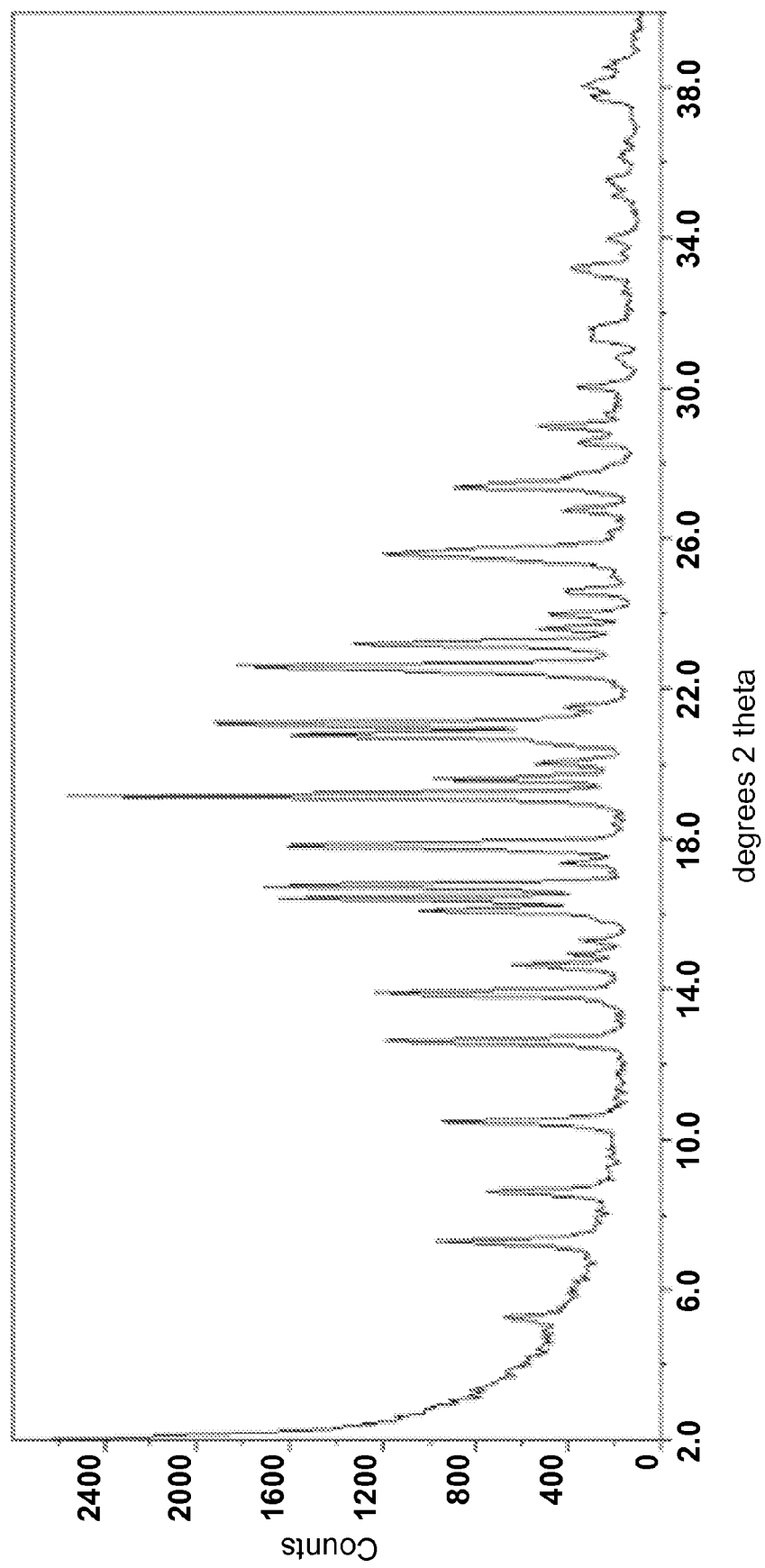
FIG. 6a shows a powder XRD pattern of crystalline Form Q1 of Sitagliptin quinate.
Figure 6B:
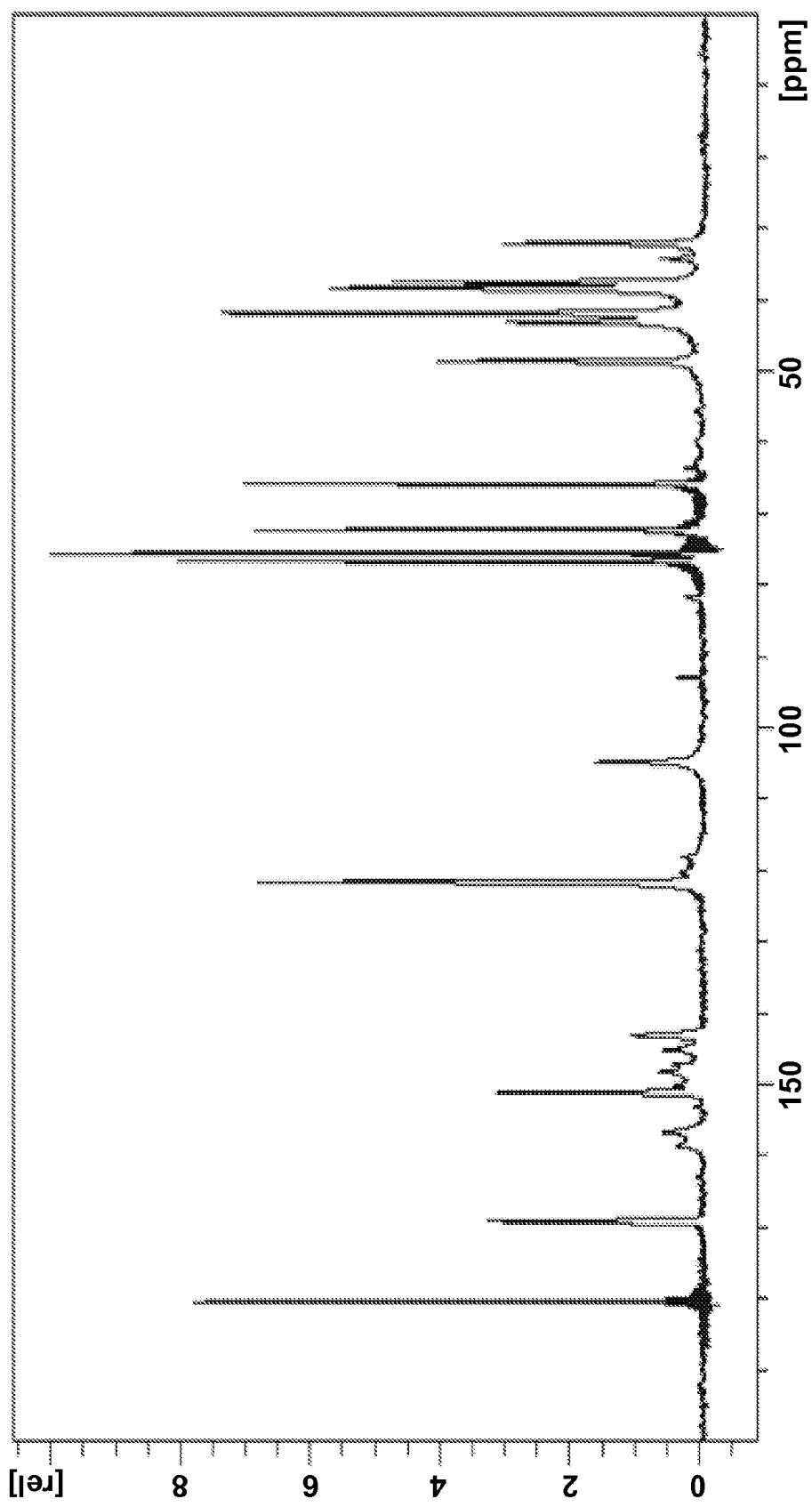
FIG. 6b shows a solid state $^{13}$C NMR spectrum of Sitagliptin quinate Form Q1 in the 0-200 ppm range.
Figure 6C:
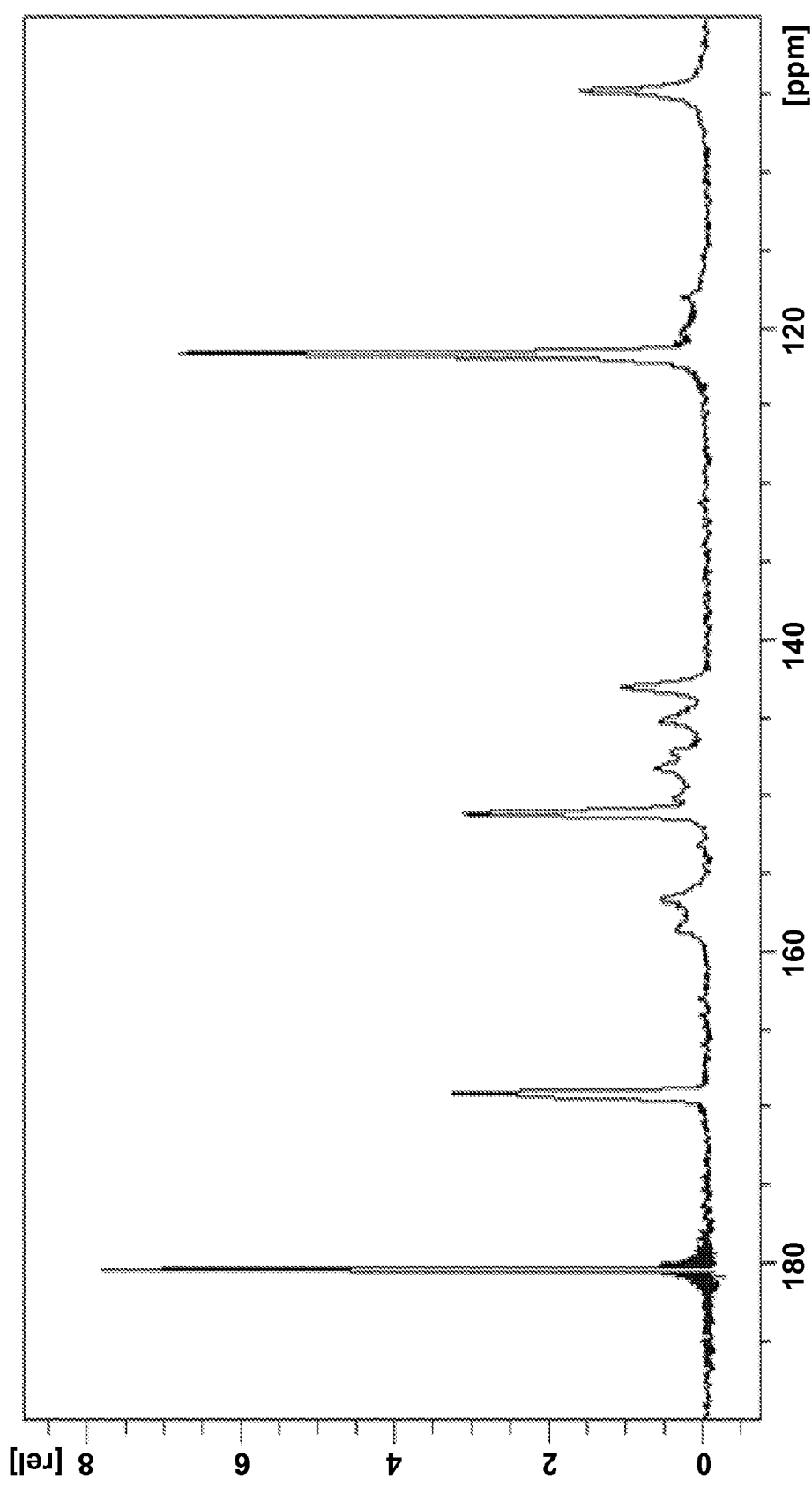
FIG. 6c shows a solid state $^{13}$C NMR spectrum of Sitagliptin quinate Form Q1 in the 100-190 ppm range.

In one embodiment, the present invention provides a crystalline Sitagliptin quinate, designated Form Q1, characterized by data selected from: a powder XRD pattern with peaks at 7.3°, 8.6°, 10.5°, 12.6° and 13.9°±0.2° 2θ; a powder XRD pattern as shown in FIG. 6a; a solid-state $^{13}C$ NMR spectrum with signals at 121.5, 169.0 and 180.3±0.2 ppm; a solid-state $^{13}C$ NMR spectrum having chemical shifts differences between the signal exhibiting the lowest chemical shift and another in the chemical shift range of 100 to 190 ppm of 16.8, 64.3 and 75.6±0.1 ppm; and a $^{13}C$ NMR spectrum is depicted in FIGS. 6b and 6c; and combinations thereof. The signal exhibiting the lowest chemical shift in the chemical shift area of 100 to 190 ppm is typically at 104.7±1 ppm.

Sitagliptin quinate Form Q1 can be also characterized by a powder XRD pattern with peaks at 7.3°, 8.6°, 10.5°, 12.6°, 13.9°, 16.1°, 16.4°, 16.8°, 17.8° and 19.2°±0.2° 2θ.

Sitagliptin quinate Form Q1 can be prepared by a process comprising forming a solution of Sitagliptin base in an organic solvent selected from acetonitrile, and isopropanol; and adding (1R,3R,4R,5R)-(−)-quinic acid to the solution to obtain Form Q1. Preferably, the (1R,3R,4R,5R)-(−)-quinic acid is used at a mol ratio of about 1:1 of Sitagliptin base to (1R,3R,4R,5R)-(−)-quinic acid.

After the addition of the acid, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Sitagliptin acetate Form Q1 preferably has advantageous properties selected from at least one of: good crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

The present invention provides additional Sitagliptin salts solid state forms.

Hereinafter, is described a crystalline Sitagliptin sulfate, designated Form S3, characterized by data selected from: a powder XRD pattern with peaks at 7.4°, 16.1°, 18.3° and 24.9°±0.2° 2θ; a powder XRD pattern as shown in FIG. 1c; a solid-state $^{13}$C NMR spectrum with signals at 119.9, 152.0 and 169.5±0.2 ppm; a solid-state $^{13}$C NMR spectrum having chemical shifts differences between the signal exhibiting the lowest chemical shift and another in the chemical shift range of 100 to 200 ppm of 16.7, 48.8 and 66.3±0.1 ppm; $^{13}$C NMR spectrum is depicted in FIGS. 1o and 1p; and combinations thereof. The signal exhibiting the lowest chemical shift in the chemical shift area of 100 to 200 ppm is typically at 103.2±1 ppm.

Sitagliptin sulfate Form S3 can be also characterized by a powder XRD pattern with peaks at 4.8°, 5.7°, 7.4°, 13.5°, 14.3°, 15.0°, 16.1°, 18.3°, 22.8° and 24.9°±0.2° 2θ.

Sitagliptin sulfate crystalline Form S3 can be prepared by a process comprising forming a solution of Sitagliptin base in ethyl acetate; combining the solution with sulfuric acid to form a precipitate; and isolating the obtained precipitate. Preferably, the sulfuric acid is used at a mol ratio of about 1:0.5 of Sitagliptin base to sulfuric acid.

Hereinafter, is described a crystalline Sitagliptin sulfate, designated Form S4, characterized by data selected from: a powder XRD pattern with peaks at 5.3°, 7.8°, 16.7°, 19.4° and 21.6°±0.2° 2θ; a powder XRD pattern as shown in FIG. 1d; and combinations thereof.

Sitagliptin sulfate Form S4 can be also characterized by a powder XRD pattern with peaks at 5.3°, 5.9°, 11.7°, 12.4°, 15.7°, 16.7°, 17.3°, 18.8°, 19.3°, 21.2° and 21.6°±0.2° 2θ.

Sitagliptin sulfate Form S4 can be also characterized by a powder XRD pattern with peaks at 5.3°, 5.9°, 7.8°, 11.7°, 12.4°, 15.7°, 16.7°, 17.3°, 18.8°, 19.3°, 21.2° and 21.6°±0.2° 2θ.

Sitagliptin sulfate crystalline Form S4 can be prepared by a process comprising forming a mixture of Sitagliptin base in ethanol; combining the mixture with sulfuric acid to form a precipitate; and isolating the obtained precipitate. Preferably, the sulfuric acid is used at a mol ratio of about 1:0.5 of Sitagliptin base to sulfuric acid, respectively.

Hereinafter, is described a crystalline Sitagliptin sulfate, designated Form S5, characterized by data selected from: a powder XRD pattern with peaks at 4.8°, 13.6°, 14.3°, 15.5° and 18.2°±0.2° 2θ; a powder XRD diffractogram shown in FIG. 1e; and combinations thereof.

Alternatively, Form S5 can be characterized by a powder XRD pattern with peaks at 4.8°, 13.6°, 14.3°, 15.5°, 18.2°, 19.0°, 19.4°, 22.1°, 23.4° and 24.5°±0.2° 2θ.

Hereinafter, is described a crystalline Sitagliptin sulfate, designated Form S8, characterized by data selected from: a powder XRD pattern with peaks at 5.8°, 9.7°, 15.4°, 19.1° and 20.8°±0.2° 2θ; a powder XRD diffractogram shown in FIG. 1k; and combinations thereof.

Alternatively, Form S8 can be characterized a powder XRD pattern with peaks at 4.8°, 5.8°, 9.7°, 11.9°, 13.7°, 15.4°, 17.6°, 19.1°, 20.8° and 22.0°±0.2° 2θ.

Figure 2A:
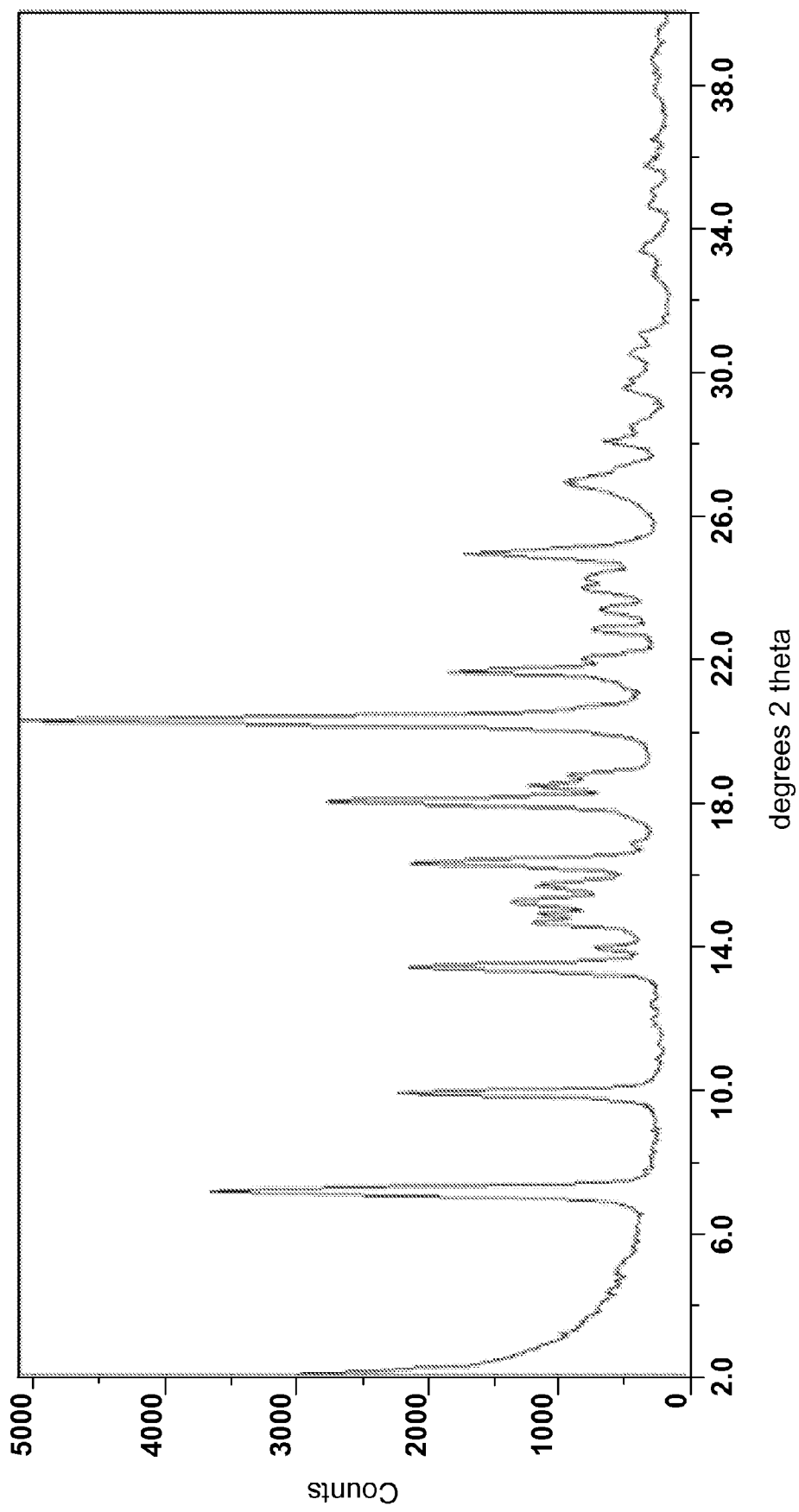
FIG. 2a shows a powder XRD pattern of crystalline Form D1 of Sitagliptin (+)-dibenzoyl-tartrate.

Hereinafter, is described a crystalline Sitagliptin (+)-dibenzoyl-tartrate, designated Form D1, characterized by data selected from: a powder XRD pattern with peaks at 7.1°, 9.9°, 13.4°, 16.3° and 18.0°±0.2° 2θ; a powder XRD pattern as shown in FIG. 2a; and combinations thereof.

Sitagliptin dibenzoyl-tartrate Form D1 can be also characterized by a powder XRD pattern with peaks at 7.1°, 9.9°, 13.4°, 15.2°, 16.3°, 18.0°, 18.4°, 20.3°, 21.6° and 24.9°±0.2° 2θ.

Sitagliptin (+)-dibenzoyl-tartrate Form D1 can be prepared by a process comprising forming a solution of Sitagliptin base in an organic solvent selected from acetonitrile, and ethyl acetate; and adding (+)-dibenzoyl-D-tartaric acid to the solution to obtain Form D1. Preferably, the (+)-dibenzoyl-D-tartaric acid is used at a mol ratio of about 1:1 of Sitagliptin base to (+)-dibenzoyl-D-tartaric acid.

After the addition of the acid, in this process or any process for the preparation of any of the Sitagliptin (+)-dibenzoyl-tartrate polymorphs disclosed herein, the obtained mixture can be heated to a temperature from about 40° C. to about 60° C., or from about 45° C. to about 55° C., for example about 50° C. Heating can be maintained for about 1 to about 10 hours, or from about 1 to about 4 hours, for example for about 2 hours. Afterward, the mixture can be cooled to a temperature from about 0° C. to about room temperature, or from about 10° C. to about room temperature, or about room temperature, for example, overnight, before collecting the obtained precipitate. The obtained precipitate can further be dried.

Figure 2B:
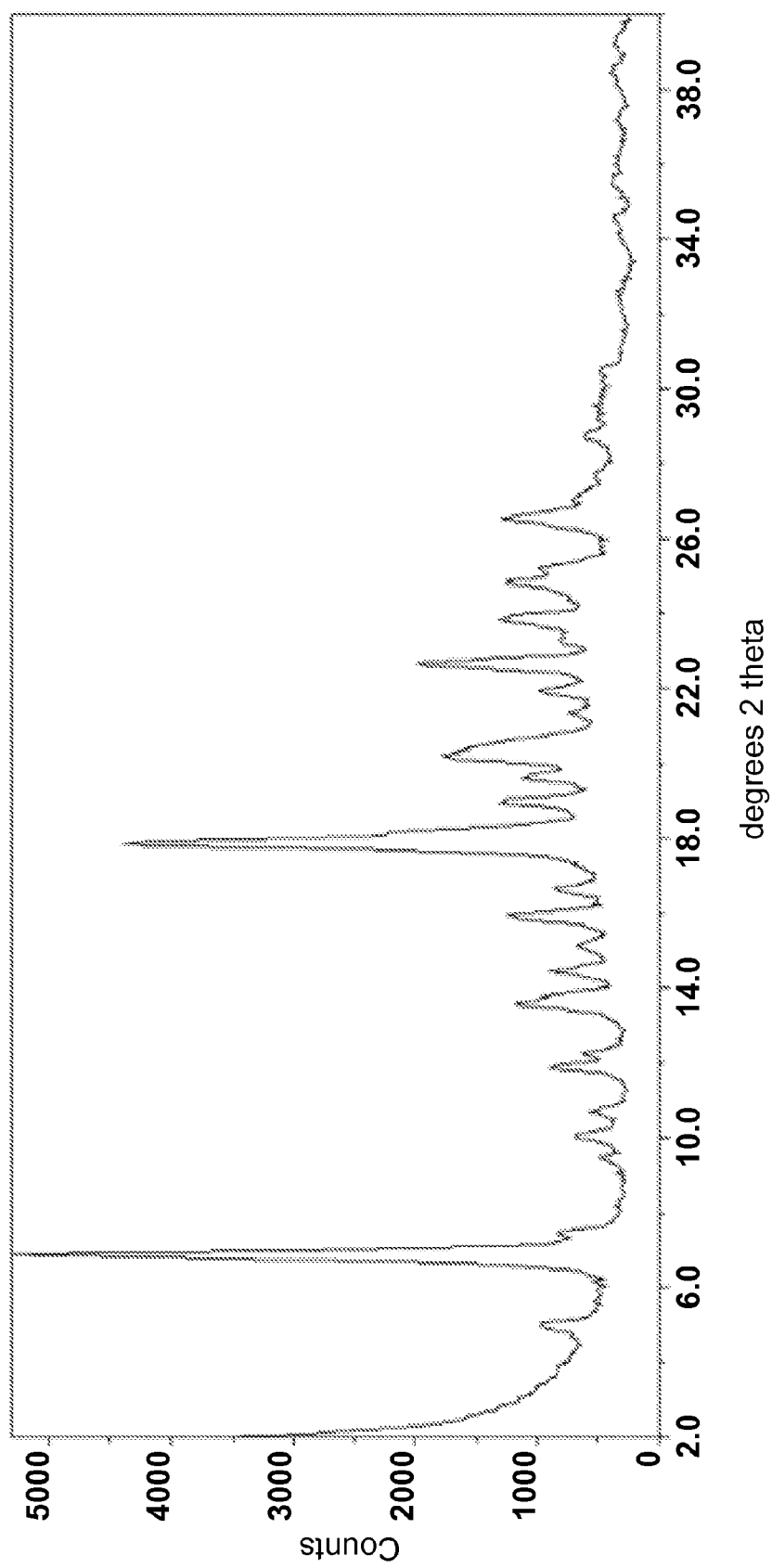
FIG. 2b shows a powder XRD pattern of crystalline Form D2 of Sitagliptin (+)-dibenzoyl-tartrate.

Hereinafter, is described a crystalline Sitagliptin (+)-dibenzoyl-tartrate, designated Form D2, characterized by data selected from: a powder XRD pattern with peaks at 6.9°, 11.9°, 15.9° and 17.9°±0.2° 2θ; a powder XRD pattern as shown in FIG. 2b; and combinations thereof.

Sitagliptin (+)-dibenzoyl-tartrate Form D2 can be also characterized by a powder XRD pattern with peaks at 5.0°, 6.9°, 10.7°, 11.9°, 14.5°, 15.9°, 17.9°, 19.0°, 22.6° and 23.8°±0.2° 2θ.

Sitagliptin (+)-dibenzoyl-tartrate Form D2 can be prepared by a process comprising forming a mixture (e.g. a solution or a slurry) of Sitagliptin base in ethanol; and adding (+)-dibenzoyl-D-tartaric acid to obtain Form D2. Preferably, the (+)-dibenzoyldibenzoyl-D-tartaric acid is used at a mol ratio of about 1:1 of Sitagliptin base to (+)-dibenzoyl-D-tartaric acid.

Figure 3A:
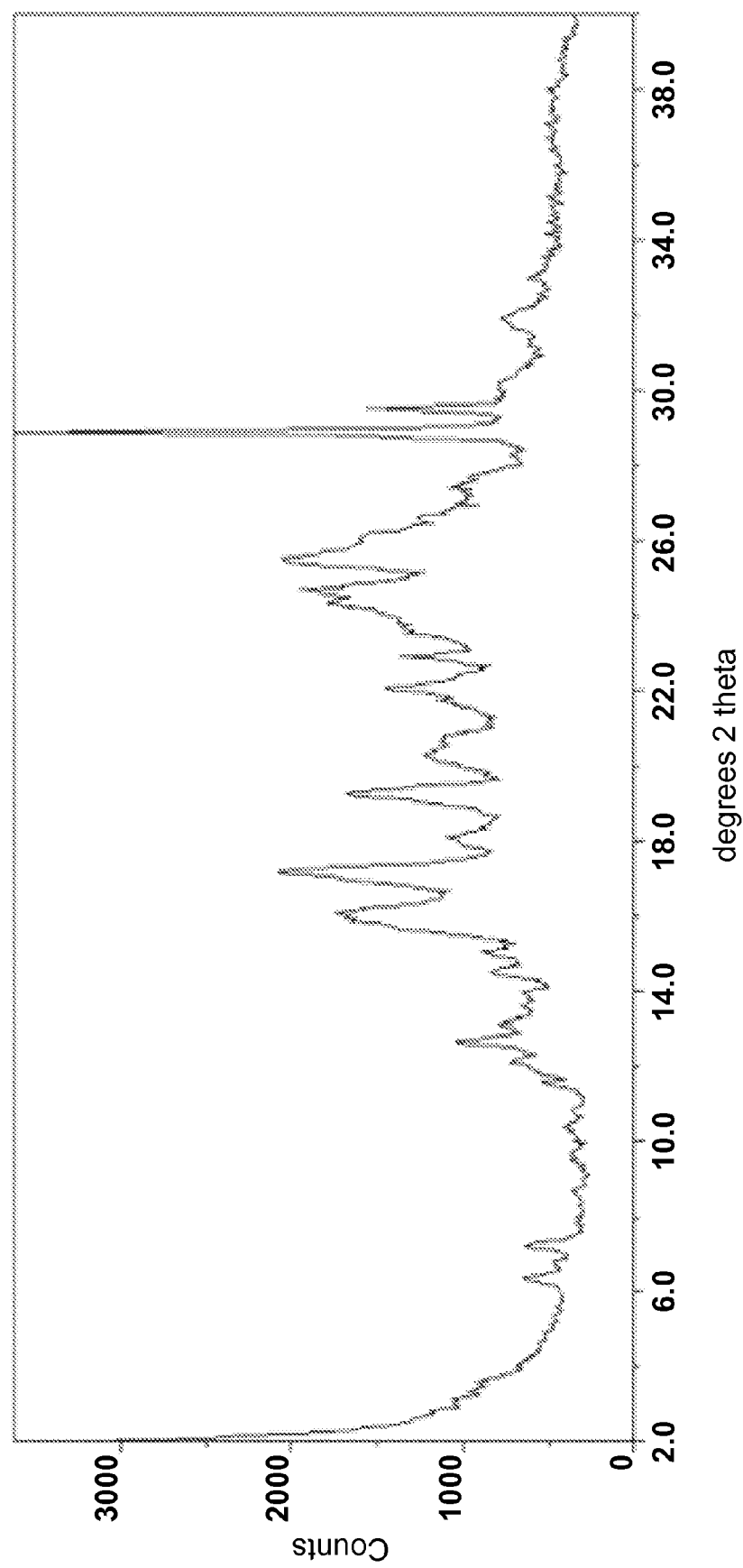
FIG. 3a shows a powder XRD pattern of crystalline Form F1 of Sitagliptin fumarate.

Hereinafter, is described a crystalline Sitagliptin fumarate, designated Form F1, characterized by data selected from: a powder XRD pattern with peaks at 6.3°, 7.2°, 12.6°, 14.5° and 15.0°±0.3° 2θ; a powder XRD pattern as shown in FIG. 3a; and combination thereof.

Sitagliptin fumarate Form F1 can be also characterized by a powder XRD pattern with peaks at 6.3°, 7.2°, 12.6°, 14.5°, 15.0°, 16.0°, 17.3°, 19.3° and 22.0°±0.3° 2θ.

Sitagliptin fumarate Form F1 can be prepared by a process comprising forming a solution of Sitagliptin base in an organic solvent selected from acetonitrile, and ethanol; and adding fumaric acid to the solution to obtain Form F1. Preferably, n-heptane is added as a co-solvent to induce precipitation. Preferably, the fumaric acid is used at a mol ratio of about 1:1 of Sitagliptin base to fumaric acid.

In this process, as well in the proceeding processes for the preparation of any of the crystalline form of Sitagliptin fumarate disclosed herein, after the addition of the acid, the obtained mixture can be heated to a temperature from about 40° C. to about 60° C., or from about 45° C. to about 55° C., for example about 50° C. The mixture can be heated for a time interval from about 1 to about 10 hours, or from about 1 to about 4 hours, for example, for about 2 hours. Afterward, the mixture can be cooled to a temperature from about 0° C. to about room temperature, or from about 10° C. to about room temperature, for example to about room temperature, for example overnight, before collecting the obtained precipitate. The obtained precipitate can further be dried.

Figure 3B:
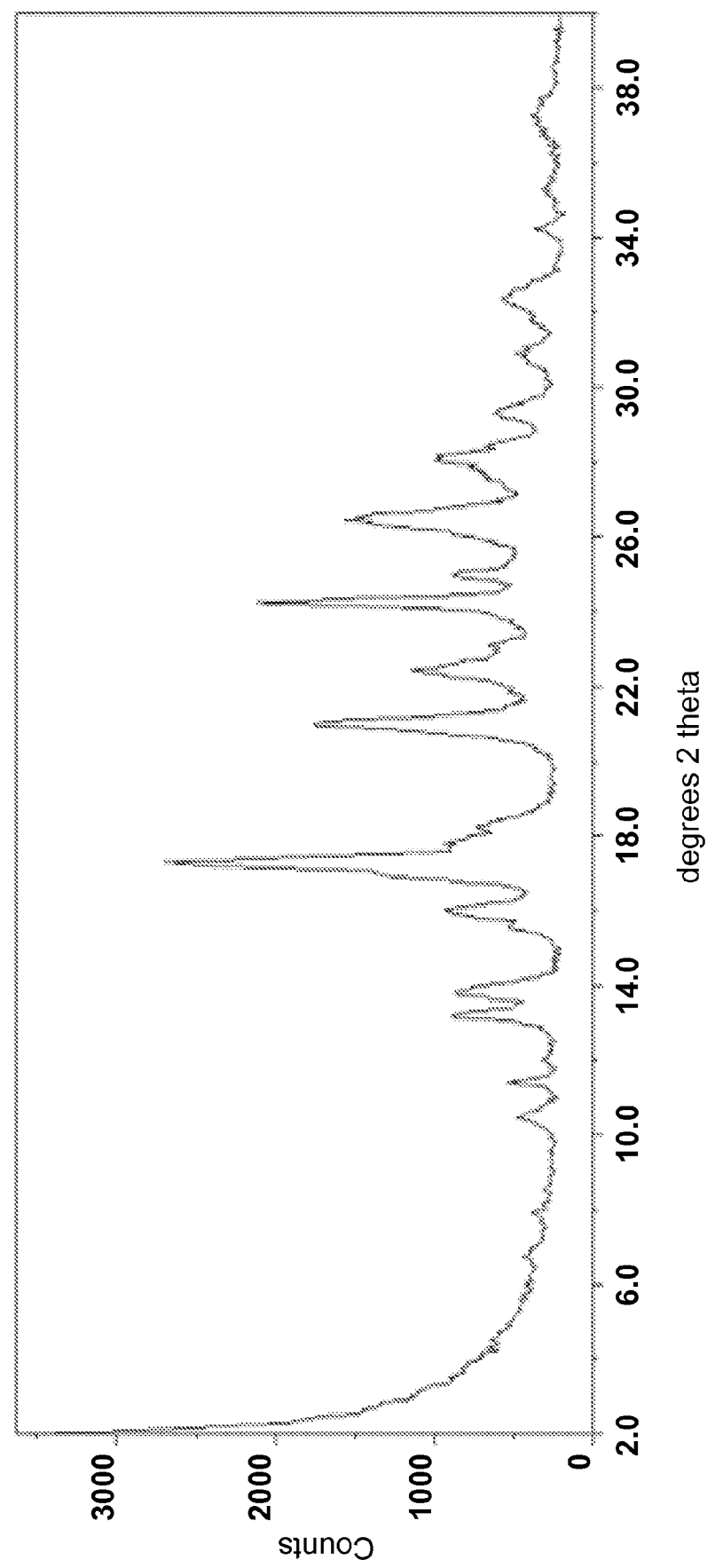
FIG. 3b shows a powder XRD pattern of crystalline Form F2 of Sitagliptin fumarate.
Figure 3C:
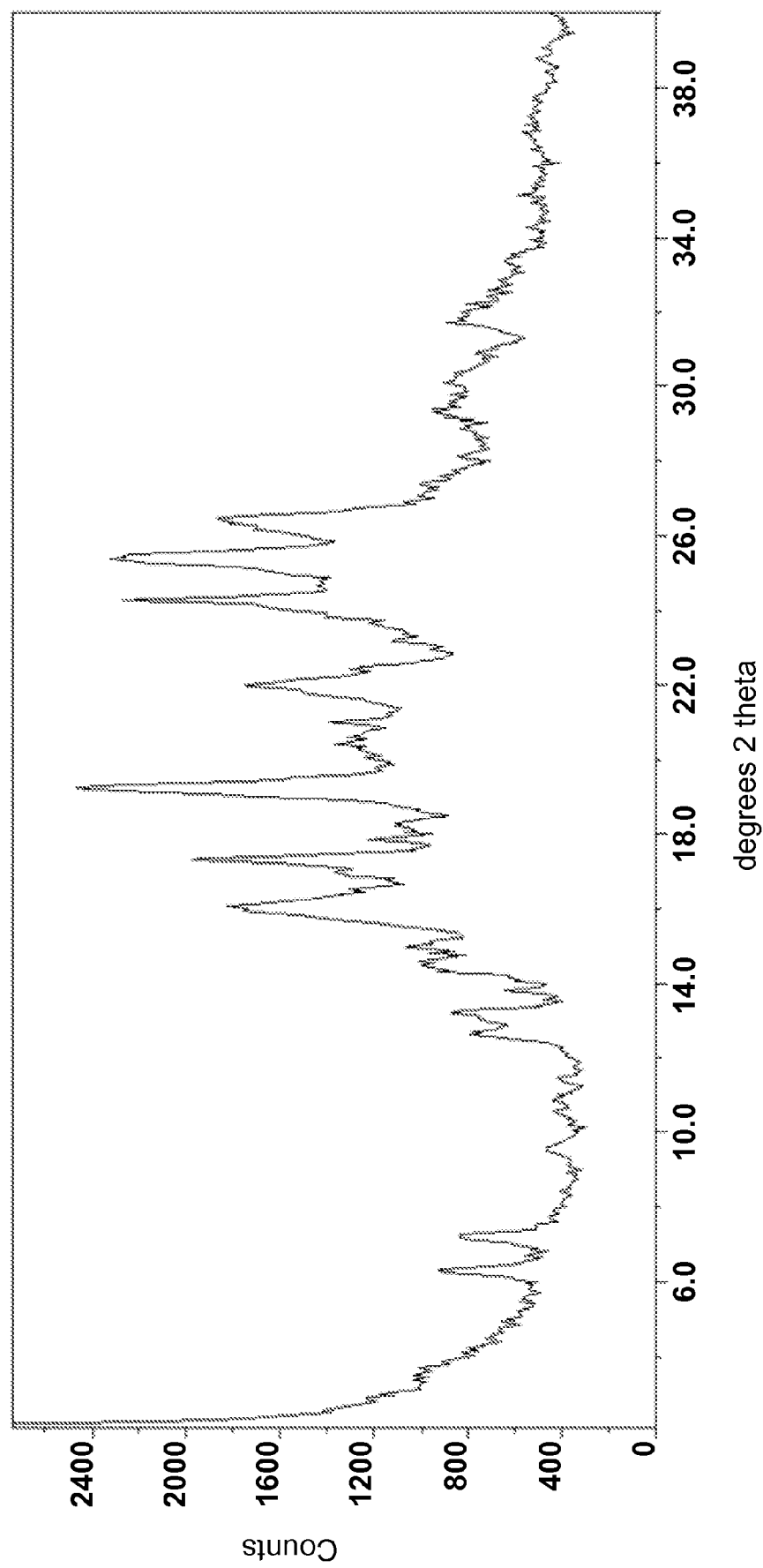
FIG. 3c shows a powder XRD pattern of crystalline Form F1 of Sitagliptin fumarate.

Hereinafter, is described a crystalline Sitagliptin fumarate, designated Form F2, characterized by data selected from: a powder XRD pattern with peaks at 10.5°, 11.4°, 13.2° and 13.8°±0.3° 2θ; a powder XRD pattern as shown in FIG. 3b; and combinations thereof.

Sitagliptin fumarate F2 is also characterized by a powder XRD pattern with peaks at 10.5°, 11.4°, 13.2°, 13.8°, 16.0°, 17.3°, 21.0°, and 25.0°±0.3° 2θ.

Sitagliptin fumarate Form F2 can be prepared by a process comprising forming a solution of Sitagliptin base in ethyl acetate; and adding fumaric acid to obtain Form F2. Preferably, the fumaric acid is used at a mol ratio of about 1:1 of Sitagliptin base to fumaric acid.

Figure 4G:
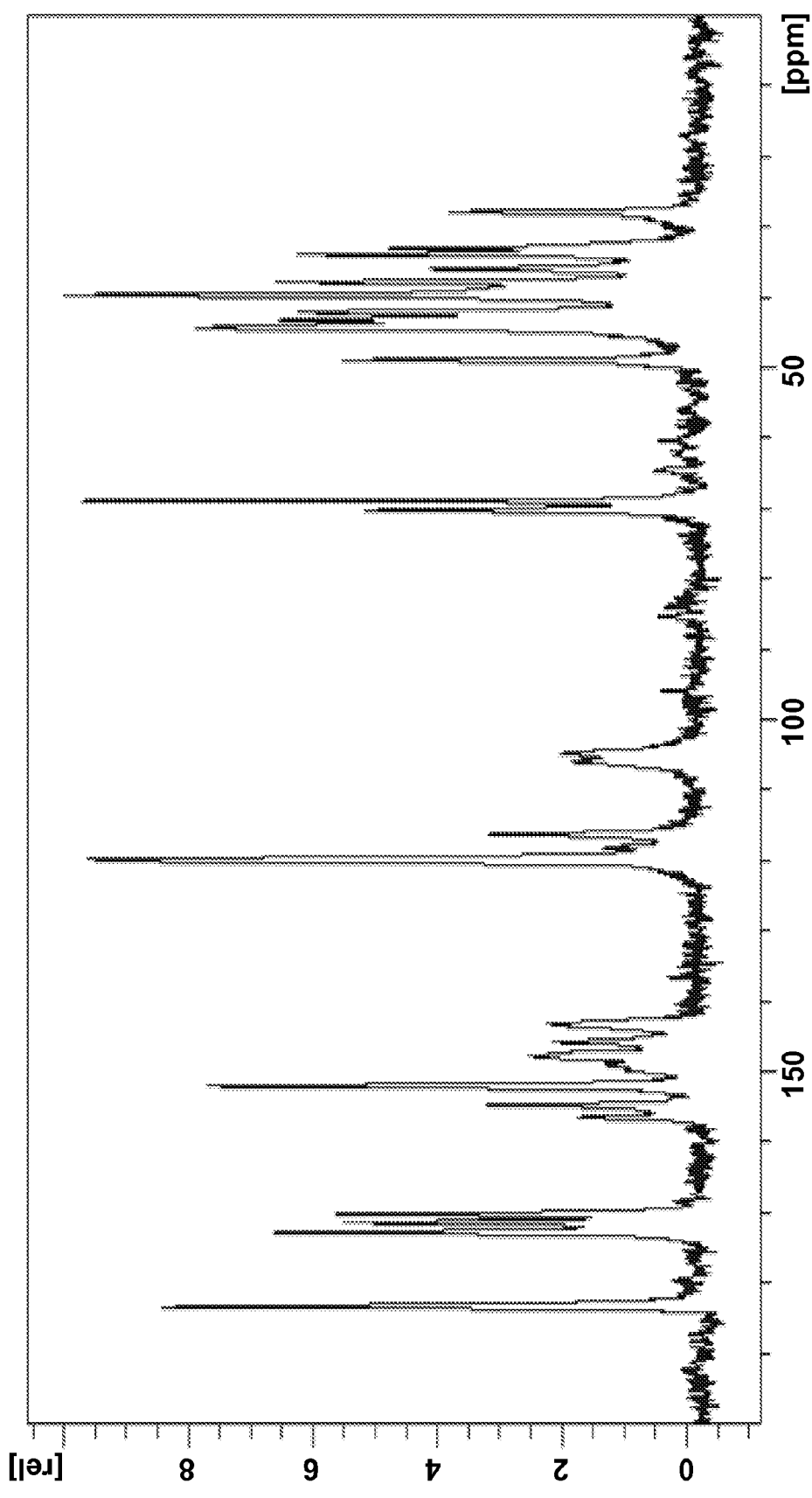
FIG. 4g shows a solid-state $^{13}$C NMR spectrum of Sitagliptin D-malate Form M1 in the 0-200 ppm range.
Figure 4H:
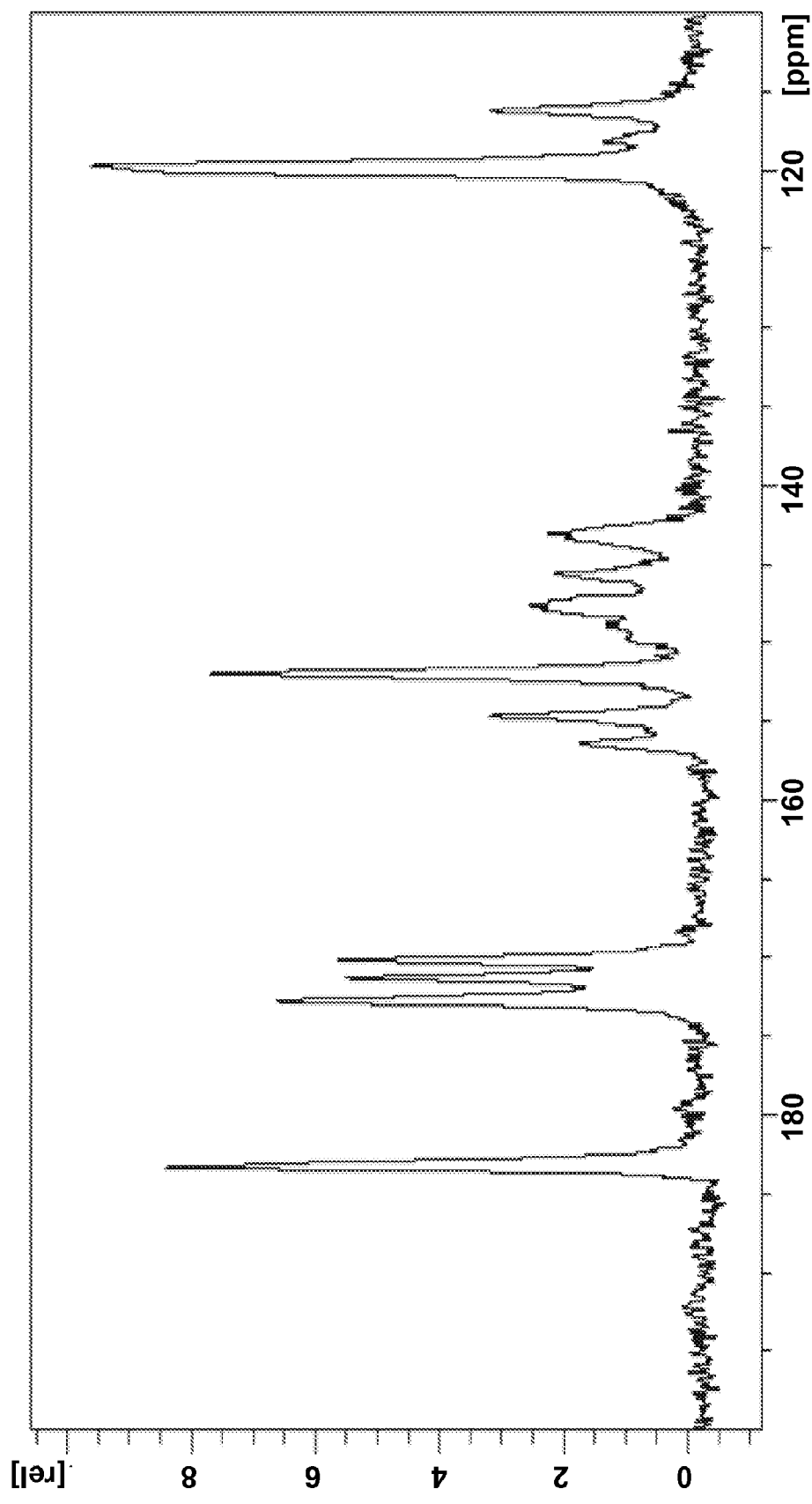
FIG. 4h shows a solid-state $^{13}$C NMR spectrum of Sitagliptin D-malate Form M1 in the 110-200 ppm range.

Hereinafter, is described a crystalline Sitagliptin (D)-(+)-malate, designated Form M1, characterized by data selected from: a powder XRD pattern with peaks at 13.1°, 14.1°, 15.7° and 19.6°±0.2° 2θ; a powder XRD pattern as shown in FIG. 4a; a solid-state $^{13}C$ NMR spectrum with signals at 119.7, 151.9 and 183.3±0.2 ppm; a solid-state $^{13}C$ NMR spectrum having chemical shifts differences between the signal exhibiting the lowest chemical shift and another in the chemical shift range of 110 to 200 ppm of 3.6, 35.8 and 67.2±0.1 ppm; $^{13}C$ NMR spectrum as shown in FIGS. 4g and 4h; and combinations thereof. The signal exhibiting the lowest chemical shift in the chemical shift area of 110 to 200 ppm is typically at 116.1±1 ppm.

Sitagliptin (D)-(+)-malate Form M1 can be also characterized by a powder XRD pattern with peaks at 10.7°, 13.1°, 14.1°, 15.7°, 17.3°, 17.9°, 19.6°, 20.8° and 21.6°±0.2° 2θ.

Sitagliptin (D)-(+)-malate Form M1 can be prepared by a process comprising forming a solution of Sitagliptin base in acetonitrile; and adding D-(+)-malic acid to the solution to obtain Form M1. Preferably, the D-(+)-malic acid is used at a mol ratio of about 1:1 of Sitagliptin base to D-(+)-malic acid.

After the addition of the acid, in any of the processes for preparing any of the crystalline Sitagliptin malate forms disclosed herein, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Hereinafter, is described a crystalline Sitagliptin (D)-(+)-malate, designated Form M2. Sitagliptin malate Form M2 is characterized by the XRD diffractogram shown in FIG. 4b.

Sitagliptin (D)-(+)-malate Form M2 can be prepared by a process comprising forming a solution of Sitagliptin base in ethanol; and adding D-(+)-malic acid to the solution to obtain Form M2. Preferably, the D-(+)-malic acid is used at a mol ratio of about 1:1 of Sitagliptin base to D-(+)-malic acid.

Figure 5A:
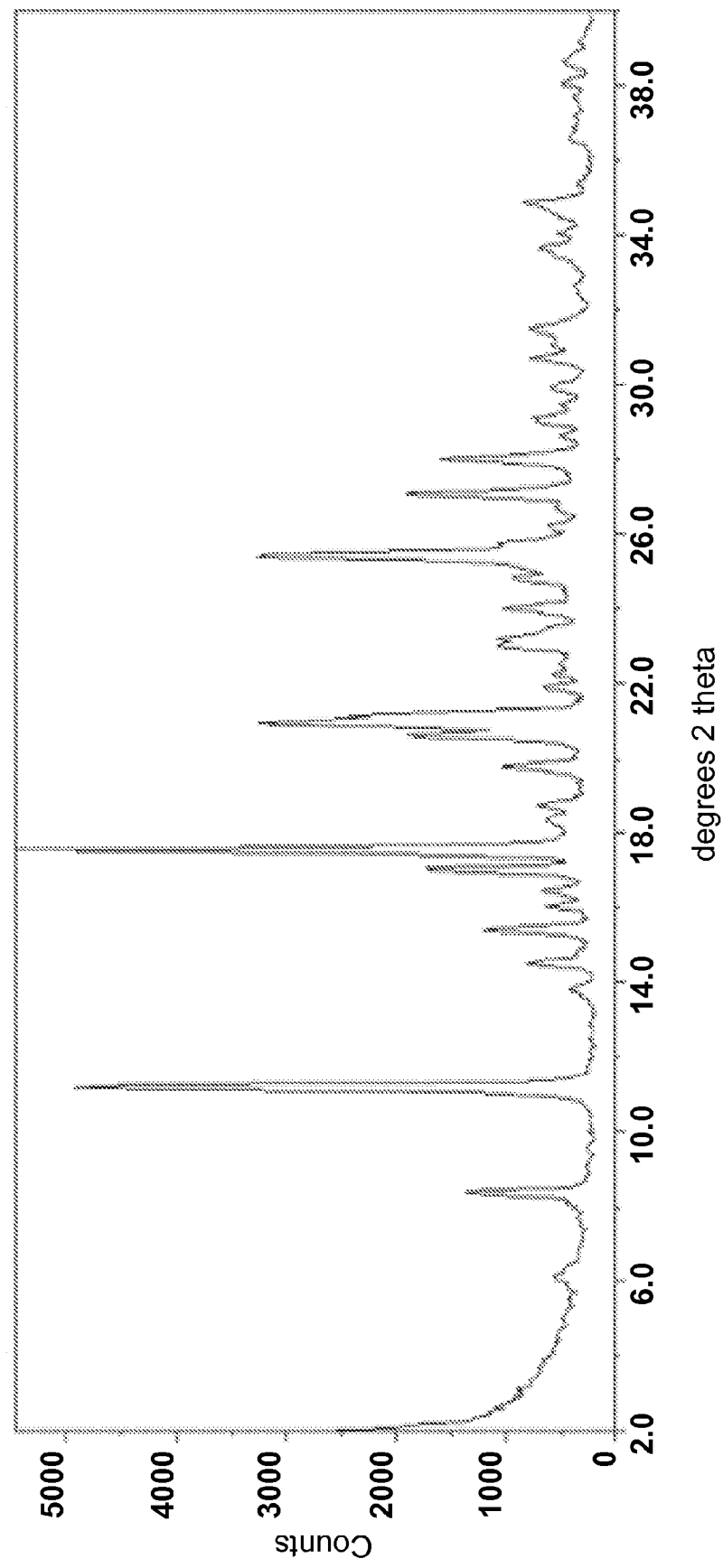
FIG. 5a shows a powder XRD pattern of crystalline Form O1 of Sitagliptin oxalate.

Hereinafter, is described a crystalline Sitagliptin oxalate, designated Form O1, characterized by data selected from: a powder XRD pattern with peaks at 8.4°, 11.2°, 14.5°, 17.0° and 17.6°±0.2° 2θ; a powder XRD pattern as shown in FIG. 5a; and combinations thereof.

Sitagliptin oxalate Form O1 can be also characterized by a powder XRD pattern with peaks at 8.4°, 11.2°, 14.5°, 15.4°, 17.0°, 17.6°, 19.8°, 21.0°, 25.4° and 27.1°±0.2° 2θ.

Sitagliptin oxalate Form O1 can be prepared by a process comprising forming a solution of Sitagliptin base in acetonitrile, or alternatively, forming a slurry in isopropanol; and adding oxalic acid to the solution or slurry, respectively, to obtain Form O1. Preferably, the oxalic acid is used at a mol ratio of about 1:1 of Sitagliptin base to oxalic acid.

After the addition of the acid, in any of the processes for preparing any of the crystalline Sitagliptin oxalate forms disclosed herein, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Figure 5B:
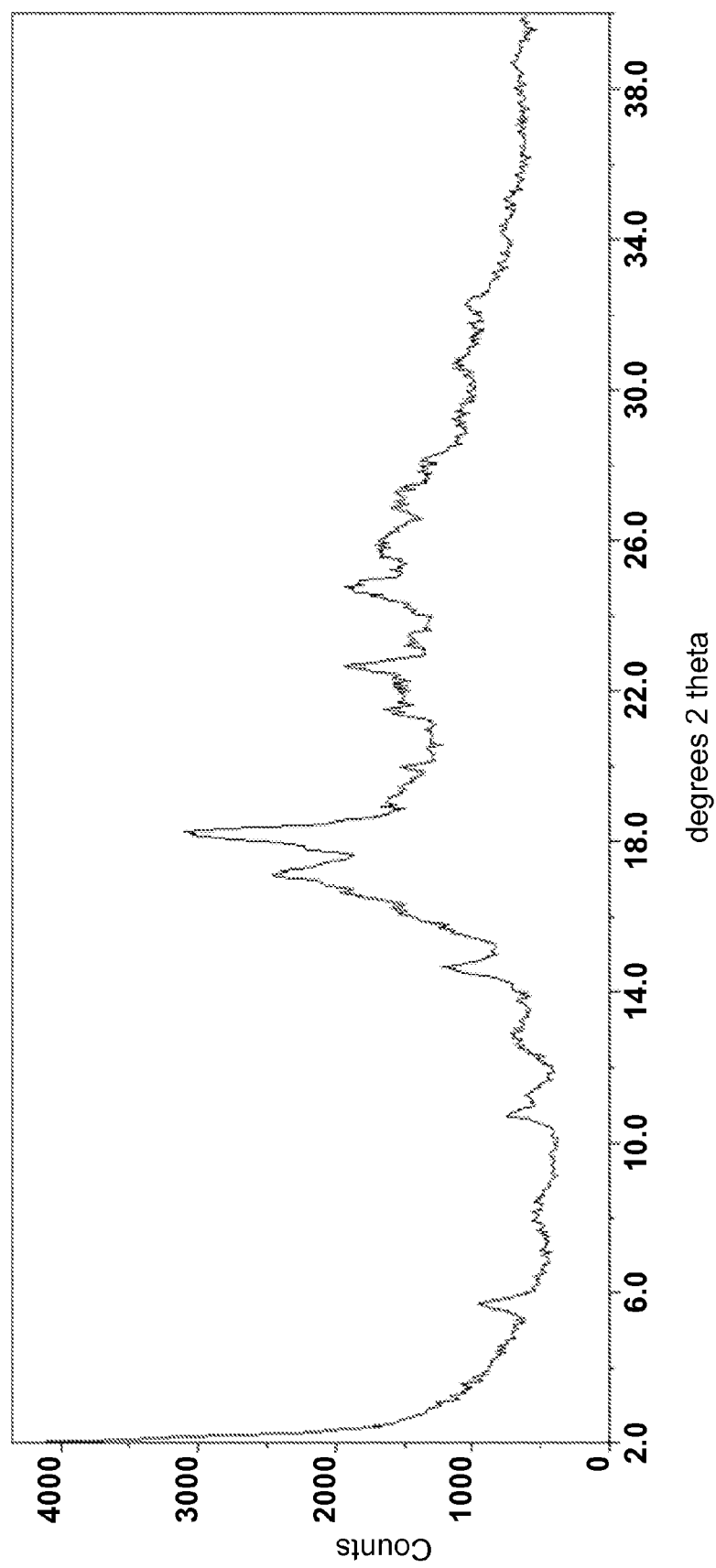
FIG. 5b shows a powder XRD pattern of crystalline Form O2 of Sitagliptin oxalate.

Hereinafter, is described a crystalline Sitagliptin oxalate, designated Form O2, characterized by data selected from: a powder XRD pattern with broad peaks at 5.7°, 10.7°, 14.7°, 17.1° and 18.2°±0.3° 2θ; a powder XRD pattern as shown in FIG. 5b; and combinations thereof.

Figure 5C:
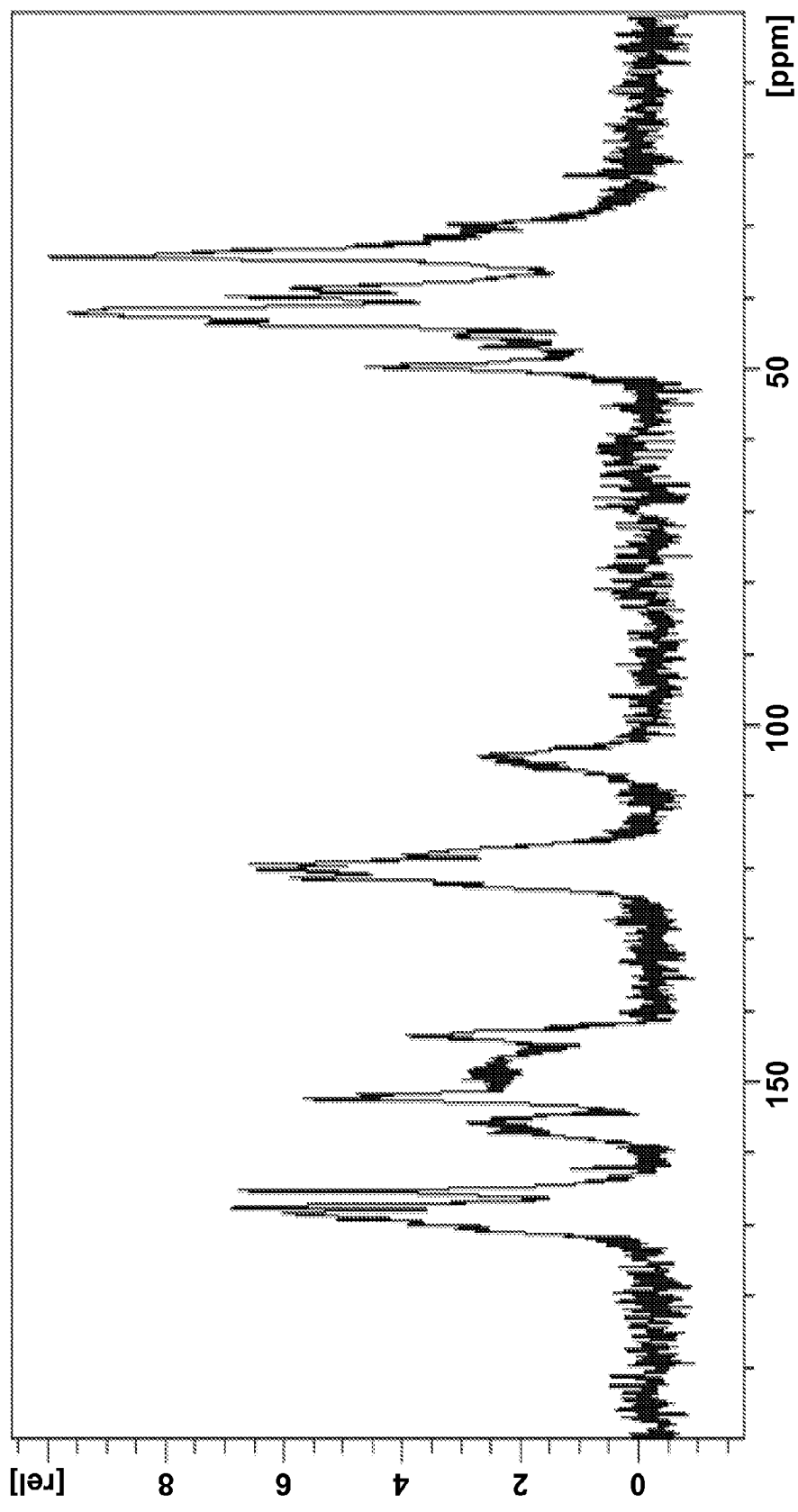
FIG. 5c shows a solid state $^{13}$C NMR spectrum of Sitagliptin oxalate Form O2 in the 0-200 ppm range.
Figure 5D:
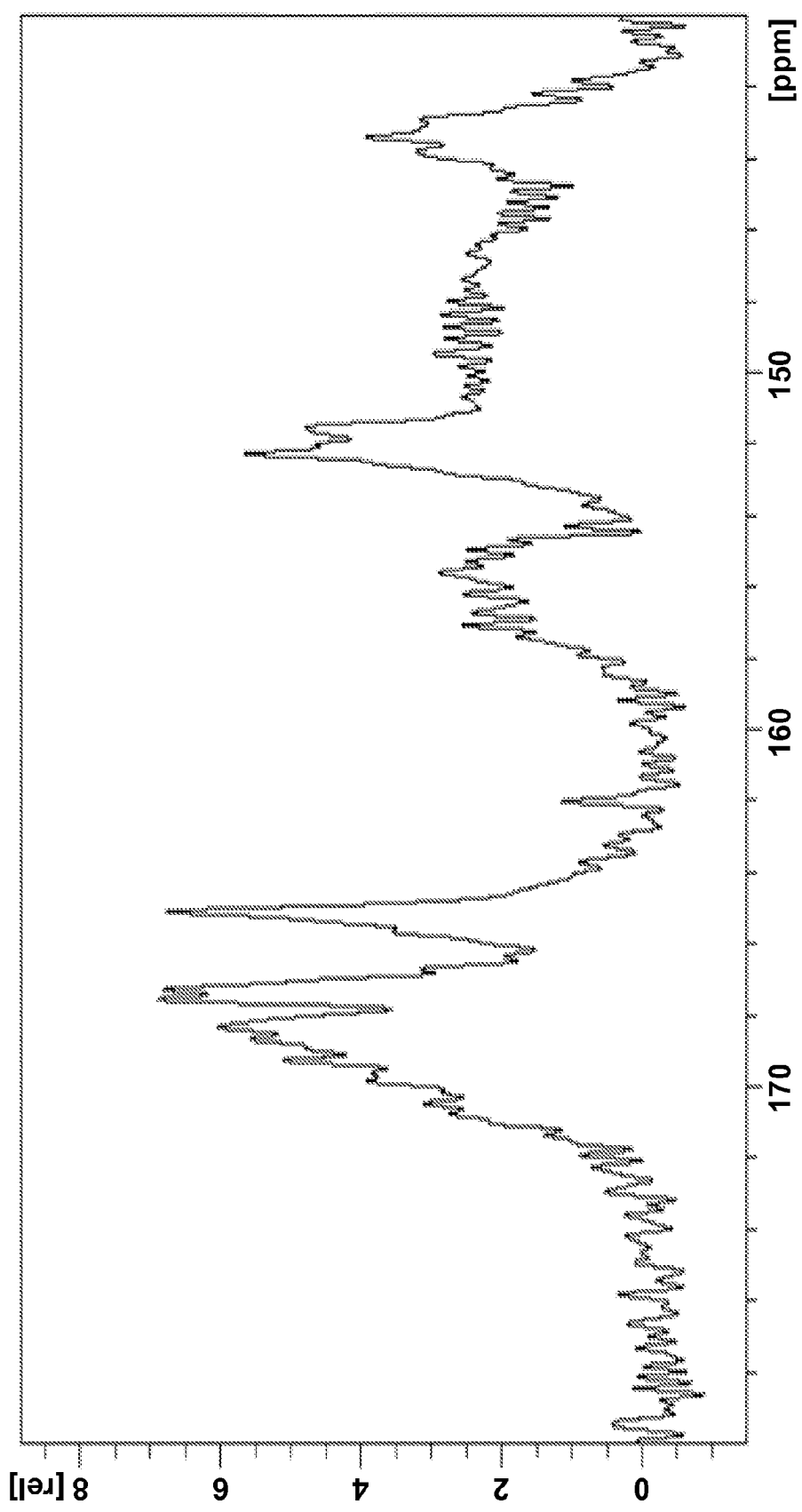
FIG. 5d shows a solid state $^{13}$C NMR spectrum of Sitagliptin oxalate Form O2 in the 140-180 ppm range.

Sitagliptin oxalate Form O2 can be also characterized by data selected from: a solid-state $^{13}C$ NMR spectrum with signals at 152.2, 165.1 and 167.5±0.2 ppm; a solid-state $^{13}C$ NMR spectrum having chemical shifts differences between the signal exhibiting the lowest chemical shift and another in the chemical shift range of 140 to 180 ppm of 8.8, 21.7 and 24.1±0.1 ppm; and a $^{13}C$ NMR spectrum as depicted in FIGS. 5c and 5d. The signal exhibiting the lowest chemical shift in the chemical shift area of 140 to 180 ppm is typically at 143.4±1 ppm.

Sitagliptin oxalate Form O2 can be prepared by a process comprising forming a solution of Sitagliptin base in ethyl acetate; and adding oxalic acid to the solution to obtain Form O2. Preferably, the oxalic acid is used at a mol ratio of about 1:1 of Sitagliptin base to oxalic acid.

Figure 7A:
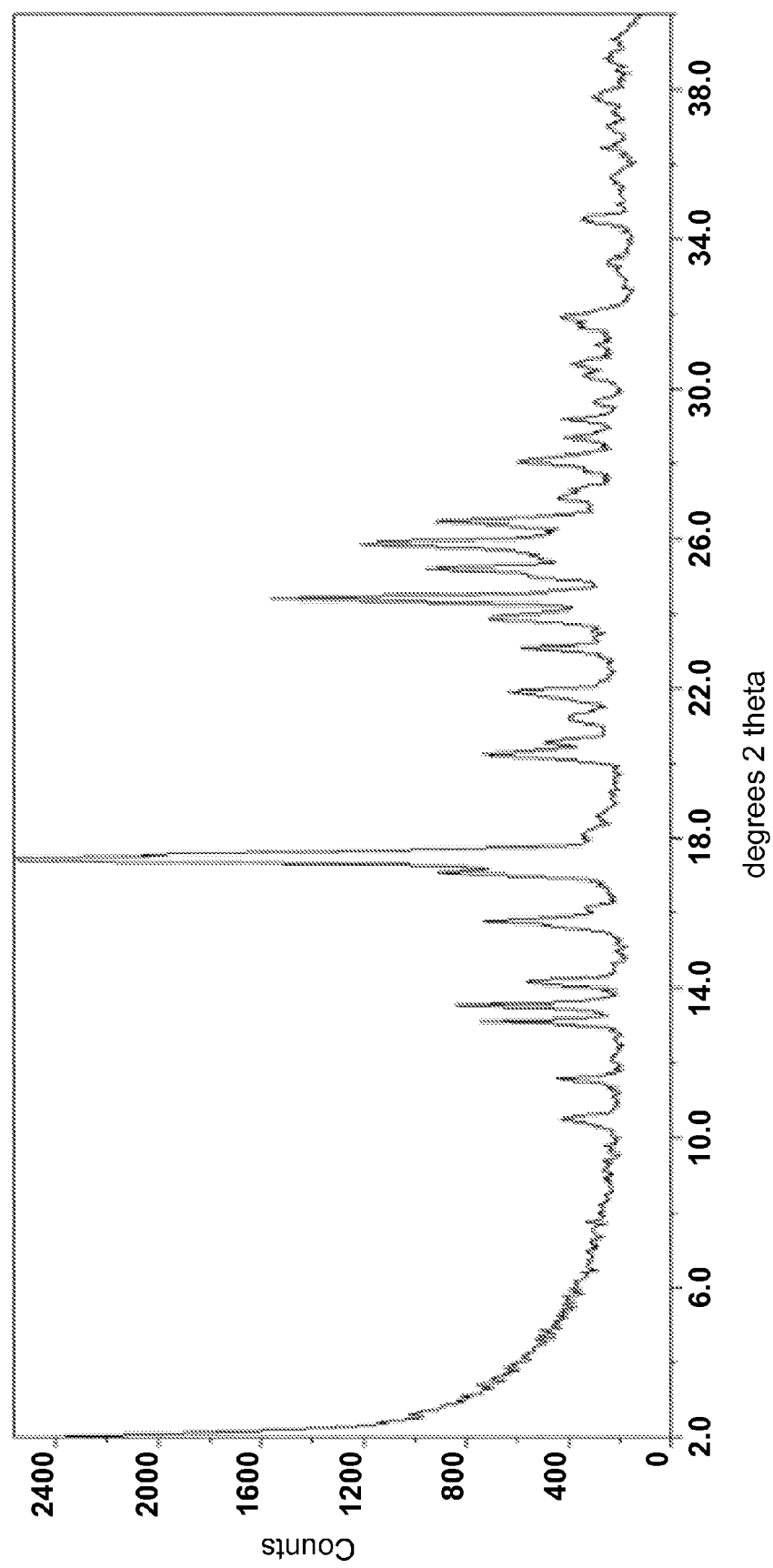
FIG. 7a shows a powder XRD pattern of crystalline Form U1 of Sitagliptin succinate.
Figure 7B:
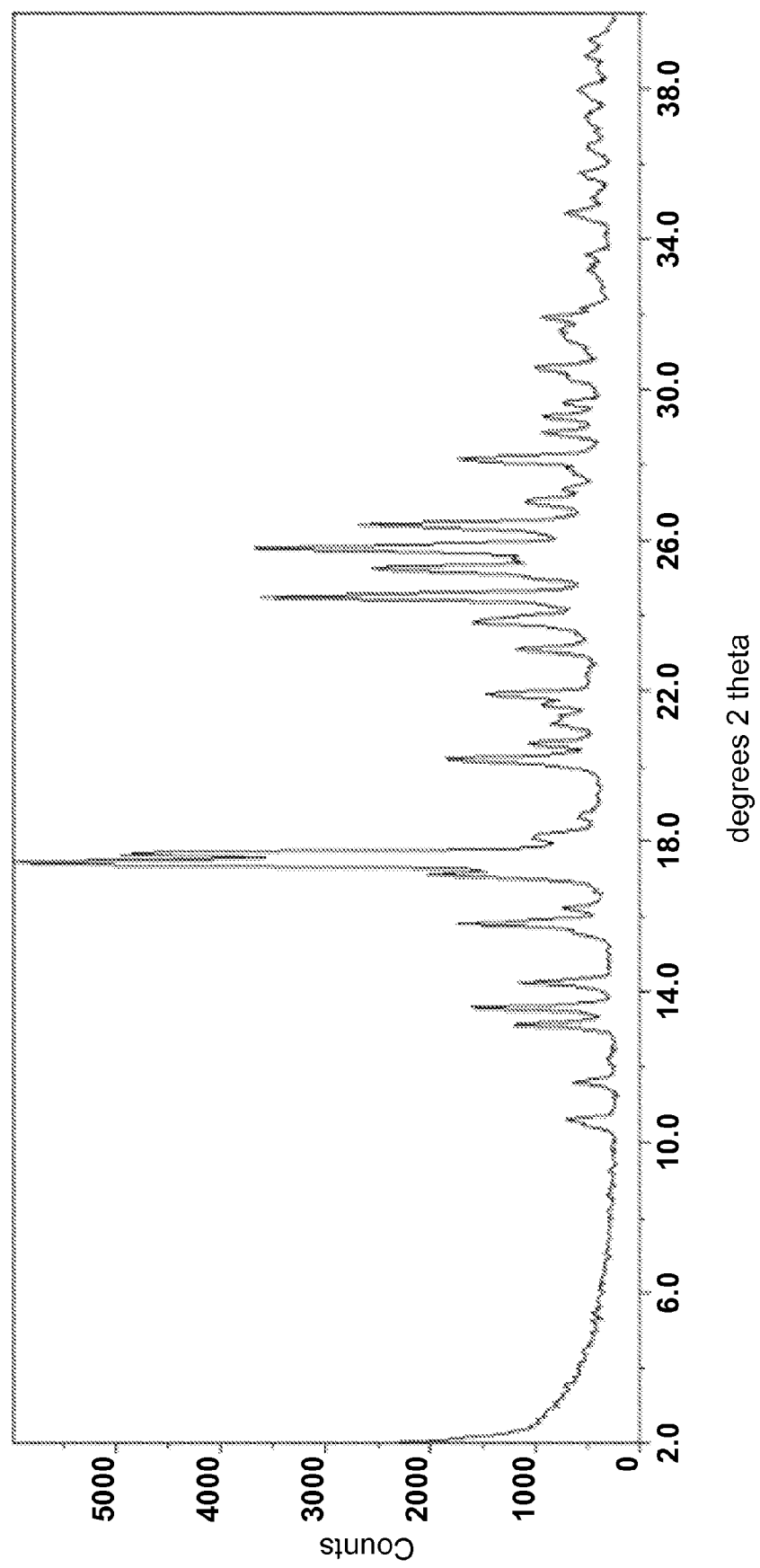
FIG. 7b shows a powder XRD pattern of crystalline Form U1 of Sitagliptin succinate.

Hereinafter, is described a crystalline Sitagliptin succinate, designated Form U1, characterized by data selected from: a powder XRD pattern with peaks at 11.6°, 13.1°, 13.6°, 14.2° and 15.8°±0.2° 2θ; a powder XRD pattern as shown in FIG. 7b; and combinations thereof.

Sitagliptin succinate Form U1 can be also characterized by a powder XRD pattern with peaks at 10.6°, 11.6°, 13.1°, 13.6°, 14.2°, 15.8°, 17.4°, 24.5°, 25.3° and 25.8°±0.2° 2θ.

Sitagliptin succinate Form U1 can be prepared by a process comprising forming a solution of Sitagliptin base in an organic solvent selected from ethanol, acetonitrile, and ethyl acetate; and adding succinic acid to obtain Form U1. Preferably, the succinic acid is used at a mol ratio of about 1:1 of Sitagliptin base to succinic acid.

After the addition of the acid, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Figure 10A:
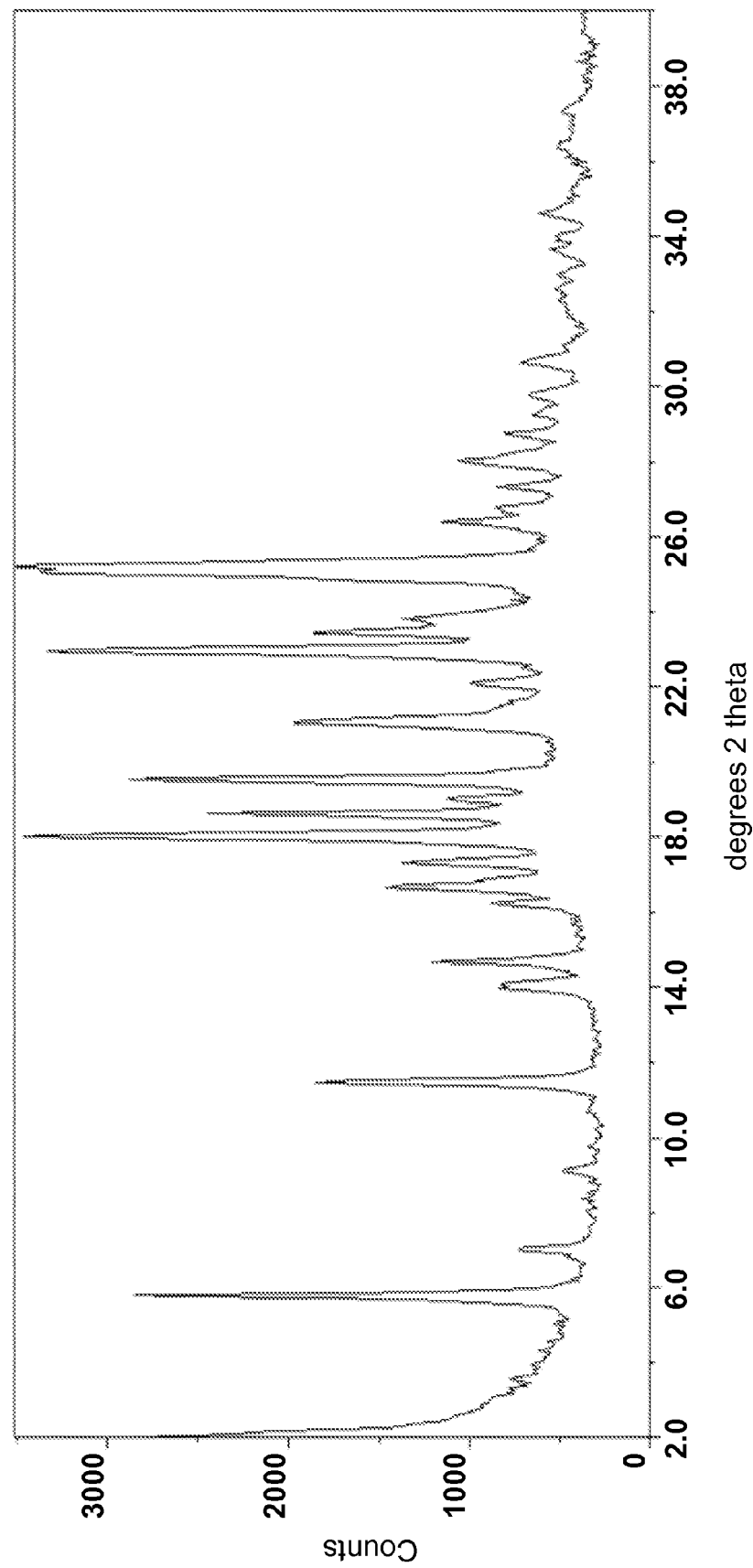
FIG. 10a shows a powder XRD pattern of crystalline Form A1 of Sitagliptin maleate.

Hereinafter, is described a crystalline Sitagliptin maleate, designated Form A1, characterized by data selected from: a powder XRD pattern with peaks at 5.8°, 11.5°, 14.7°, 16.7° and 18.0°±0.2° 2θ; a powder XRD pattern as shown in FIG. 10a; and combinations thereof.

Sitagliptin maleate Form A1 can be also characterized by a powder XRD pattern with peaks at 5.8°, 11.5°, 14.7°, 16.7°, 17.3°, 18.0°, 18.6°, 19.5°, 21.0° and 22.9°±0.2° 2θ.

Sitagliptin maleate crystalline Form A1 can be prepared by a process comprising forming a solution of Sitagliptin base in ethanol; combining the solution with maleic acid; adding n-heptane to form a precipitate; and isolating the obtained precipitate. Preferably, the maleic acid is used at a mol ratio of about 1:1 of Sitagliptin base to maleic acid.

After the addition of the acid, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to about 0° C. to about room temperature, or from about 10° C. to about room temperature, for example about room temperature, preferably overnight, before collecting the obtained precipitate. The obtained precipitate can be further dried.

Figure 11A:
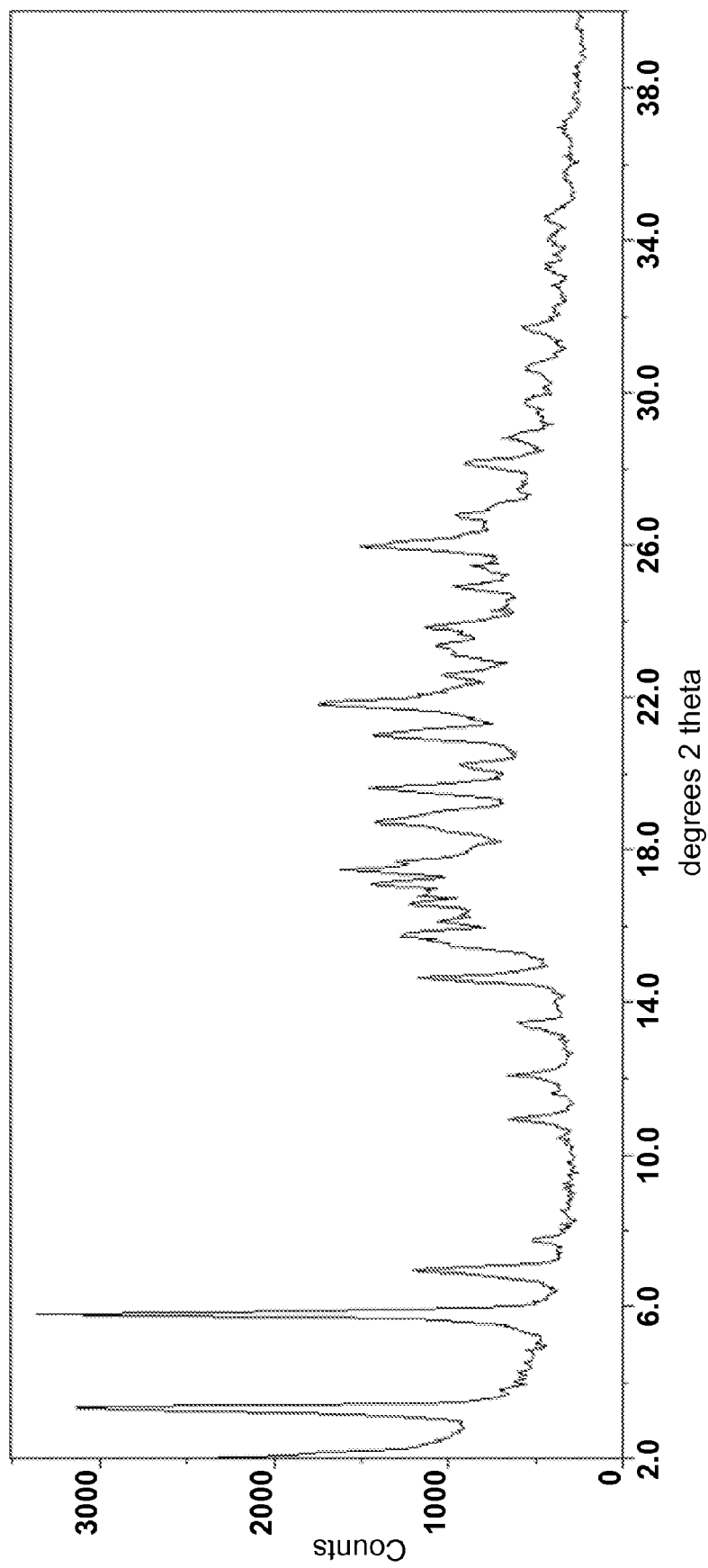
FIG. 11a shows a powder XRD pattern of crystalline Form N1 of Sitagliptin (S)-mandelate.

Hereinafter, is described a crystalline Sitagliptin (S)-mandelate, designated Form N1, characterized by data selected from: a powder XRD pattern with peaks at 12.1°, 17.5°, 20.2°, 21.0° and 26.0°±0.2° 2θ; a powder XRD pattern as shown in FIG. 11a; and combinations thereof.

Sitagliptin (S)-mandelate Form N1 can be also characterized by a powder XRD pattern with peaks at 3.3°, 5.8°, 6.9°, 12.1°, 14.6°, 17.5°, 19.6°, 20.2°, 21.0° and 26.0°±0.2° 2θ.

Figure 11B:
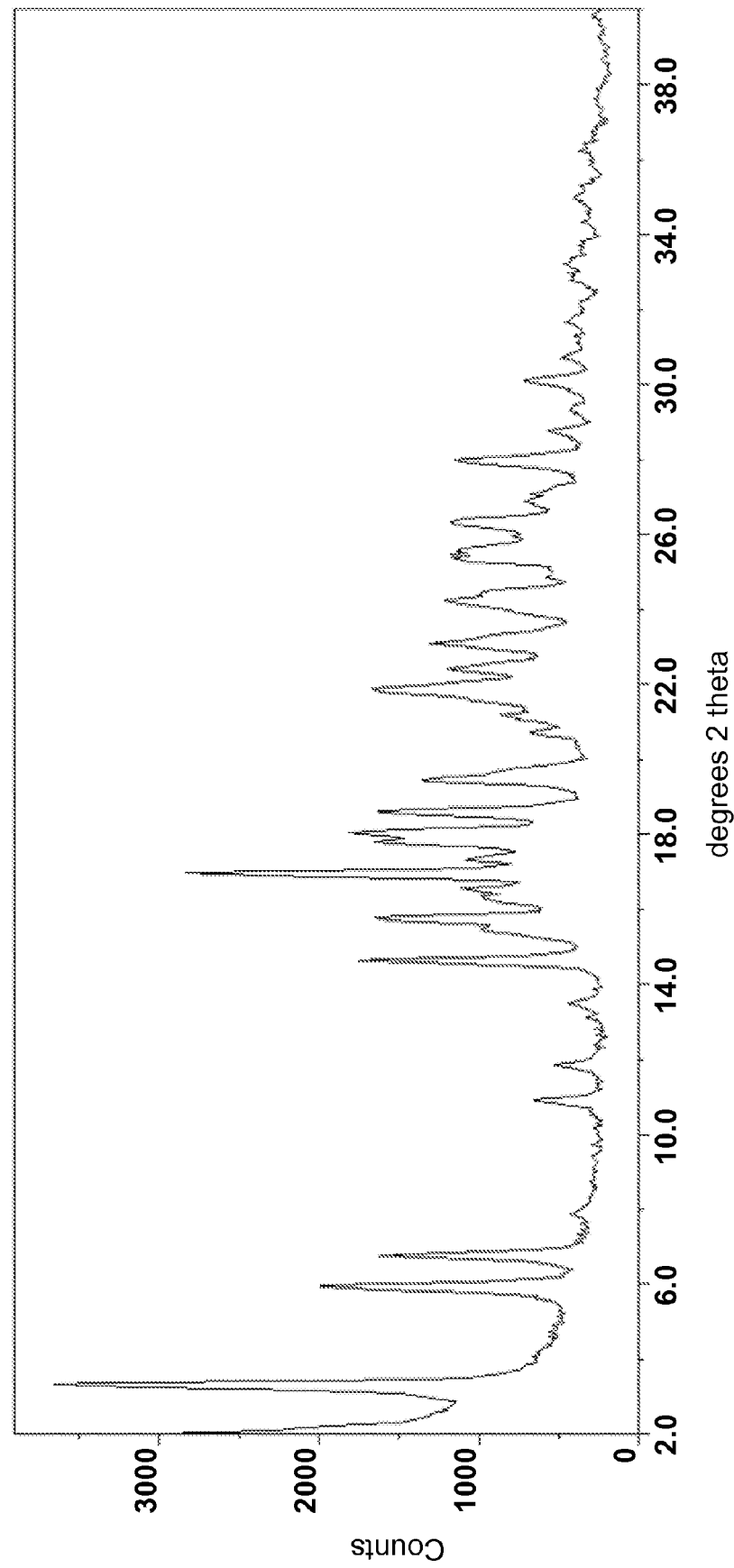
FIG. 11b shows a powder XRD pattern of crystalline Form N2 of Sitagliptin (S)-mandelate.
Figure 11C:
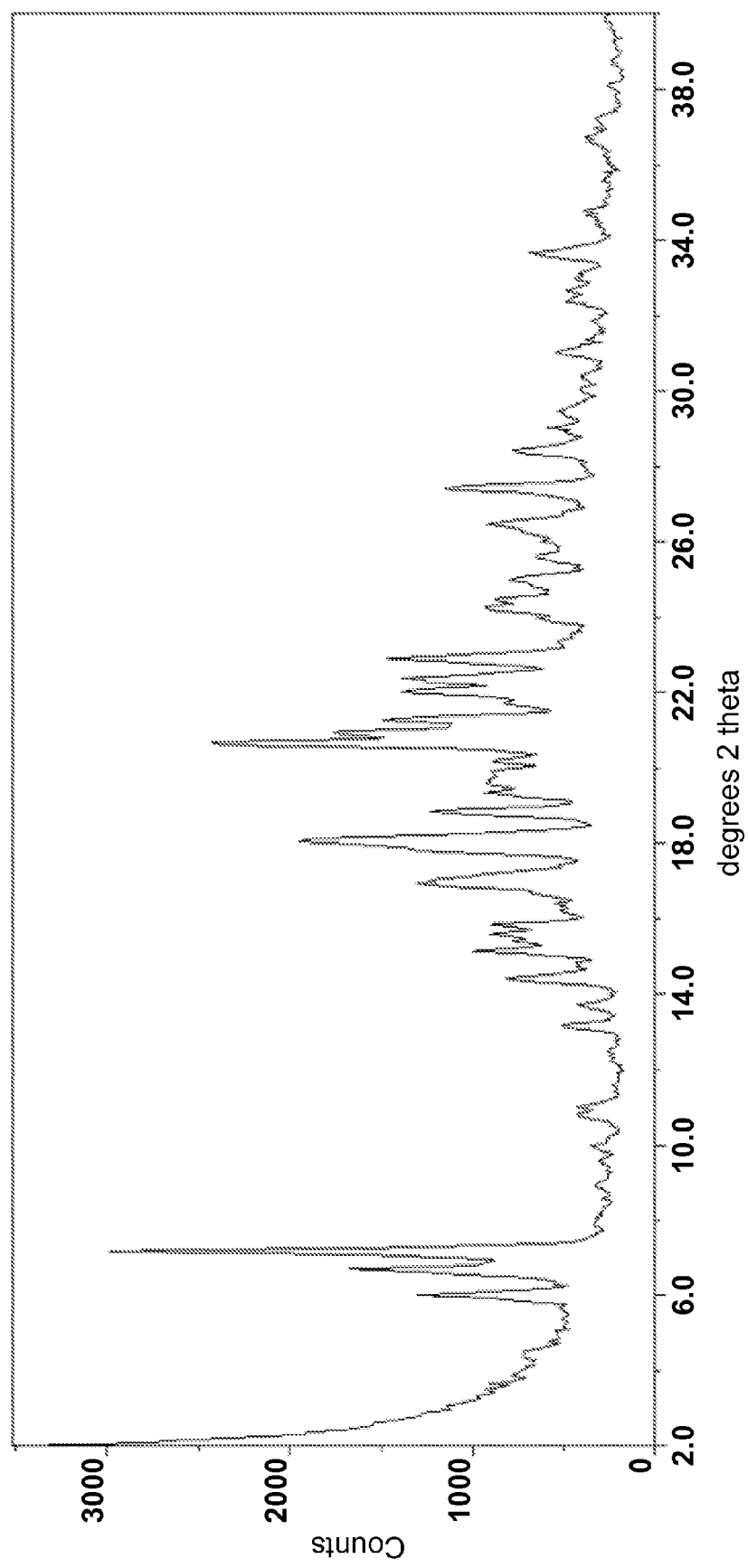
FIG. 11c shows a powder XRD pattern of crystalline Form N3 of Sitagliptin (S)-mandelate.
Figure 11D:
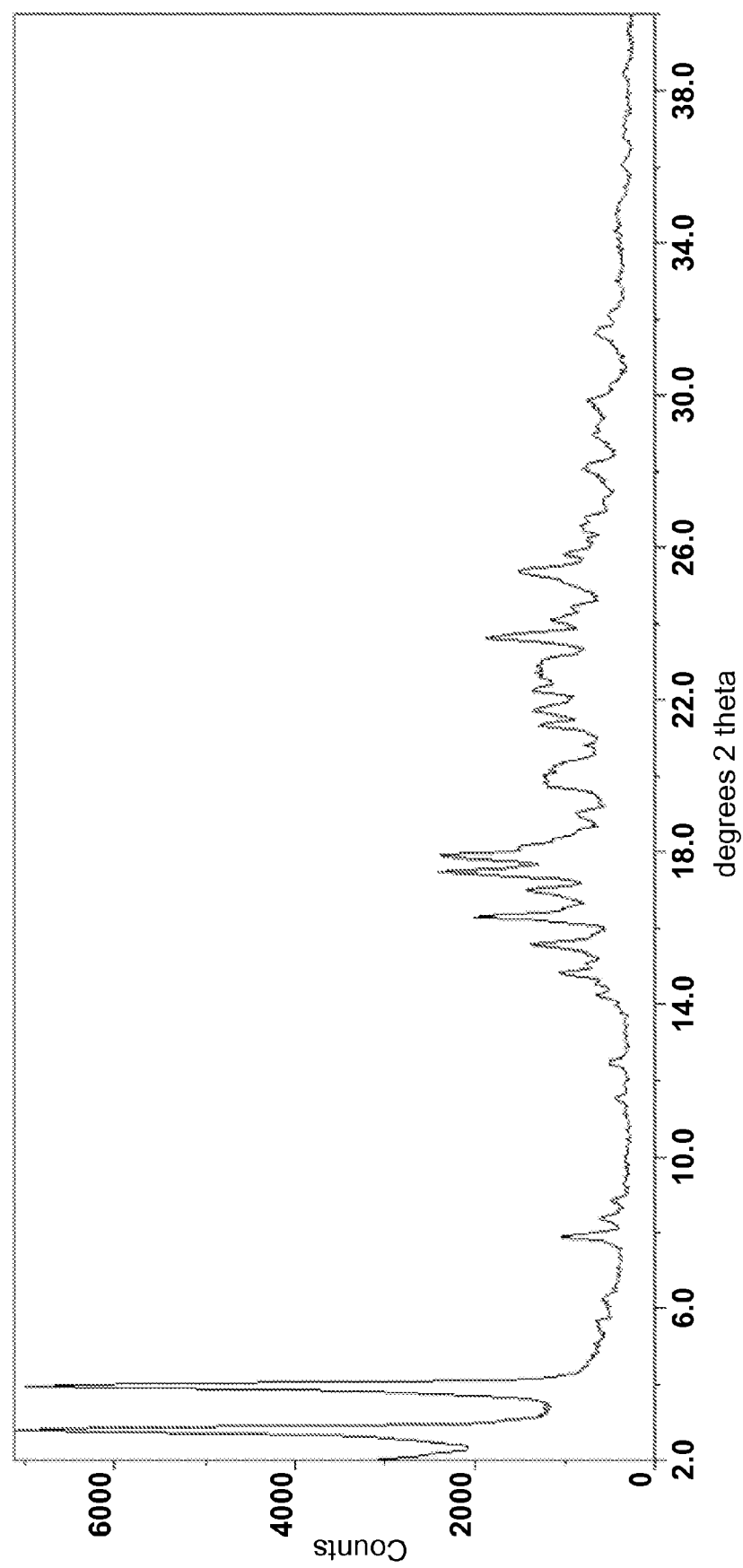
FIG. 11d shows a powder XRD pattern of crystalline Form N4 of Sitagliptin (S)-mandelate.
Figure 11E:
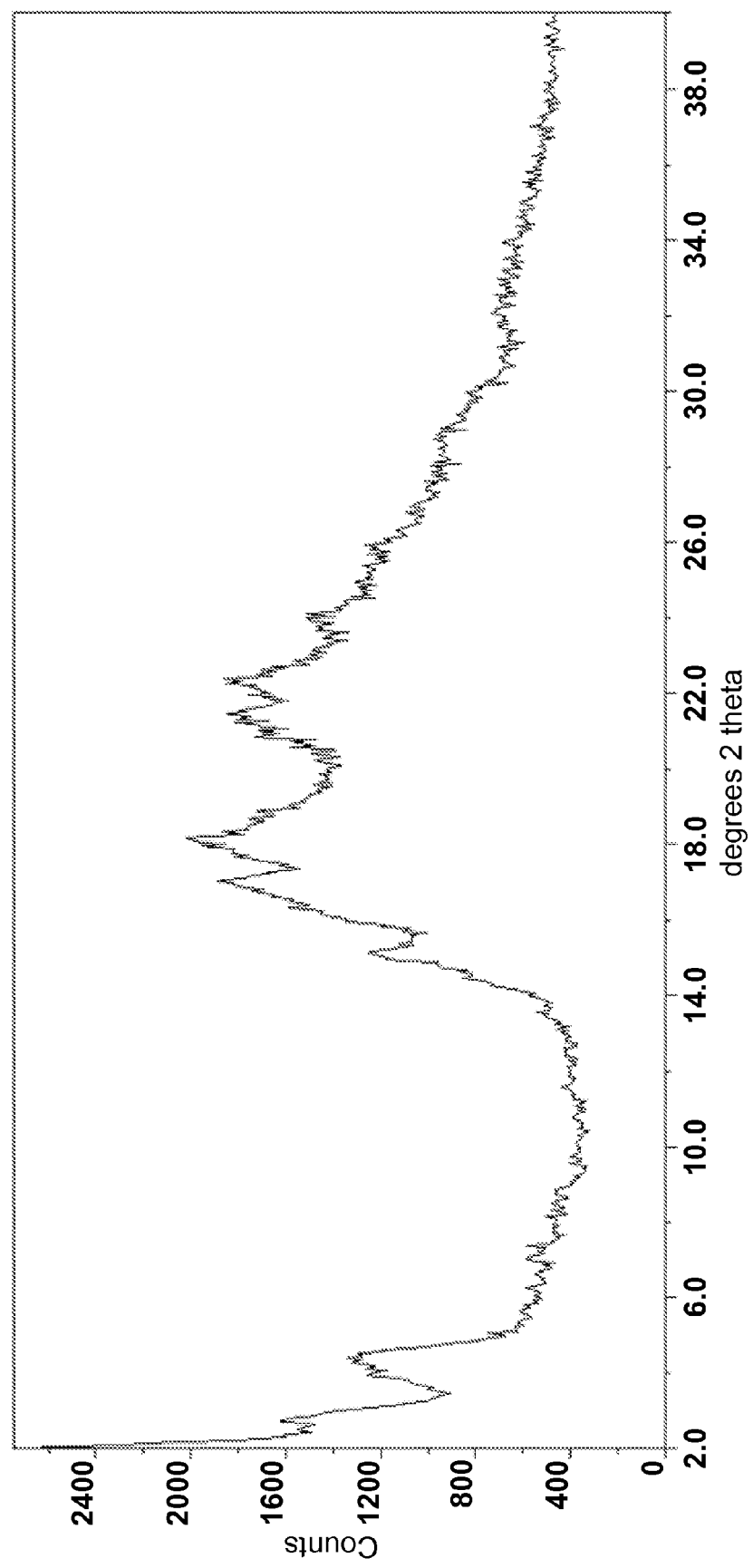
FIG. 11e shows a powder XRD pattern of amorphous Sitagliptin mandelate.
Figure 11F:
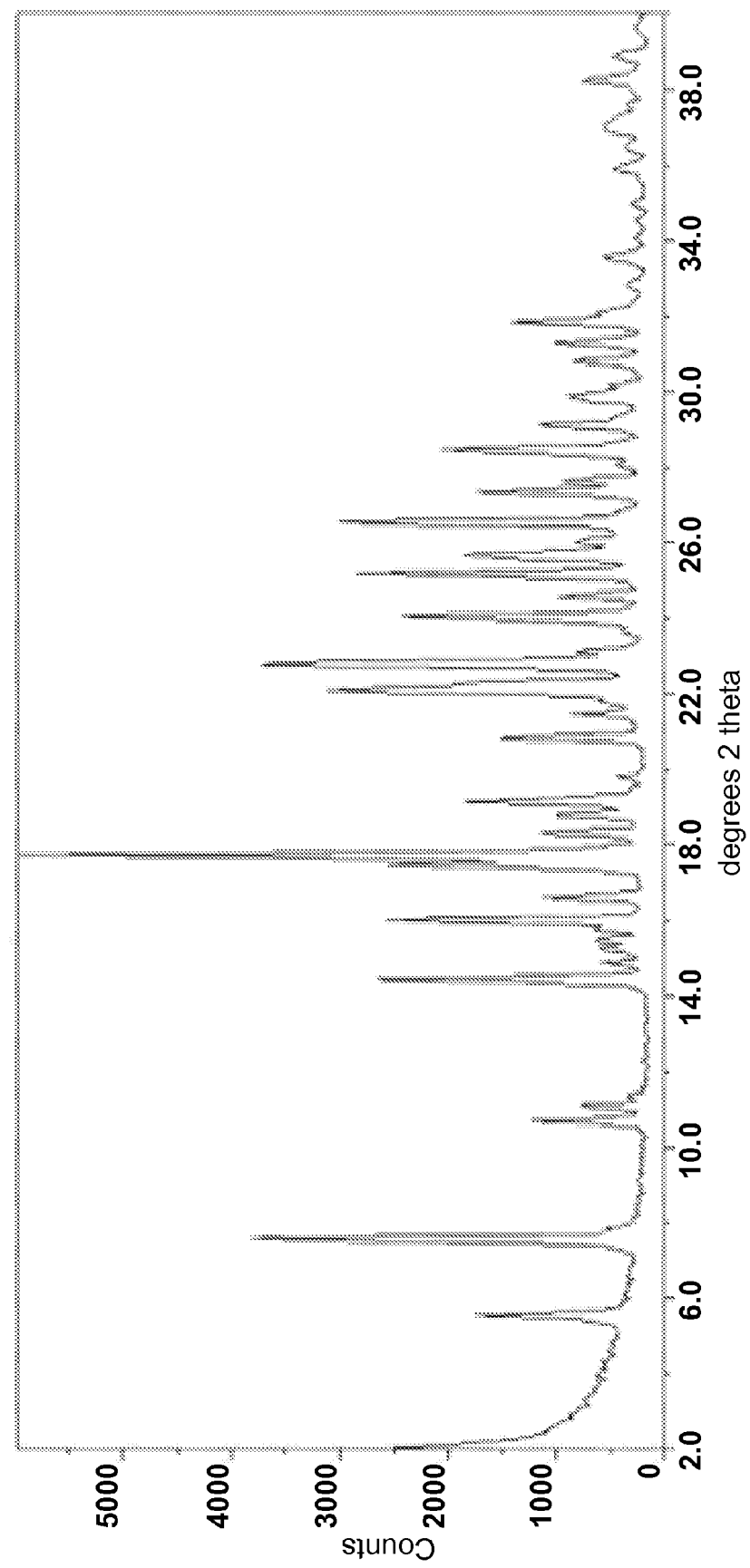
FIG. 11f shows a powder XRD pattern of crystalline Form N5 of Sitagliptin (R)-mandelate.
Figure 11G:
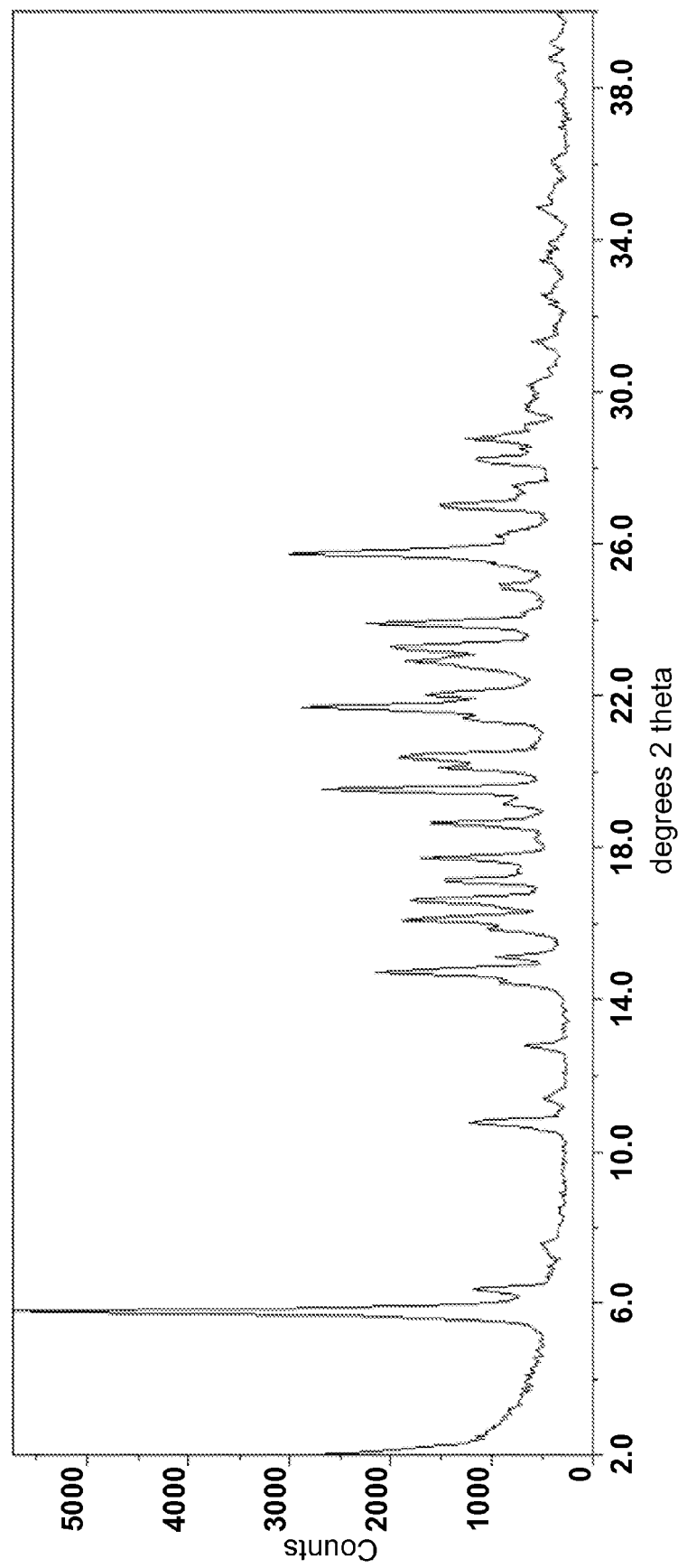
FIG. 11g shows a powder XRD pattern of crystalline Form N6 of Sitagliptin (R)-mandelate.
Figure 11H:
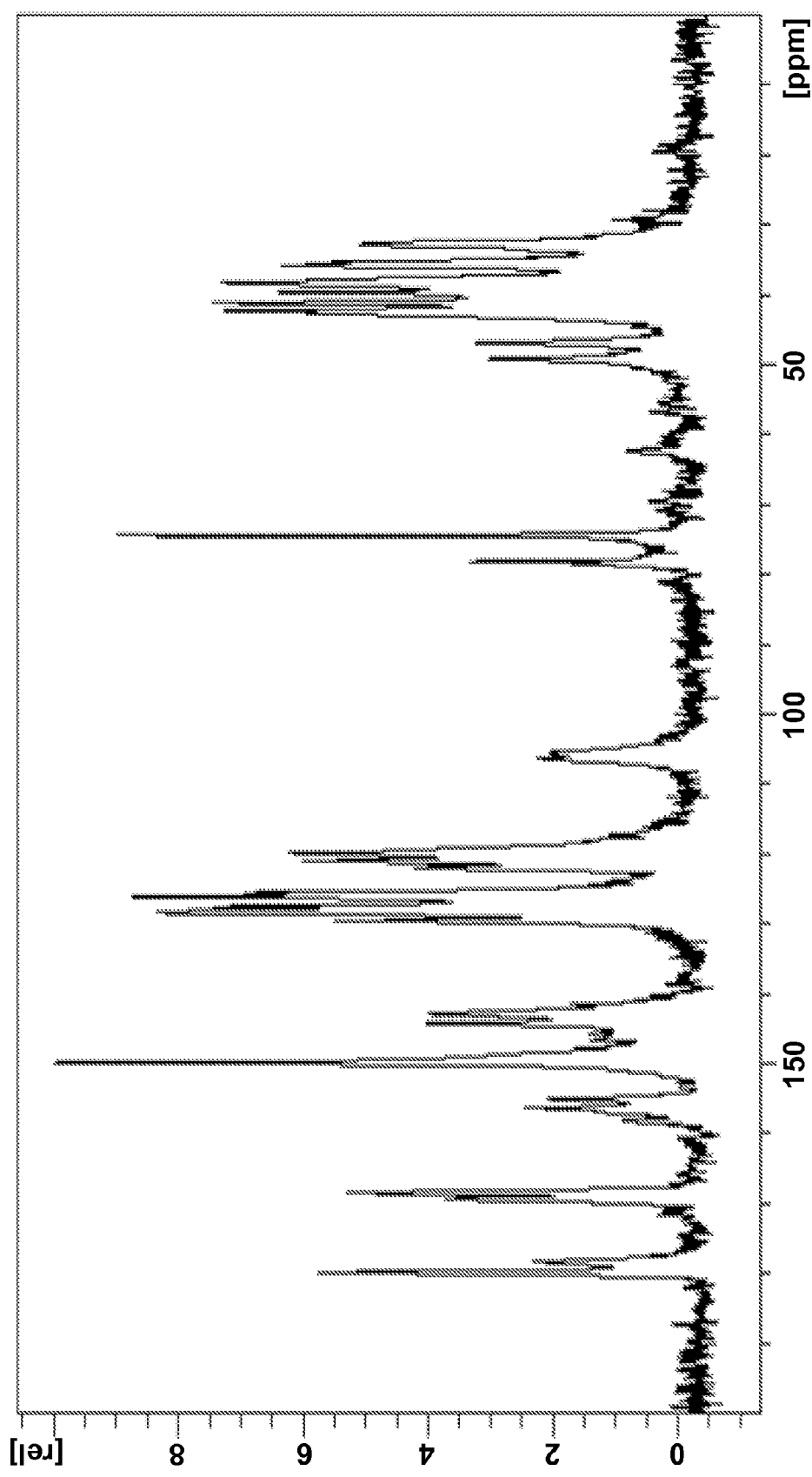
FIG. 11h shows a solid state $^{13}$C NMR spectrum of Sitagliptin (S)-(+)-mandelate Form N4 in the 0-200 ppm range.
Figure 11I:
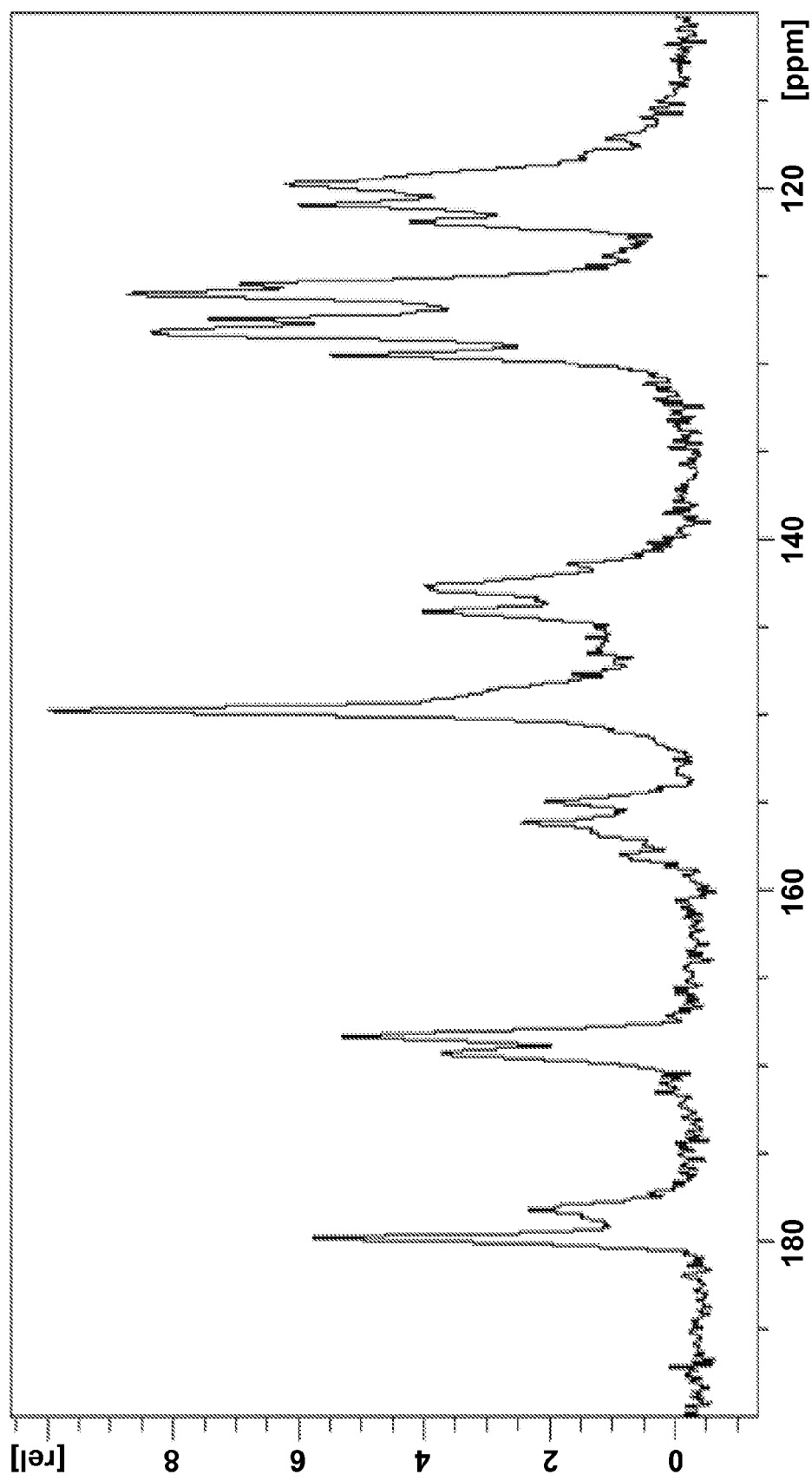
FIG. 11i shows a solid state $^{13}$C NMR spectrum of Sitagliptin (S)-(+)-mandelate Form N4 in the 110-190 ppm range.
Figure 11J:
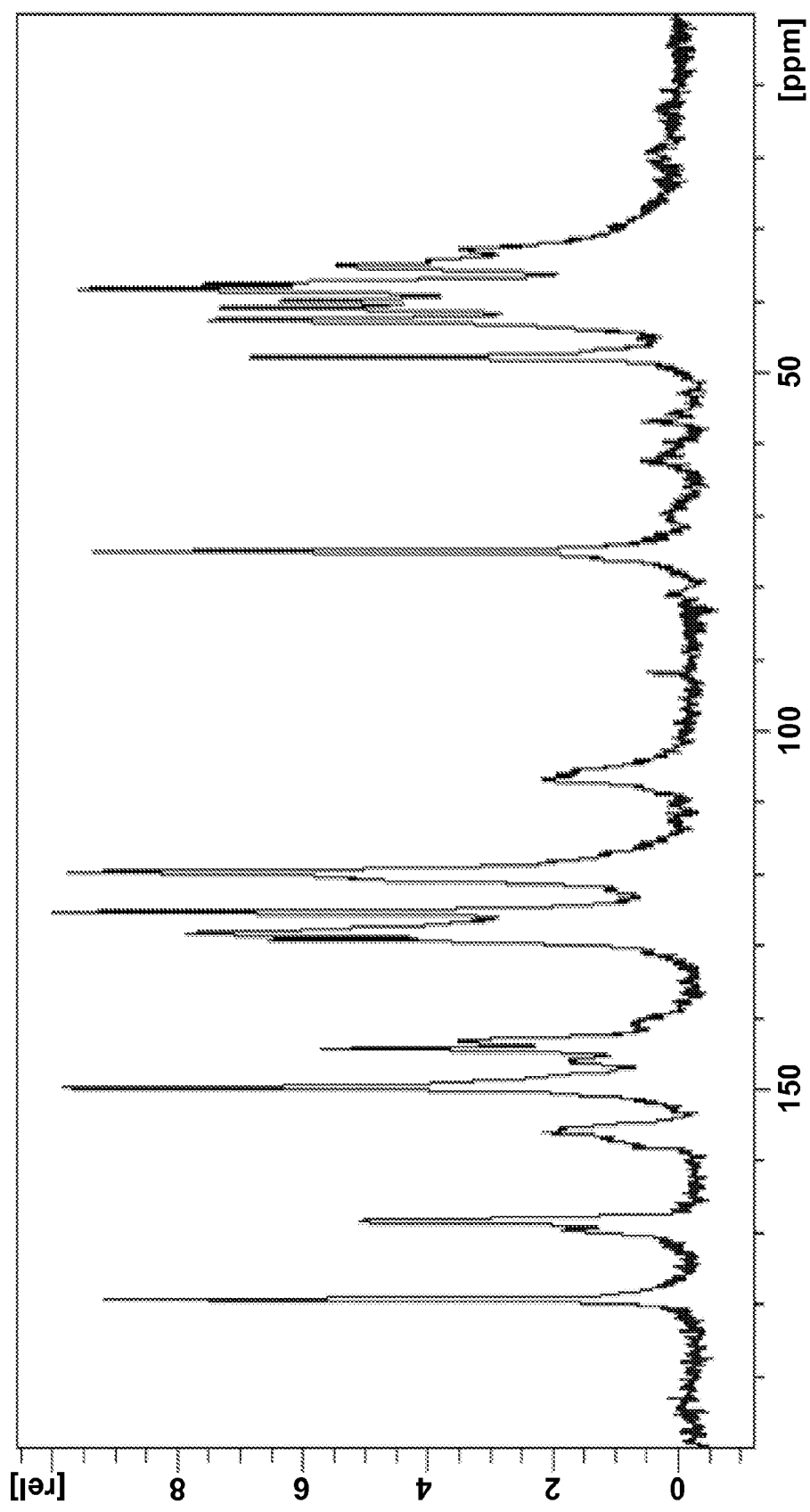
FIG. 11j shows a solid state $^{13}$C NMR spectrum of Sitagliptin (S)-(+)-mandelate Form N1 in the 0-200 ppm range.
Figure 11K:
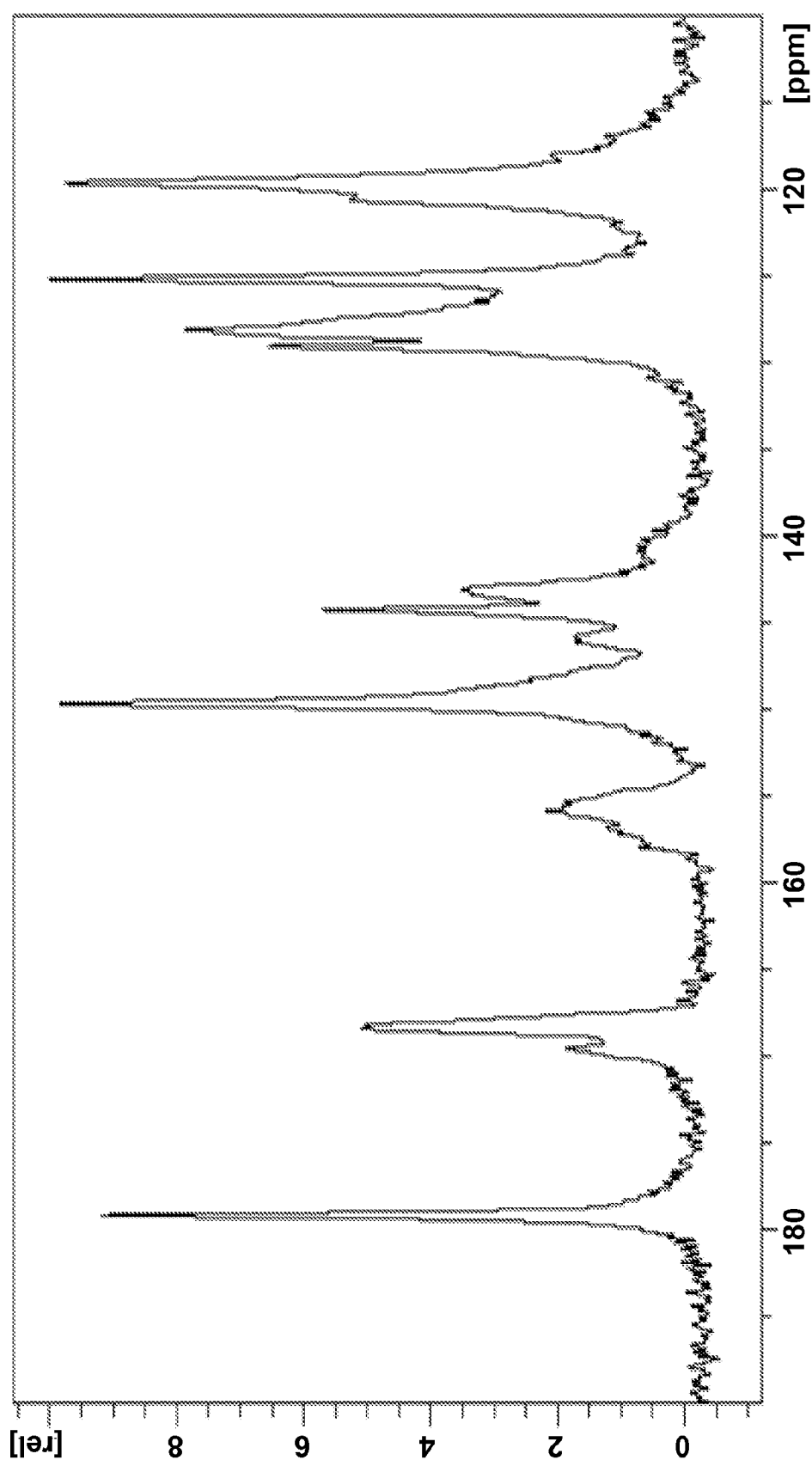
FIG. 11k shows a solid state $^{13}$C NMR spectrum of Sitagliptin (S)-(+)-mandelate Form N1 in the 110-190 ppm range.
Figure 11I:
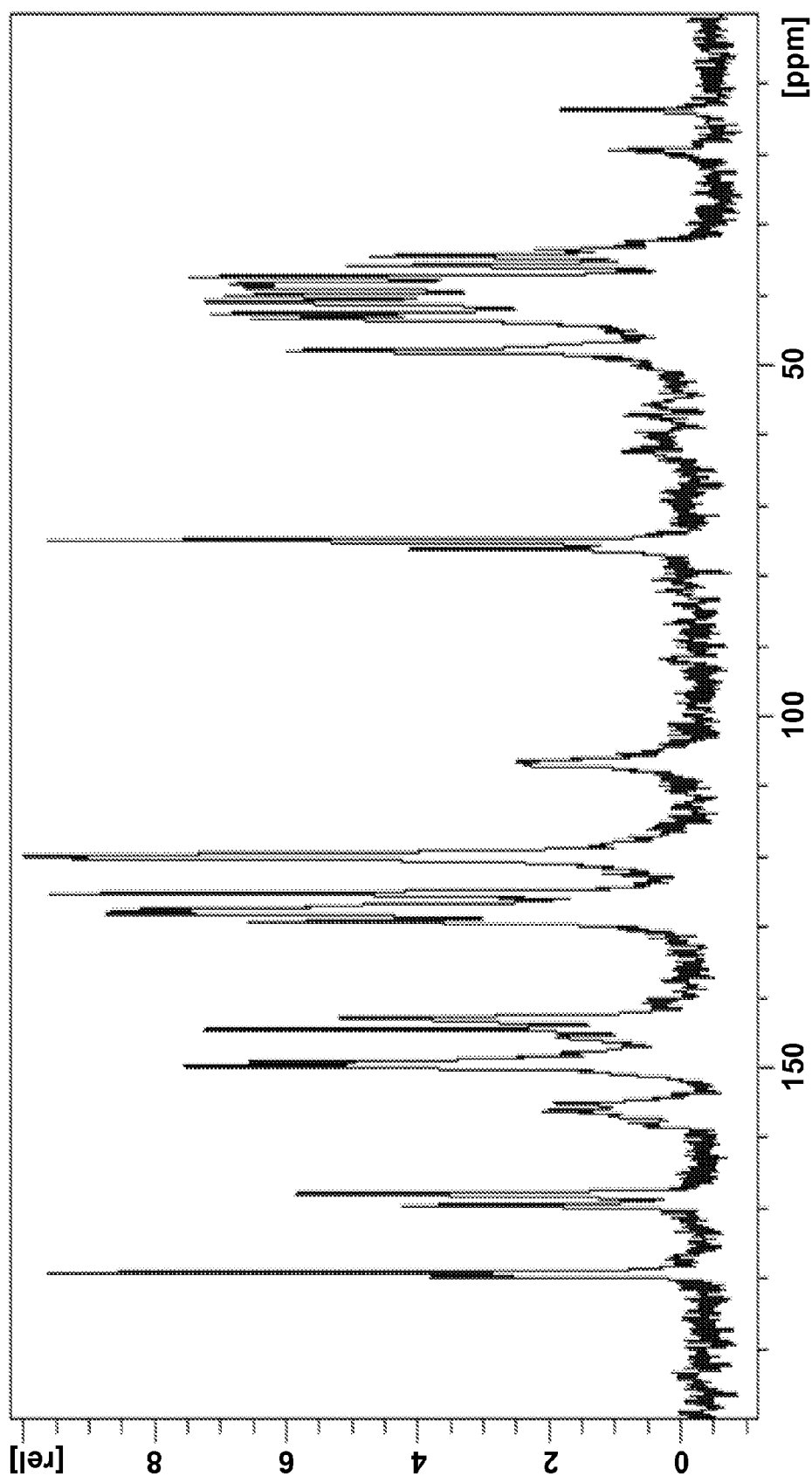

Sitagliptin (S)-mandelate From N1 can be also characterized by data selected from: a solid-state $^{13}$C NMR spectrum with signals at 144.2, 168.3 and 179.1±0.2 ppm; a solid-state $^{13}$C NMR spectrum having chemical shifts differences between the signal exhibiting the lowest chemical shift and another in the chemical shift range of 110 to 190 ppm of 24.6, 48.7 and 59.5±0.1 ppm; and a $^{13}$C NMR spectrum is depicted in FIGS. 11j and 11k. The signal exhibiting the lowest chemical shift in the chemical shift area of 110 to 190 ppm is typically at 119.6±1 ppm Sitagliptin (S)-mandelate crystalline Form N1 can be prepared by a process comprising forming a solution of Sitagliptin base in acetonitrile; combining the solution with mandelic acid to form a precipitate; and isolating the obtained precipitate. Preferably, the mandelic acid is used at a mol ratio of about 1:1 of Sitagliptin base to mandelic acid. Preferably, the acid is (S)-(+)-mandelic acid.

After the addition of the acid, in any of the processes herein for preparing any of the crystalline Sitagliptin mandelate forms, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours to about 3 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Hereinafter, is described a crystalline Sitagliptin (S)-mandelate, designated Form N2, characterized by data selected from: a powder XRD pattern with peaks at 11.8°, 17.0°, 18.1°, 22.4° and 24.2°±0.2° 2θ; a powder XRD pattern as shown in FIG. 11b; and combinations thereof.

Sitagliptin (S)-Form N2 can be also characterized by a powder XRD pattern with peaks at 3.3°, 5.9°, 6.8°, 11.8°, 14.6°, 17.0°, 18.1°, 18.6°, 22.4° and 24.2°±0.2° 2θ.

Figure 11M:
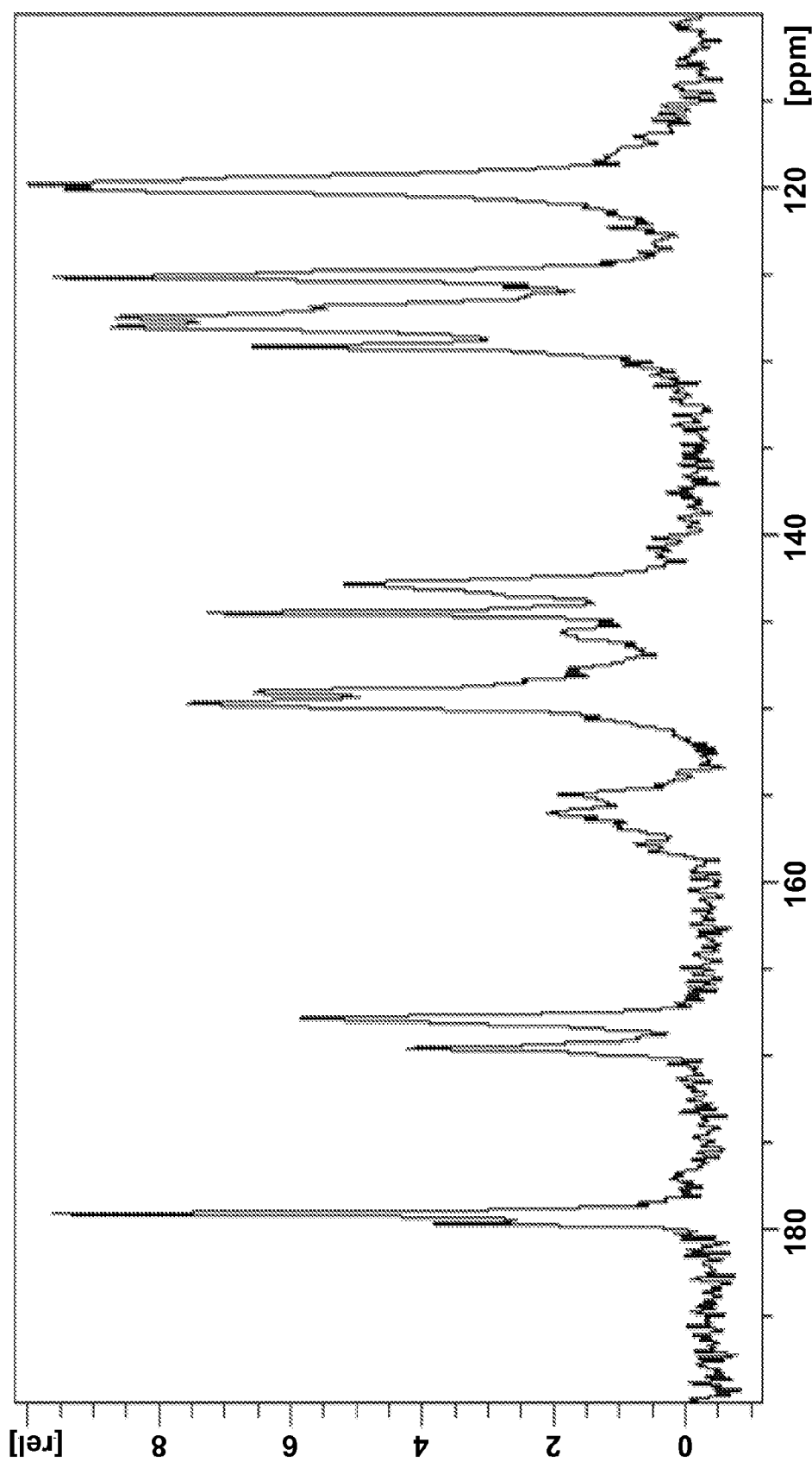
FIG. 11m shows a solid state $^{13}$C NMR spectrum of Sitagliptin (S)-(+)-mandelate Form N2 in the 110-190 ppm range.

Sitagliptin (S)-mandelate Form N2 can be also characterized by data selected from: a solid-state $^{13}$C NMR spectrum with signals at 144.4, 167.8 and 179.0±0.2 ppm; a solid-state $^{13}$C NMR spectrum having chemical shifts differences between the signal exhibiting the lowest chemical shift and another in the chemical shift range of 110 to 190 ppm of 24.7, 48.1 and 59.3±0.1 ppm; and a $^{13}$C NMR spectrum is depicted in FIGS. 11l and 11m. The signal exhibiting the lowest chemical shift in the chemical shift area of 110 to 190 ppm is typically at 119.7±1 ppm.

Sitagliptin (S)-mandelate crystalline Form N2 can be prepared by a process comprising forming a solution of Sitagliptin base in ethyl acetate; combining the solution with mandelic acid to form a precipitate; and isolating the obtained precipitate. Preferably, the mandelic acid is used at a mol ratio of about 1:1 of Sitagliptin base to mandelic acid. Preferably, the acid is (S)-(+)-mandelic acid.

Hereinafter, is described a crystalline Sitagliptin (S)-mandelate, designated Form N3, characterized by data selected from: a powder XRD pattern with peaks at 6.0°, 6.7°, 7.2°, 14.4° and 18.1°±0.2° 2θ; a powder XRD pattern as shown in FIG. 11c; and combinations thereof.

Sitagliptin (S)-mandelate Form N3 can be also characterized by a powder XRD pattern with peaks at 6.0°, 6.7°, 7.2°, 13.2°, 14.4°, 16.9°, 18.1°, 18.8°, 20.7° and 22.9°±0.2° 2θ.

Sitagliptin (S)-mandelate crystalline Form N3 can be prepared by a process comprising forming a solution of Sitagliptin base in ethanol; combining the solution with mandelic acid to form a precipitate; and isolating the obtained precipitate. Preferably, the mandelic acid is used at a mol ratio of about 1:1 of Sitagliptin base to mandelic acid. Preferably, the acid is (S)-(+)-mandelic acid.

Hereinafter, is described a crystalline Sitagliptin (S)-mandelate, designated Form N4, characterized by data selected from: a powder XRD pattern with peaks at 2.8°, 4.0°, 7.9°, 16.3° and 17.5°±0.2° 2θ; a powder XRD pattern as shown in FIG. 11d; and combinations thereof.

Sitagliptin (S)-mandelate Form N4 can be also characterized by a powder XRD pattern with peaks at 2.8°, 4.0°, 7.9°, 14.8°, 15.5°, 16.3°, 17.0°, 17.5°, 17.9° and 23.6°±0.2° 2θ.

Sitagliptin (S)-mandelate Form N4 can be also characterized by data selected from: a solid-state $^{13}$C NMR spectrum with signals at 126.0, 149.7 and 179.7±0.2 ppm; a solid-state $^{13}$C NMR spectrum having chemical shifts differences between the signal exhibiting the lowest chemical shift and another in the chemical shift range of 110 to 190 ppm of 6.3, 30.0 and 60.0±0.1 ppm; and a $^{13}$C NMR spectrum is depicted in FIGS. 11h and 11i. The signal exhibiting the lowest chemical shift in the chemical shift area of 110 to 190 ppm is typically at 119.7±1 ppm.

Sitagliptin (S)-mandelate crystalline Form N4 can be prepared by a process comprising forming a solution of Sitagliptin base in acetone; combining the solution with mandelic acid to form a precipitate; and isolating the obtained precipitate. Preferably, the mandelic acid is used at a mol ratio of about 1:1 of Sitagliptin base to mandelic acid. Preferably, the acid is (S)-(+)-mandelic acid.

Hereinafter, is described a crystalline Sitagliptin (R)-(−)-mandelate, designated Form N5, characterized by data selected from: a powder XRD pattern with peaks at 5.5°, 7.6°, 14.4°, 16.0° and 17.7°±0.2° 2θ; a powder XRD pattern as shown in FIG. 11f; and combinations thereof.

Preferably, Form N5 is substantially free of a peak at 6.0°±0.2° 2θ.

Sitagliptin (R)-(−)-mandelate Form N5 can be also characterized by a powder XRD pattern with peaks at 5.5°, 7.6°, 14.4°, 16.0°, 17.7°, 22.1°, 22.8°, 24.0°, 25.1° and 26.5°±0.2° 2θ.

Hereinafter, is described a crystalline Sitagliptin (R)-(−)-mandelate, designated Form N6, characterized by data selected from: a powder XRD pattern with peaks at 5.8°, 14.7°, 16.1°, 16.6° and 17.1°±0.2° 2θ; a powder XRD pattern as shown in FIG. 11g; and combinations thereof.

Sitagliptin (R)-(−)-mandelate Form N6 can be also characterized by a powder XRD pattern with peaks at 5.8°, 14.7°, 16.1°, 16.6°, 17.1°, 18.6°, 19.5°, 21.7°, 23.9° and 25.7°±0.2° 2θ.

Hereinafter, is described amorphous Sitagliptin mandelate. The amorphous Sitagliptin mandelate is characterized by the XRD diffractogram shown in FIG. 11e.

The amorphous Sitagliptin mandelate can be prepared by a process comprising forming a slurry of Sitagliptin base in methyl tert-butyl ether; combining the slurry with mandelic acid; and isolating the obtained precipitate. Preferably, the mandelic acid is used at a mol ratio of about 1:1 of Sitagliptin base to mandelic acid. Preferably, the acid is (S)-(+)-mandelic acid.

After the addition of the acid, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can be further dried.

Figure 12A:
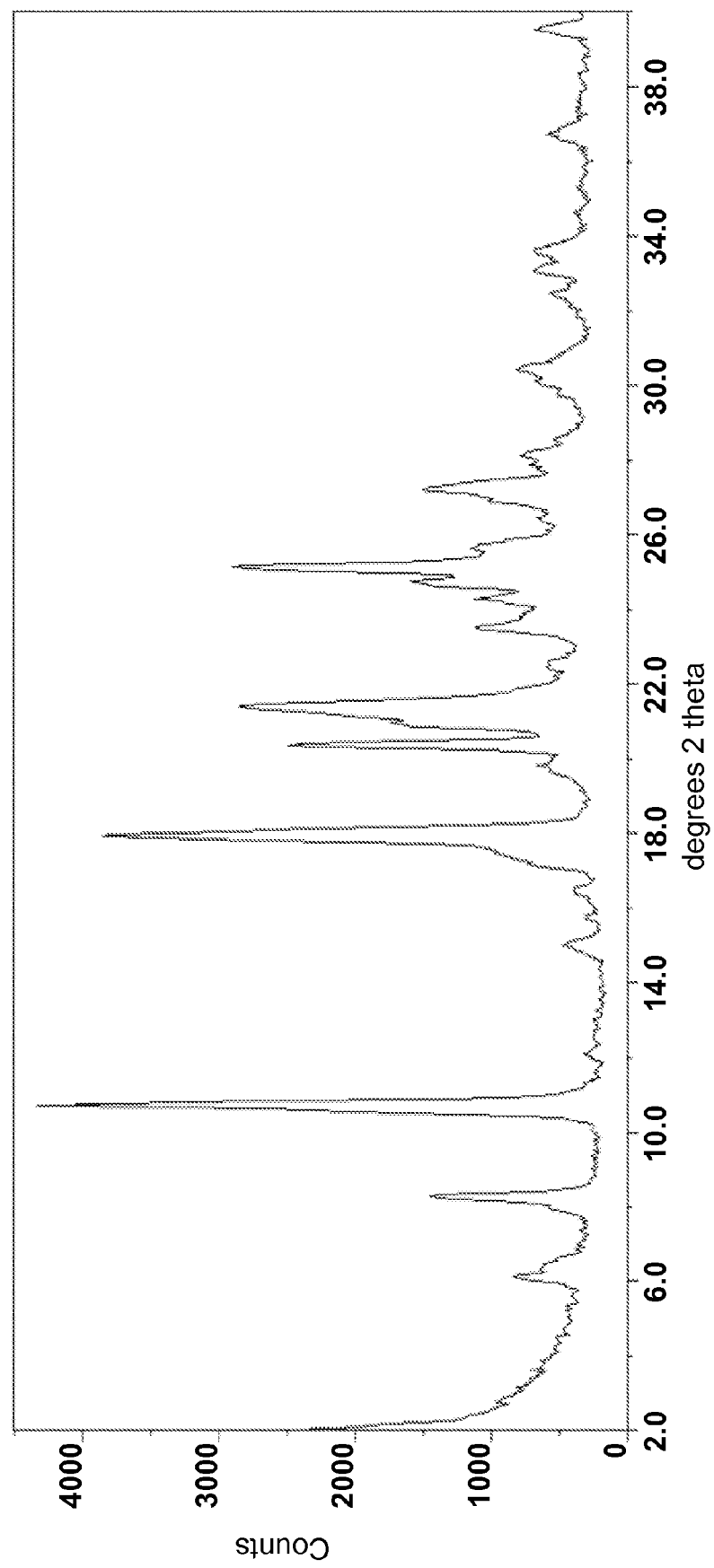
FIG. 12a shows a powder XRD pattern of crystalline Form L1 of Sitagliptin lactate.

Hereinafter, is described a crystalline Sitagliptin lactate, designated Form L1, characterized by data selected from: a powder XRD pattern with peaks at 10.7°, 17.9°, 20.3° and 21.4°±0.2° 2θ; a powder XRD pattern as shown in FIG. 12a; and combinations thereof.

Sitagliptin lactate Form L1 can be also characterized by a powder XRD pattern with peaks at 6.1°, 8.3°, 10.7°, 17.9°, 20.3°, 21.4°, 23.5°, 25.1° and 27.2°±0.2° 2θ.

Sitagliptin lactate crystalline Form L1 can be prepared by a process comprising forming a solution of Sitagliptin base in acetonitrile; combining the solution with lactic acid to form a precipitate; and isolating the obtained precipitate. Preferably, the lactic acid is used at a mol ratio of about 1:1 of Sitagliptin base to lactic acid.

After the addition of the acid, in any of the processes for preparing any of the crystalline Sitagliptin lactate forms, the obtained mixture can be heated to a temperature from about 40° C. to about 60° C., or from about 45° C. to about 55° C., for example about 50° C. Heating is applied for example, for about 1 to about 10 hours, or from about 1 to about 4 hours, for example, for about 2 hours. The mixture can be cooled to a temperature from about 0° C. to about room temperature, or from about 10° C. to about room temperature, for example about room temperature, preferably overnight, before collecting the obtained precipitate. The obtained precipitate can further be dried.

Figure 12B:
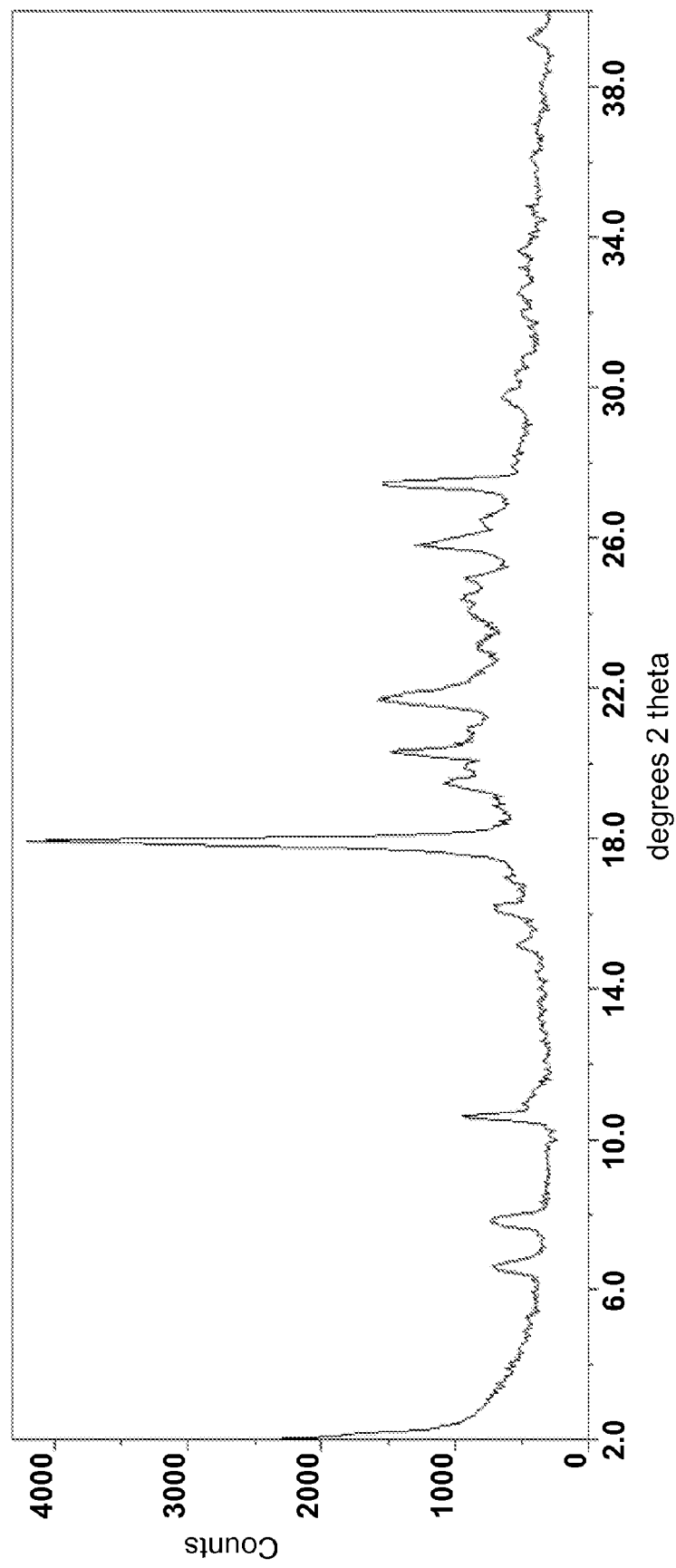
FIG. 12b shows a powder XRD pattern of crystalline Form L2 of Sitagliptin lactate.
Figure 12C:
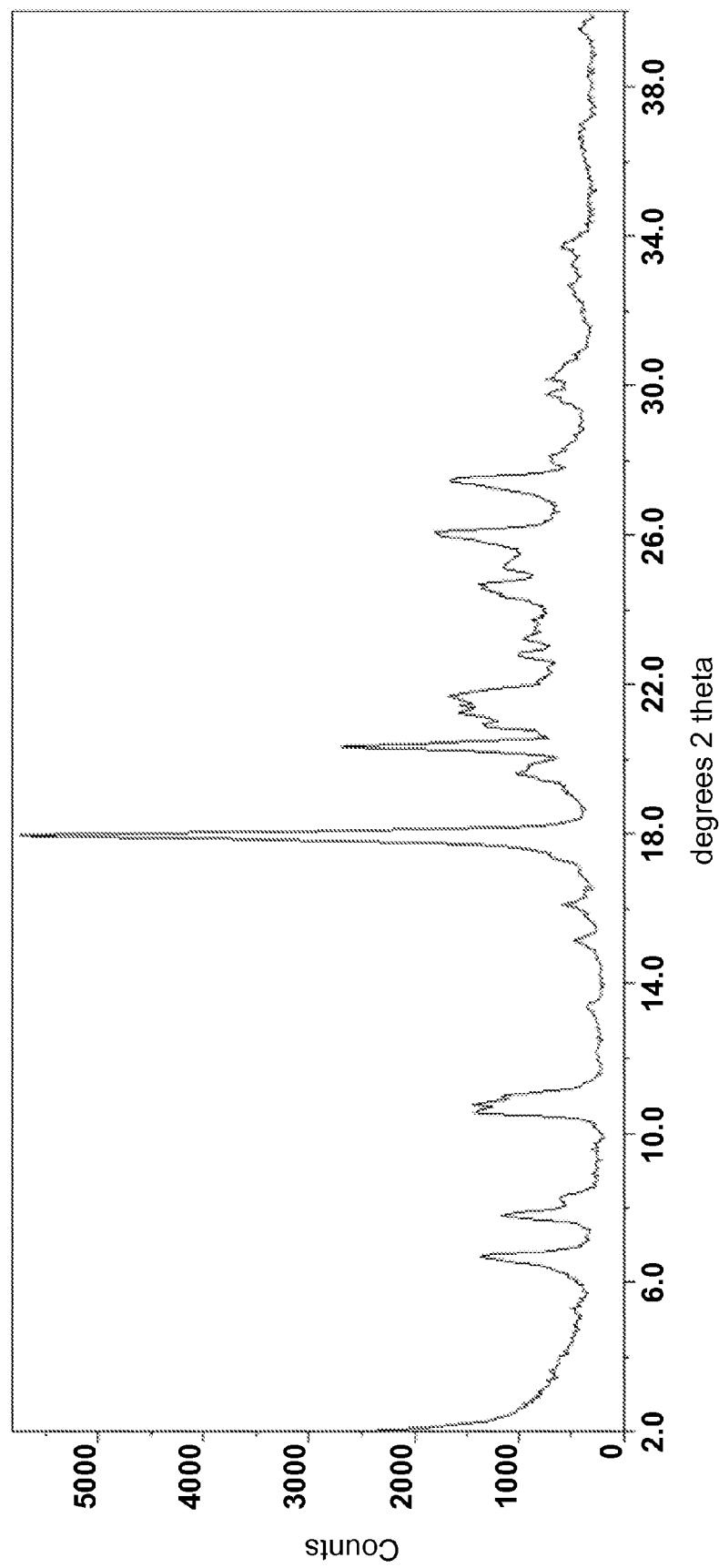
FIG. 12c shows a powder XRD pattern of crystalline Form L2 of Sitagliptin lactate.

Hereinafter, is described a crystalline Sitagliptin lactate, designated Form L2, characterized by data selected from: a powder XRD pattern with peaks at 6.6°, 7.8°, 10.6°, 17.9° and 20.3°±0.2° 2θ; a powder XRD pattern as shown in FIG. 12c; and combinations thereof.

Sitagliptin lactate Form L2 can be also characterized by a powder XRD pattern with peaks at 3.3°, 5.9°, 6.6°, 7.8°, 10.6°, 16.1°, 17.9°, 19.5°, 20.3°, 21.7°, 25.8° and 27.4°±0.2° 2θ.

Sitagliptin lactate crystalline Form L2 can be prepared by a process comprising forming a solution of Sitagliptin base in an organic solvent selected from acetone, and ethyl acetate; combining the solution with lactic acid to form a precipitate; and isolating the obtained precipitate. Preferably, the lactic acid is used at a mol ratio of about 1:1 of Sitagliptin base to lactic acid.

Figure 12D:
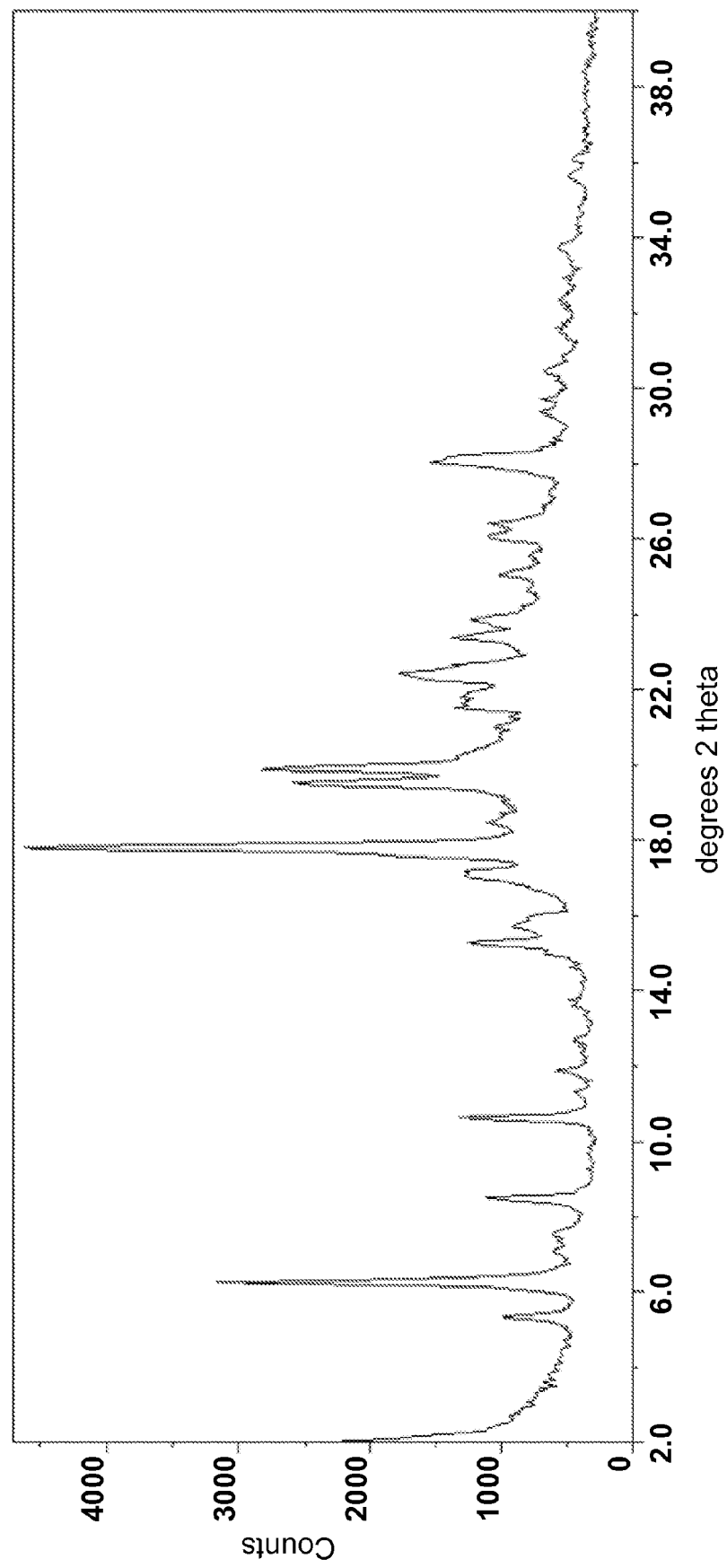
FIG. 12d shows a powder XRD pattern of crystalline Form L3 of Sitagliptin lactate.

Hereinafter, is described a crystalline Sitagliptin lactate, designated Form L3, characterized by data selected from: a powder XRD pattern with peaks at 5.3°, 6.2°, 8.5°, 10.6° and 17.8°±0.2° 2θ; a powder XRD pattern as shown in FIG. 12d; and combinations thereof.

Sitagliptin lactate Form L3 can also be characterized by a powder XRD pattern with peaks at 5.3°, 6.2°, 8.5°, 10.6°, 15.3°, 17.8°, 19.5°, 19.9°, 22.4° and 28.0°±0.2° 2θ.

Sitagliptin lactate crystalline Form L3 can be prepared by a process comprising forming a slurry of Sitagliptin base in methyl tert-butyl ether; combining the slurry with lactic acid to form a precipitate; and isolating the obtained precipitate. Preferably, the lactic acid is used at a mol ratio of about 1:1 of Sitagliptin base to lactic acid.

Figure 12E:
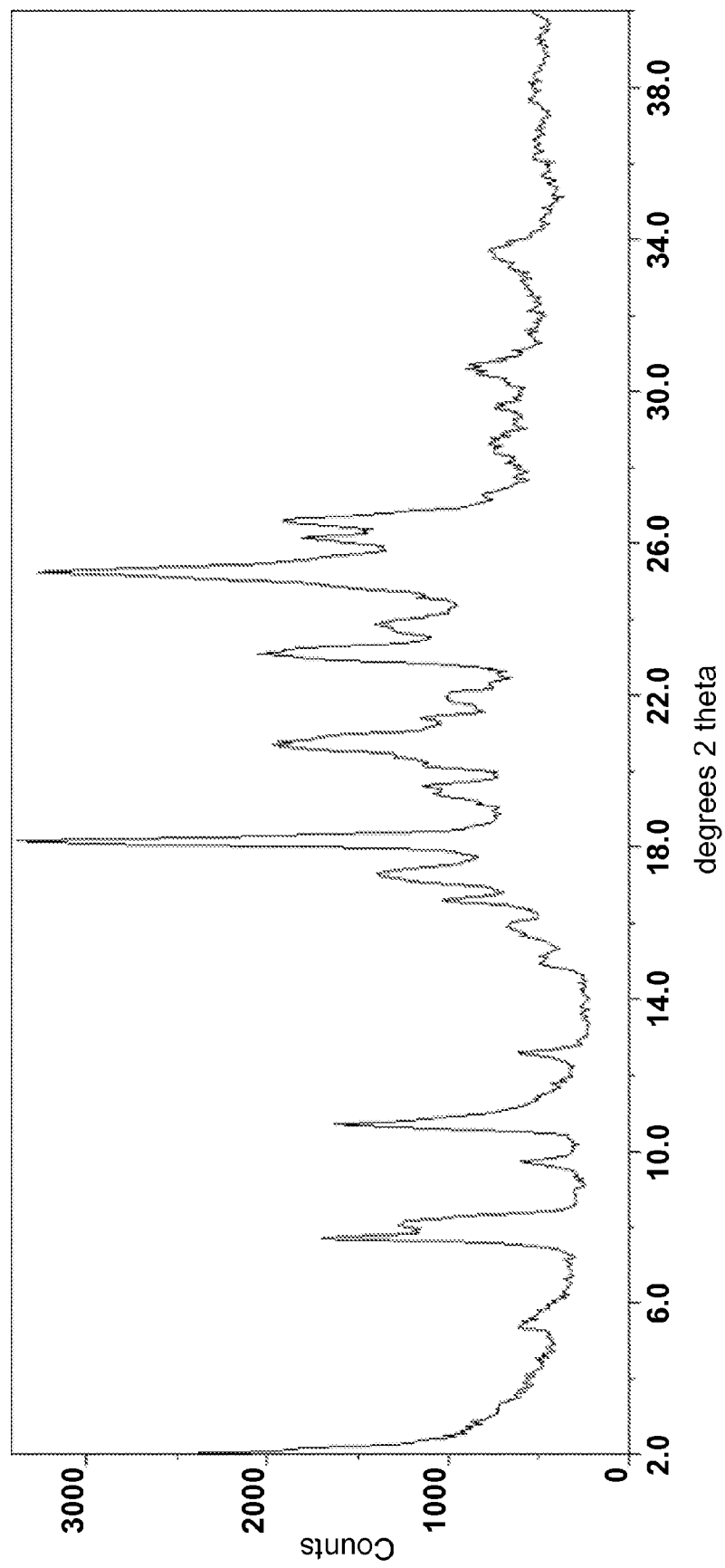
FIG. 12e shows a powder XRD pattern of crystalline Form L4 of Sitagliptin lactate.

Hereinafter, is described a crystalline Sitagliptin lactate, designated Form L4, characterized by data selected from: a powder XRD pattern with peaks at 7.7°, 10.7°, 17.3°, 18.1° and 25.2°±0.2° 2θ; a powder XRD pattern as shown in FIG. 12e; and combinations thereof.

Sitagliptin lactate Form L4 can be also characterized by a powder XRD pattern with peaks at 7.7°, 9.7°, 10.7°, 12.6°, 16.6°, 17.3°, 18.1°, 20.7°, 23.1° and 25.2°±0.2° 2θ.

Sitagliptin lactate crystalline Form L4 can be prepared by a process comprising forming a solution of Sitagliptin base in ethanol; combining the solution with lactic acid to form a precipitate; and isolating the obtained precipitate. Preferably, the lactic acid is used at a mol ratio of about 1:1 of Sitagliptin base to lactic acid.

Hereinafter, is described amorphous Sitagliptin orotate. The amorphous Sitagliptin orotate is characterized by the XRD diffractogram shown in FIGS. 13a-d.

The present invention further encompasses 1) a pharmaceutical composition comprising any one, or combination, of solid state Forms, as described above and at least one pharmaceutically acceptable excipient and 2) the use of any one, or combination, of the above-described solid state Forms, in the manufacture of a pharmaceutical composition. The pharmaceutical composition can be useful for the treatment of type 2 diabetes mellitus. The present invention also provides crystalline forms as described above for use as a medicament, preferably for the treatment of type 2 diabetes mellitus.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

X-Ray Power Powder Diffraction

Unless recited otherwise, X-Ray powder diffraction data was obtained by using methods known in the art using a SCINTAG powder X-Ray diffractometer model X'TRA equipped with a solid-state detector. Copper radiation of 1.5418 Å was used. A round aluminum sample holder with zero background was used. The scanning parameters included: range: 2-40 degrees two-theta; scan mode: continuous scan; step size: 0.05 deg.; and a rate of 3 deg/min.

$^{13}$C NMR Spectra:

$^{13}$C NMR at 125 MHz using Bruker Avance II+500. SB probe using 4 mm rotors

Magic angle was set using KBr. Homogeneity of magnetic field checked using adamantane. Parameters for Cross polarization optimized using glycine.

Spectral reference set according to glycine as external standard (176.03 ppm for low field carboxyl signal).

Magic Angle Spinning Rate: 11 kHz
Pulse Program: cp with tppm15 during decoupling
Delay time: 5 s (except for Sitagliptin acetate, wherein the delay time was 10 s)
Contact time: 2 ms
Number of Scans: 1024
TGA Thermogram TGA thermogram was measured using METTLER TOLEDO TGA/DSC STAR$^e$.

Heating rate: 10°/minute. N$_2$ flow rate: 40 ml/minute

EXAMPLES

Example 1

Rhodium(I) chloride 1,5-cyclooctadiene complex (24.1 mg, 0.2%) and (R)-(−)-1-[(S)-2-diphenylphosphino)ferrocenyl]ethyl di-tert-butylphosphine (56.8 mg, 0.44%) were added to degassed methanol (20 mL). The resulting solution was stirred at 25° C., degassed again, and then stirred for one hour at 25° C. This catalyst solution was used in the hydrogenation described below.

(Z)-3-amino-1-(3-(trifluoromethyl)-5,6-dihydro-[1,2,4]triazolo[4,3-a]-pyrazyn-7(8H)-yl)-4-(2,4,5-trifluorophenyl)but-2-en-1-one (10 gr, 1 equivalent) and methanol (50 ml) were added to a 250 ml hydrogenation bottle at 25° C. and the bottle was subjected to vacuum and nitrogen backflush three times. The catalyst solution was added to the hydrogenation bottle and the bottle was again subjected to vacuum and nitrogen backflush three times and then to vacuum and backflush with hydrogen gas three times. The resulting reaction mixture was maintained under hydrogen at a pressure of 5 bar and heated to 55° C. The heated mixture was stirred at 5 bar pressure, at 55° C. for 3 days to obtain Sitagliptin base in methanol solution (optical purity by HPLC 97%, purity by HPLC 63.7%).

Example 2

Sitagliptin (STG) Sulfate Crystalline Form S1

An half amount of the solution obtained in Example 1, was evaporated and dissolved in isopropanol (25 ml). A solution of sulfuric acid (0.6 gr in 25 ml of isopropanol) was added over 40 minutes and the resulting mixture was stirred at 25° C. for 16 hours. The product was separated by vacuum filtration, and the filtered product was washed with isopropanol (10 ml) and dried in vacuum oven at 40° C. for 16 hours to obtain 2.9 gr of Sitagliptin sulfate crystalline form S1.

Example 3

STG Dibenzoyl-D-Tartarate Crystalline Form D1

STG (Sitagliptin) base (350 mg) was dissolved in acetonitrile (2 mL) at 25° C. (+)-Dibenzoyl-D-tartaric acid (98%, 323 mg, 1 eq) was then added and the resulting mixture was heated to 50° C. The mixture became a very thick slurry, therefore additional acetonitrile (1.5 mL) was added. The resulting mixture was stirred at 50° C. for 2 hours, then cooled gradually to 25° C. and stirred at 25° C. overnight. The product was isolated by vacuum filtration and dried at 40° C. for 16 hours to obtain STG dibenzoyl-D-tartarate crystalline form D1.

Example 4

STG Dibenzoyl-D-Tartarate Crystalline Form D1

STG base (350 mg) was dissolved in ethyl acetate (4.5 mL) at 25° C. (+)-Dibenzoyl-D-tartaric acid (98%, 323 mg, 1 eq) was then added and the resulting mixture was heated to 50° C. The mixture became a very thick slurry, therefore additional ethyl acetate (1.5 mL) was added. The resulting mixture was stirred at 50° C. for 2 hours, cooled gradually to 25° C. and stirred at 25° C. for 16 hours. The product was isolated by vacuum filtration and dried at 40° C. for 16 hours to produce STG dibenzoyl-D-tartarate crystalline form D1.

Example 5

STG Dibenzoyl-D-Tartarate Crystalline Form D2

STG base (350 mg) was partially dissolved in ethanol (3.5 mL) at 25° C. (+)-Dibenzoyl-D-tartaric acid (98%, 323 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG dibenzoyl-D-tartarate crystalline form D2.

Example 6

Mixture of STG Dibenzoyl-D-Tartarate Crystalline Forms D1 and D2

STG base (350 mg) was dissolved in isopropanol (3.5 mL) at 25° C. (+)-Di-benzoyl-D-tartaric acid (98%, 323 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain a mixture of sitagliptin dibenzoyl-D-tartarate crystalline forms D1 and D2.

Example 7

STG Fumarate Crystalline Form F1

STG base (350 mg) was dissolved in acetonitrile (2 mL) at 25° C. Fumaric acid (100 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain a mixture of sitagliptin fumarate crystalline form F1 and fumaric acid.

Example 8

STG Fumarate Crystalline Form F2

STG base (350 mg) was dissolved in ethyl acetate (4.5 mL) at 25° C. Fumaric acid (92 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG fumarate crystalline form F2.

Example 9

STG Malate Crystalline Form M1

STG base (350 mg) was dissolved in acetonitrile (2 mL) at 25° C. D-(+)-malic acid (115 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG D-malate crystalline form M1.

Example 10

STG Oxalate Crystalline Form O1

STG base (350 mg) was dissolved in ethanol (3.5 mL) at 25° C. Oxalic acid (108 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG oxalate crystalline form O1.

Example 11

STG Oxalate Crystalline Form O1

STG base (350 mg) was dissolved in isopropanol (3.5 mL) at 25° C. Oxalic acid (108 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG oxalate crystalline form O1.

Example 12

STG Quinate Crystalline Form Q1

STG base (350 mg) was dissolved in acetonitrile (2 mL) at 25° C. (1R,3R,4R,5R)-(−)-quinic acid (98%, 165 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG quinate crystalline form Q1.

Example 13

STG succinate crystalline form U1

STG base (350 mg) was dissolved in ethanol (3.5 mL) at 25° C. Succinic acid (101 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG succinate crystalline form U1, as shown in FIG. 7a.

Example 14

STG Succinate Crystalline Form U1

STG base (350 mg) was dissolved in acetonitrile (2 mL) at 25° C. Succinic acid (99%, 101 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to produce STG succinate crystalline form U1, as shown in FIG. 7b.

Example 15

STG Succinate Crystalline Form U1

Figure 7C:
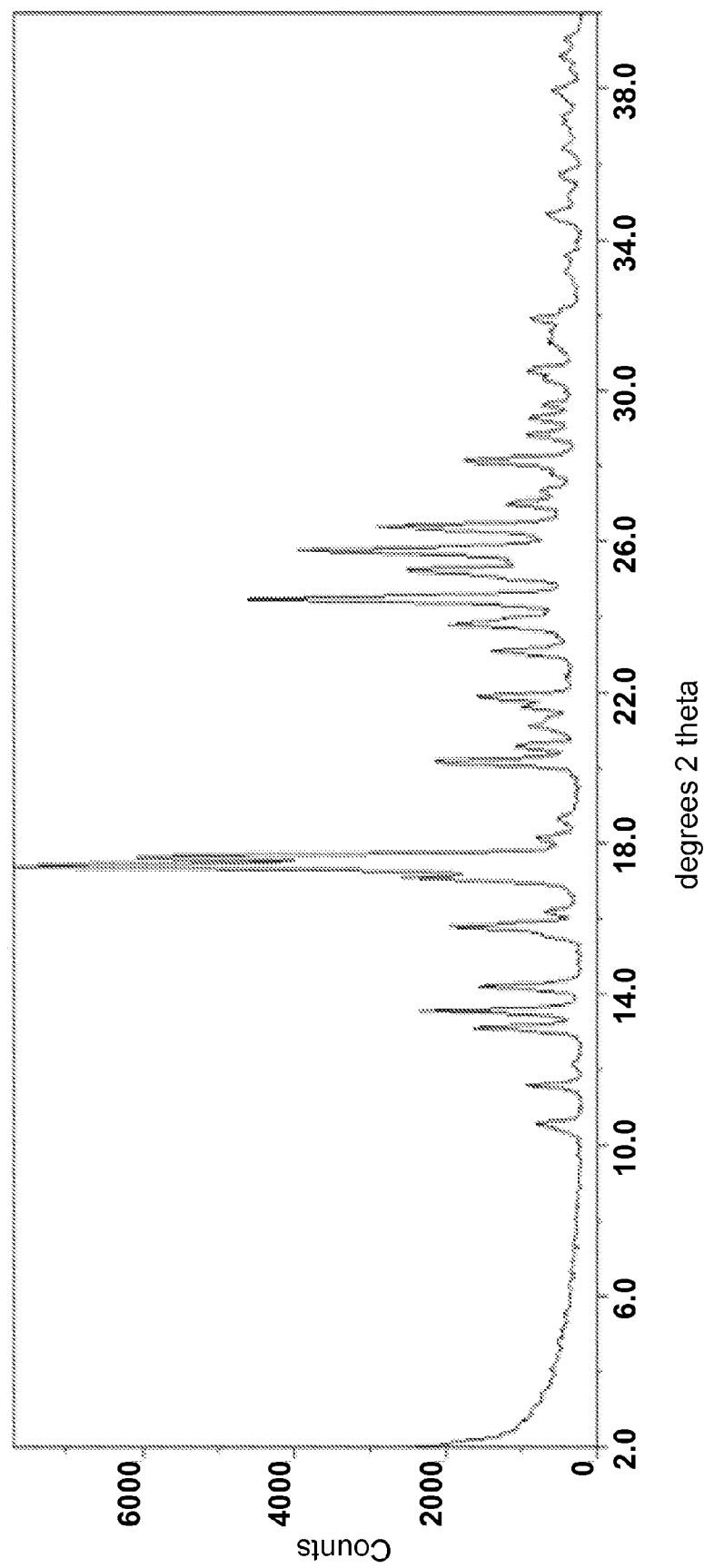
FIG. 7c shows a powder XRD pattern of crystalline Form U1 of Sitagliptin succinate.

STG base (350 mg) was dissolved in ethyl acetate (4.5 mL) at 25° C. succinic acid (99%, 101 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG succinate crystalline form U1, as shown in FIG. 7c.

Example 16

STG Oxalate Crystalline Form O1

STG base (350 mg) was dissolved in acetonitrile (2 mL) at 25° C. Oxalic acid (108 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG oxalate crystalline form O1.

Example 17

STG Oxalate Form O2

STG base (350 mg) was dissolved in ethyl acetate (4.5 mL) at 25° C. Oxalic acid (108 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG oxalate form O2.

Example 18

STG Sulfate Crystalline Form S2

STG base (350 mg) was dissolved in acetonitrile (2 mL) at 25° C. Sulfuric acid (95.6%, 24 mL, 0.5 eq) was then added and the mixture was heated to 50° C., stirred at 50° C. for 2 hours, then cooled gradually to 25° C. and stirred at 25° C. over weekend. The product was isolated by vacuum filtration and dried at 40° C. for 16 hours to obtain STG sulfate crystalline form S2.

Example 19

STG base (350 mg) was dissolved in ethyl acetate (4.5 mL) at 25° C. Sulfuric acid (95.6%, 24 µL, 0.5 eq) was then added and the mixture was heated to 50° C., stirred at 50° C. for 2 hours, then cooled gradually to 25° C. and stirred at 25° C. over weekend. The product was isolated by vacuum filtration and dried at 40° C. for 16 hours to obtain STG sulfate crystalline form S3.

Example 20

STG base (350 mg) was partially dissolved in ethanol (3.5 mL) at 25° C. Sulfuric acid (95.6%, 24 μL, 0.5 eq) was then added and the mixture was heated to 50° C., dissolved while heating, then stirred at 50° C. for 2 hours, cooled gradually to 25° C. and stirred at 25° C. over weekend. The product was isolated by vacuum filtration and dried at 40° C. for 16 hours to obtain STG sulfate crystalline form S4.

Example 21

STG Fumarate Crystalline Form F1

STG base (350 mg) was slurry in ethanol (3.5 mL) at 25° C. Fumaric acid (99.5 mg 1 eq) was then added and the resulting mixture was heated to 50° C., stirred at 50° C. for 2 hours, then cooled gradually to 25° C. and stirred at 25° C. for 16 hours.

The solution was clear; therefore, it was maintained at 4° C. for over a weekend. Then n-heptane (6 mL) was added, and the resulting mixture was stirred for 16 hours at 25° C. The product was isolated by vacuum filtration and dried at 40° C. for 16 hours to obtain STG quinate crystalline form F1.

Example 22

STG Fumarate—Mixture of Forms F2 and F1

STG base (350 mg) was partially dissolved in isopropanol (3.5 mL) at 25° C. Fumaric acid (100 mg, 1 eq) was then added and the resulting mixture was heated to 50° C., stirred at 50° C. for 2 hours, then cooled gradually to 25° C. and stirred at 25° C. for 16 hours.

Figure 3D:
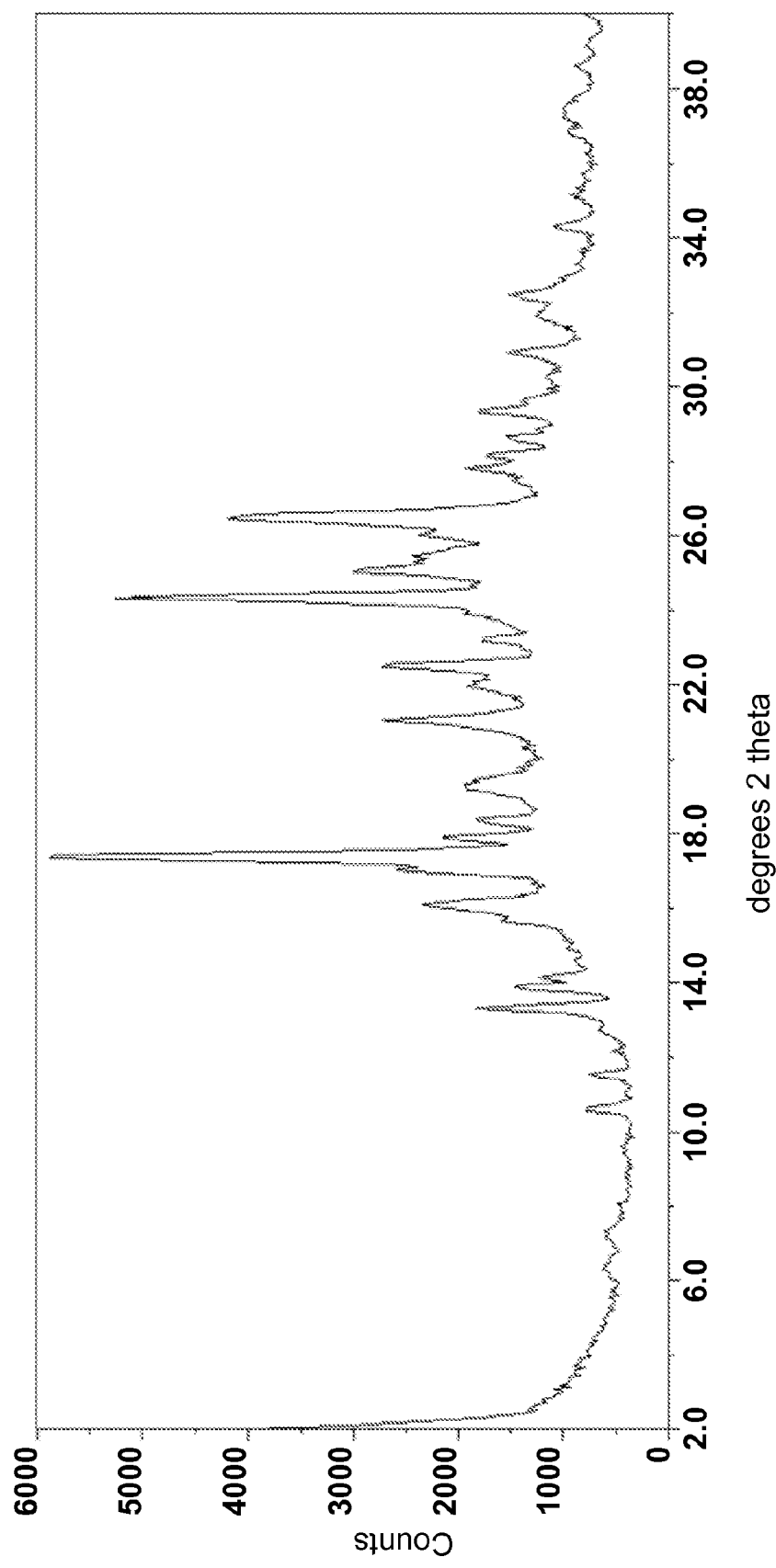
FIG. 3d shows a powder XRD pattern of crystalline Forms F2 and F1 of Sitagliptin fumarate.

The solution was clear; therefore it was maintained at 4° C. over a weekend. Then n-heptane (6 mL) was added, and the resulting mixture was stirred for 16 hours at 25° C. The product was isolated by vacuum filtration and dried at 40° C. for 16 hours to obtain sitagliptin fumarate polymorphic mixture of forms F2 and F1, as shown in FIG. 3*d*.

Example 23

STG Quinate Crystalline Form Q1

STG base (350 mg) was slurried in isopropanol (3.5 mL) at 25° C. (1R,3R,4R,5R)-(−)-Quinic acid (98%, 166 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG quinate crystalline form Q1.

Example 28

STG Malate Crystalline Form M2

STG base (350 mg) was dissolved in ethanol (3.5 mL) at 25° C. D-(+)-malic acid (115 mg, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG D-malate crystalline form M2.

Example 29

STG Acetate Crystalline Form E1

STG base (350 mg) was partially dissolved in ethyl acetate (3.5 mL) at 25° C. Acetic acid (50 μL, 1 eq) was then added and the resulting mixture was heated to 50° C., stirred at 50° C. for 2 hours, then cooled gradually to 25° C. and stirred at 25° C. for 16 hours. The product was isolated by vacuum filtration and dried at 40° C. for 16 hours to obtain STG acetate crystalline form E1.

Example 30

STG Mandelate Crystalline Form N1

STG base (350 mg) was dissolved in acetonitrile (2 mL) at 25° C. S-(+)-mandelic acid (130 mg, 1 eq) was then added and the resulting mixture was heated to 50° C., stirred at 50° C. for 2.75 hours, then cooled gradually to 25° C. and stirred at 25° C. for 16 hours. The product was isolated by vacuum filtration and dried at 40° C. for 16 hours to obtain STG mandelate crystalline form N1.

Example 31

STG Mandelate Crystalline Form N2

STG base (350 mg) was partially dissolved in ethyl acetate (3.5 mL) at 25° C. S-(+)-mandelic acid (134 mg, 1 eq) was then added and the resulting mixture was heated to 50° C., stirred at 50° C. for 2.75 hours, then cooled gradually to 25° C. and stirred at 25° C. for 16 hours. The product was isolated by vacuum filtration and dried at 40° C. for 16 hours to obtain STG S-mandelate crystalline form N2.

Example 32

STG S-Mandelate Crystalline Form N3

STG base (350 mg) was dissolved in ethanol (2.5 mL) at 25° C. S-(+)-mandelic acid (130 mg, 1 eq) was then added and the resulting mixture was heated to 50° C., stirred at 50° C. for 2.75 hours, then cooled gradually to 25° C. and stirred at 25° C. for 16 hours. The product was isolated by vacuum filtration and dried at 40° C. for 16 hours to obtain STG S-mandelate crystalline form N3.

Example 33

STG S-Mandelate Crystalline Form N4

STG base (350 mg) was dissolved in acetone (1.5 mL) at 25° C. S-(+)-mandelic acid (134 mg, 1 eq) was then added and the resulting mixture was heated to 40° C., stirred at 40° C. for 2.75 hours, then cooled gradually to 25° C. and stirred at 25° C. for 16 hours. The product was isolated by vacuum filtration and dried at 40° C. for 16 hours to obtain STG S-mandelate crystalline form N4.

Example 34

Amorphous STG Mandelate

STG base (350 mg) was slurried in methyl tert-butyl ether (3.5 mL) at 25° C. S-(+)-mandelic acid (132 mg, 1 eq) was then added and the resulting mixture was heated to 40° C., stirred at 40° C. for 2.75 hours, then cooled gradually to 25° C. and stirred at 25° C. for 16 hours. The product was isolated by vacuum filtration and dried at 40° C. for 16 hours to obtain amorphous STG mandelate.

Example 35

STG Lactate Crystalline Form L1

STG base (350 mg) was dissolved in acetonitrile (2 mL) at 25° C. DL-lactic acid (110 mL, 1 eq) was then added and the resulting mixture was heated to 50° C., stirred at 50° C. for 2.5 hours, then cooled gradually to 25° C. and stirred 25° C. for 16 hours. The product was isolated by vacuum filtration and dried at 40° C. for 16 hours to obtain STG lactate crystalline form L1.

Example 36

STG Lactate Crystalline Form L2

STG base (350 mg) was dissolved in acetone (1.5 mL) at 25° C. DL-Lactic acid (110 mL, 1 eq) was then added and the resulting mixture was heated to 50° C., stirred at 50° C. for 2.5 hours, then cooled gradually to 25° C. and stirred at 25° C. for 16 hours. The mixture formed was clear, therefore was put in a refrigerator at 4° C. for 16 hours. The mixture was still clear, therefore n-Heptane (5 mL) was added and the resulting mixture was stirred at 25° C. for 5 days. The product was isolated by vacuum filtration and dried at 40° C. for 16 hours to obtain STG lactate crystalline form L2, as shown in FIG. 12b.

Example 37

STG Lactate Crystalline Form L2

STG base (350 mg) was partially dissolved in ethyl acetate (3.5 mL) at 25° C. DL-lactic acid (110 mL, 1 eq) was then added and the resulting mixture was heated to 50° C., stirred at 50° C. for 2.5 hours, then cooled gradually to 25° C. and stirred at 25° C. for 16 hours. The product was isolated by vacuum filtration and dried at 40° C. for 16 hours to obtain STG lactate crystalline form L2, as shown in FIG. 12c.

Example 38

STG Lactate Crystalline Form L3

STG base (350 mg) was slurried in methyl tert-butyl ether (3.5 mL) at 25° C. DL-lactic acid (110 mL, 1 eq) was then added and the resulting mixture was heated to 40° C., stirred at 40° C. for 2.5 hours, then cooled gradually to 25° C. and stirred at 25° C. for 16 hours.

The product was isolated by vacuum filtration and dried at 40° C. for 16 hours to obtain STG lactate crystalline form L3. The material was retested by PXRD after 1 month storage and found to transform to form L1.

Example 39

STG Lactate Crystalline Form L4

STG base (350 mg) was dissolved in ethanol absolute (2.5 mL) at 25° C. DL-Lactic acid (110 mL, 1 eq) was then added and the resulting mixture was heated to 50° C., stirred at 50° C. for 2.5 hours, then cooled gradually to 25° C. and stirred at 25° C. for 16 hours. The mixture formed was clear, therefore was put in a refrigerator at 4° C. for 16 hours. The product was then isolated by vacuum filtration and dried at 40° C. for 16 hours to obtain STG lactate crystalline form L4.

Example 40

STG Maleate Crystalline Form A1

STG base (350 mg) was partially dissolved in ethanol absolute (3.5 mL) at 25° C. Maleic acid (102 mg, 1 eq) was then added and the resulting mixture was heated to 50° C., stirred at 50° C. for 2 hours, then cooled gradually to 25° C. and stirred at 25° C. for 16 hours. The mixture formed was clear, and therefore was put in a refrigerator at 4° C. for a week.

The mixture formed was still clear, therefore n-Heptane (3 mL) was added. The product was isolated by vacuum filtration and dried at 40° C. for 16 hours to obtain STG maleate crystalline form A1.

Example 41

STG S-Mandelate Crystalline Form N3

STG base (350 mg) was dissolved in tetrahydrofuran:water 1:1 (1 mL) at 25° C. S-(+)-mandelic acid (134 mg, 1 eq) was then added and the resulting mixture was heated to 50° C., stirred at 50° C. for 2.5 hours, then cooled gradually to 25° C. and stirred at 25° C. for 16 hours. The mixture formed was clear, therefore was put in a refrigerator at 4° C. for 16 hours. The mixture was still clear, therefore n-heptane (5 mL), was added and the resulting mixture was stirred at 25° C. for 5 days. The product was then isolated by vacuum filtration and dried at 40° C. for 16 hours to obtain STG S-mandelate crystalline form N3.

Example 42

STG Sulfate Crystalline Form S5

STG base (1.07 g) was dissolved in ethyl acetate (13 mL) at 25° C., and was heated to 40° C. to dissolve. The solution was then cooled to 25° C. Sulfuric acid (95.6%, 0.133 mL, 0.5 eq) was then added and the resulting mixture was heated to 50° C., stirred at 50° C. for 2.5 hours, then cooled gradually to 25° C. and stirred at 25° C. for 19 hours. The product was isolated by vacuum filtration and dried at 40° C. for 16 hours to obtain STG sulfate crystalline form S5 (0.92 g, 69% yield).

Example 43

STG Sulfate Crystalline Form S5

STG base (4 g) was dissolved in acetonitrile (24 mL) at 25° C. Sulfuric acid (95.6%, 0.54 mL, 1 eq) was then added and the resulting mixture was heated to 50° C., stirred at 50° C. for 1.5 hours, then cooled gradually to 25° C. and stirred at 25° C. over night. The product was isolated by vacuum filtration and dried at 40° C. over night to obtain 3.61 gr STG sulfate crystalline form S5.

Example 44

STG Sulfate Form S6

STG base (5 g) was dissolved in ethyl acetate (65 mL) at 25° C., heated to 40° C. to dissolution, and then cooled to 25°

C. Sulfuric acid (95.6%, 0.34 mL, 0.5 eq) was then added and the resulting mixtures heated to 50° C., stirred at 50° C. for 3 hours, and then cooled gradually to 25° C. and stirred at 25° C. for 1.5 hours. The product was isolated by vacuum filtration and dried at 40° C. over night to obtain STG sulfate form S6 (5.23 g, 85% yield).

Example 45

STG (L)-Malate Crystalline Form I1

STG base (5 g) was dissolved in acetonitrile (28.5 mL) at 25° C. (L)-Malic acid (1.65 g, 1 eq) was then added and the resulting mixture was heated to 50° C. After stirring at 50° C. for 3 hours it was cooled gradually to 25° C. and stirred overnight. The mixture formed was very viscous. It was cooled in an ice bath for 1 hour and then heated back to 25° C. n-Heptane (7 mL) was added and the resulting mixture was stirred at 25° C. for 2 hours. The product was isolated by vacuum filtration and dried at 40° C. over night to obtain STG (L)-malate crystalline form I1 (3.01 gr).

Example 46

STG R-(−)-Mandelate Crystalline Form N5

STG base (5 g) was dissolved in acetonitrile (28.5 mL) at 25° C. (R)-Mandelic acid (1.87 g, 1 eq) was then added and the resulting mixture was heated to 50° C. and stirred for 3 hours, then cooled gradually to 25° C. and stirred overnight. The product was isolated by vacuum filtration and dried at 40° C. overnight to obtain Sitagliptin R-(−)-mandelate crystalline form N5 (6.50 gr, 95% yield)

Example 47

STG R-(−)-Mandelate Crystalline Form N6

STG base (5 g) was dissolved in ethyl acetate (50 mL) at 25° C. and heated to 40° C. to dissolve, then cooled back to room temperature. (R)-Mandelic acid (1.87 g, 1 eq) was then added and the resulting mixture was heated to 50° C. and stirred for 3 hours, then cooled gradually to 25° C. and stirred overnight. The product was isolated by vacuum filtration and dried at 40° C. overnight to obtain Sitagliptin R-(−)-mandelate crystalline form N6 (6.62 gr, 97% yield)

Example 48

STG R-(−)-Mandelate Crystalline Form N5

STG base (5 g) was dissolved in absolute ethanol (35 mL) at 25° C. and heated to 40° C. to dissolve, then cooled to RT. (R)-Mandelic acid (1.87 g, 1 eq) was then added and the absolute mixture was heated to 50° C. and stirred for 2.5 hours, then cooled gradually to 25° C. and stirred overnight. The product was isolated by vacuum filtration and dried at 40° C. for 70 hours to obtain Sitagliptin R-(−)-mandelate crystalline form N5 (6 gr, 88% yield).

Example 49

STG R-(−)-Mandelate Crystalline Form N5

STG base (5 g) was dissolved in acetone (21.5 mL) at 25° C. (R)-Mandelic acid (1.87 g, 1 eq) was then added and the resulting mixture was heated to 40° C. and stirred for 2.5 hours, then cooled gradually to 25° C. and stirred overnight. The product was isolated by vacuum filtration and dried at 40° C. for 70 hours to obtain Sitagliptin R-(−)-mandelate crystalline form N5 (4.69 g, 69% yield).

Example 50

Amorphous STG Orotate

Figure 13A:
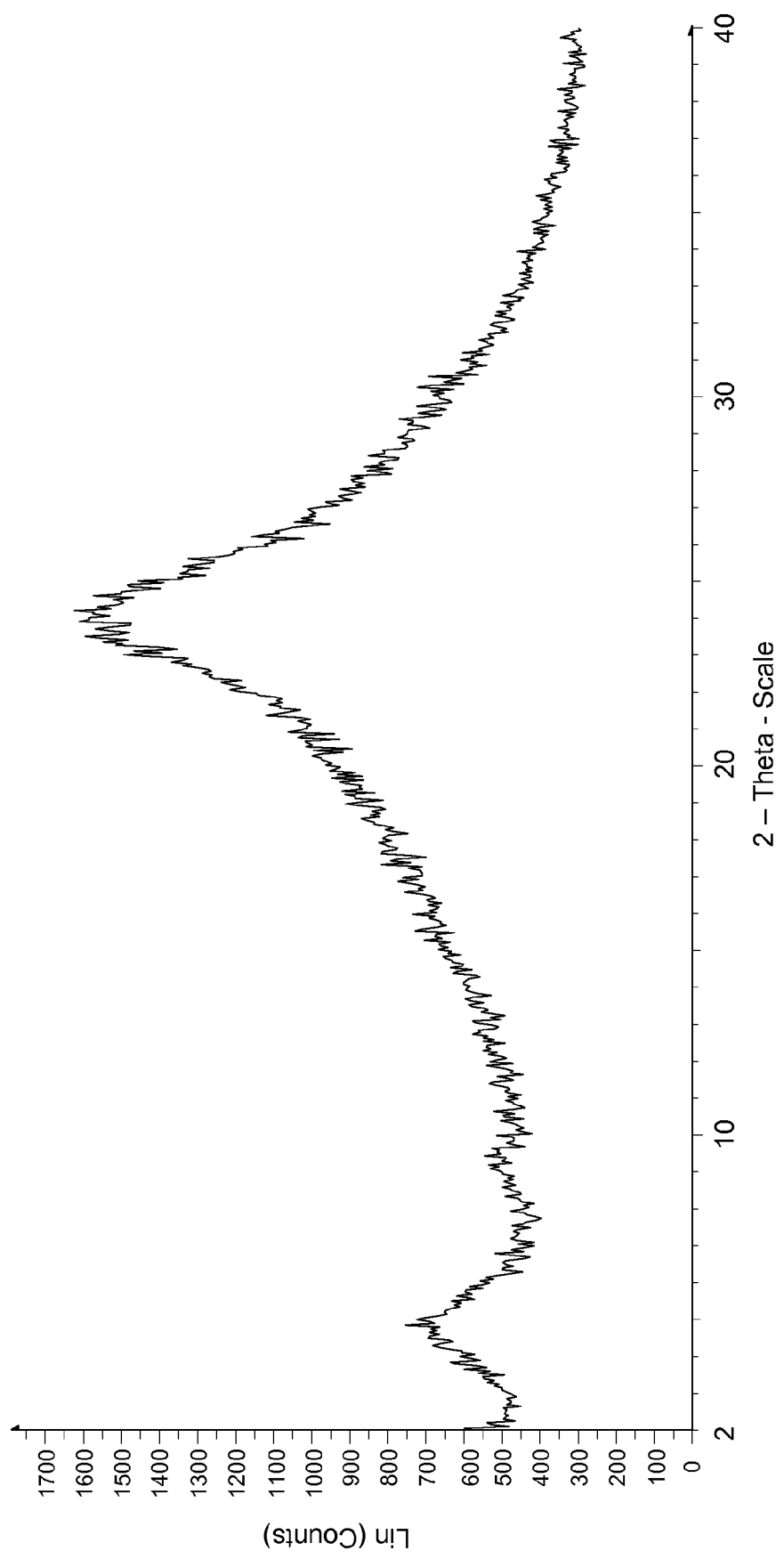
FIG. 13a shows a powder XRD pattern of amorphous Sitagliptin orotate, before drying.
Figure 13B:
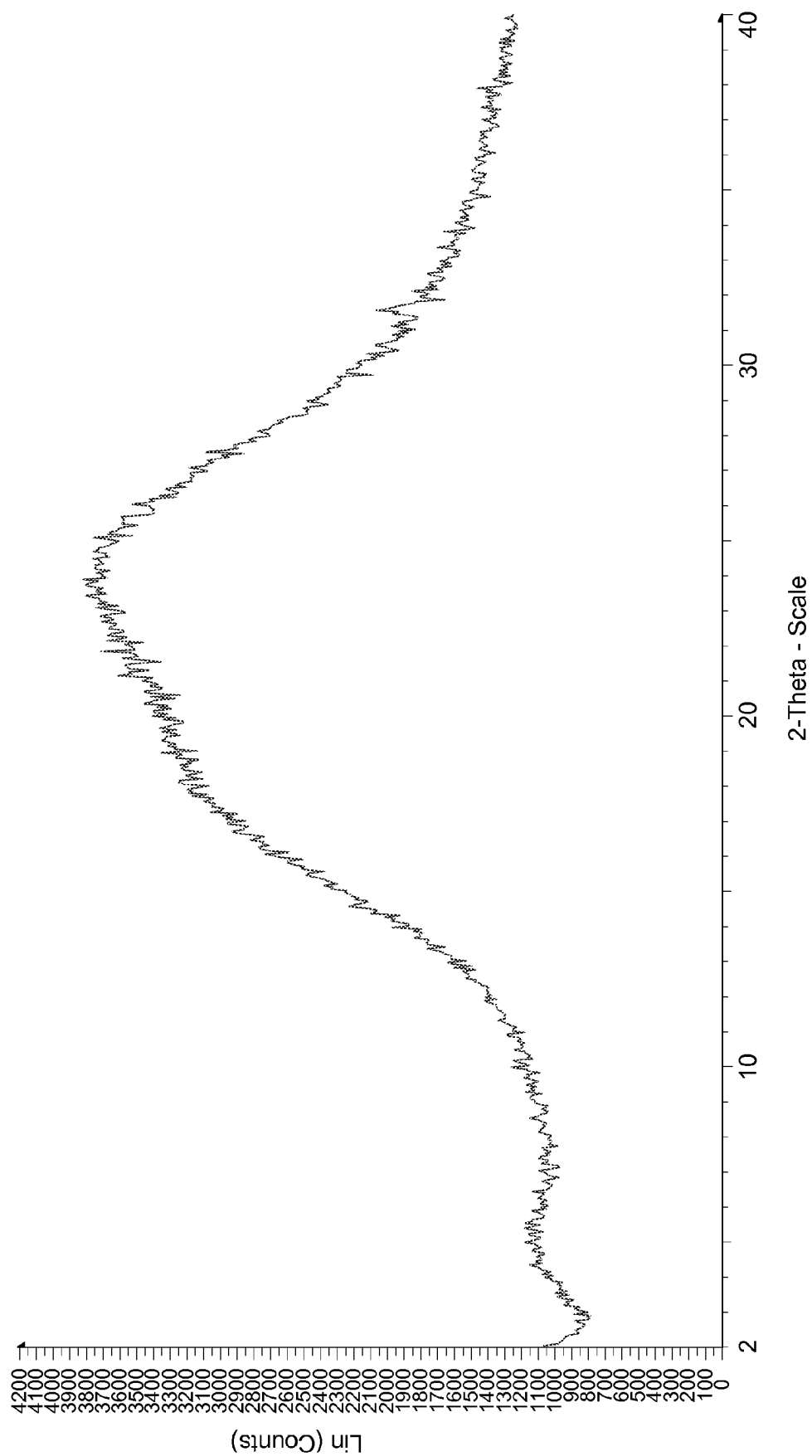
FIG. 13b shows a powder XRD pattern of amorphous Sitagliptin orotate, after drying.

STG base (0.5 g) was dissolved in acetonitrile (6.25 mL) at 25° C. Orotic acid (0.19 g, 1 eq) was then added and the resulting mixture was heated to 75° C., and stirred for 45 minutes, then cooled gradually to 25° C. and stirred overnight. The product was isolated by vacuum filtration to obtain amorphous Sitagliptin orotate as depicted in FIG. 13a. It was then dried at 40° C. over night to obtain amorphous STG orotate, the powder X-ray diffractogram of which is depicted in FIG. 13b (0.44 g, 64% yield).

Example 51

Amorphous STG Orotate

Figure 13C:
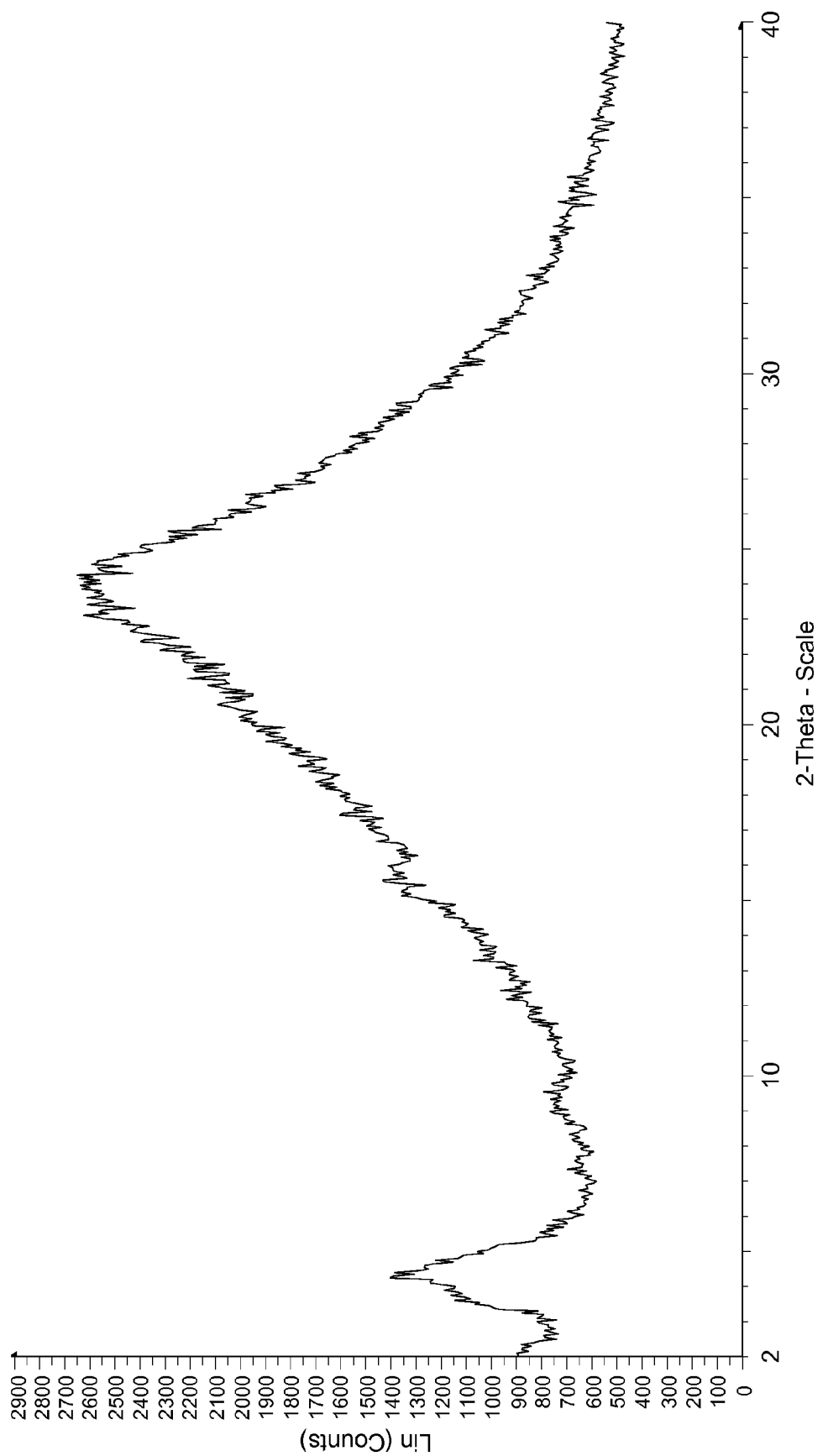
FIG. 13c shows a powder XRD pattern of amorphous Sitagliptin orotate, before drying.
Figure 13D:
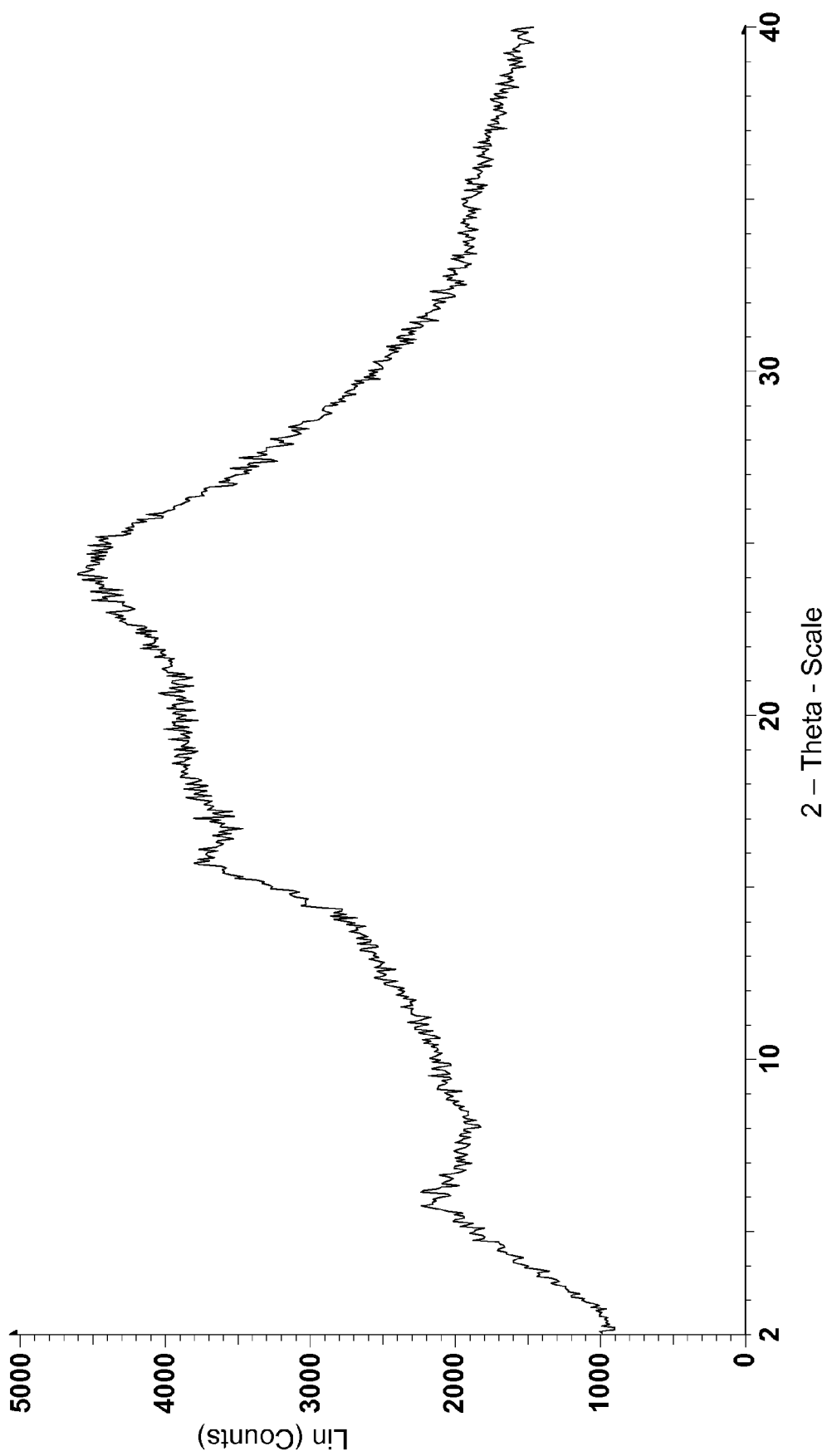
FIG. 13d shows a powder XRD pattern of amorphous Sitagliptin orotate, after drying.

STG base (5 g) was dissolved in acetonitrile (60 mL) at 25° C. Orotic acid (1.9 g, 1 eq) was then added and the resulting mixture was heated to 75° C., and stirred for 45 minutes, then cooled gradually to 25° C. and stirred over night. The product was isolated by vacuum filtration to obtain amorphous Sitagliptin orotate (powder XRD is depicted in FIG. 13c. It was then dried at 40° C. over night to obtain amorphous STG orotate (6.85 g, 99% yield). (powder XRD is depicted in FIG. 13d)

Example 52

Siltagliptin Sulfate Form S7

STG base (5 gr) was added into isopropanol (85 ml). The obtained mixture was heated to dissolution. The solution was cooled to room temperature and sulfuric acid 96.5% (0.6 gr, 0.5 eq) was added, then the slurry was stirred for 4 hours. The product was isolated by vacuum filtration; the cake was washed with hexane (10 ml), and dried at 40° C. in vacuum oven overnight to obtain Form S7 as shown in FIG. 1g; 5.76 gr (93% yield). The TGA termogram is shown in FIG. 1r.

Example 53

Siltagliptin Sulfate Form S7

Figure 1S:
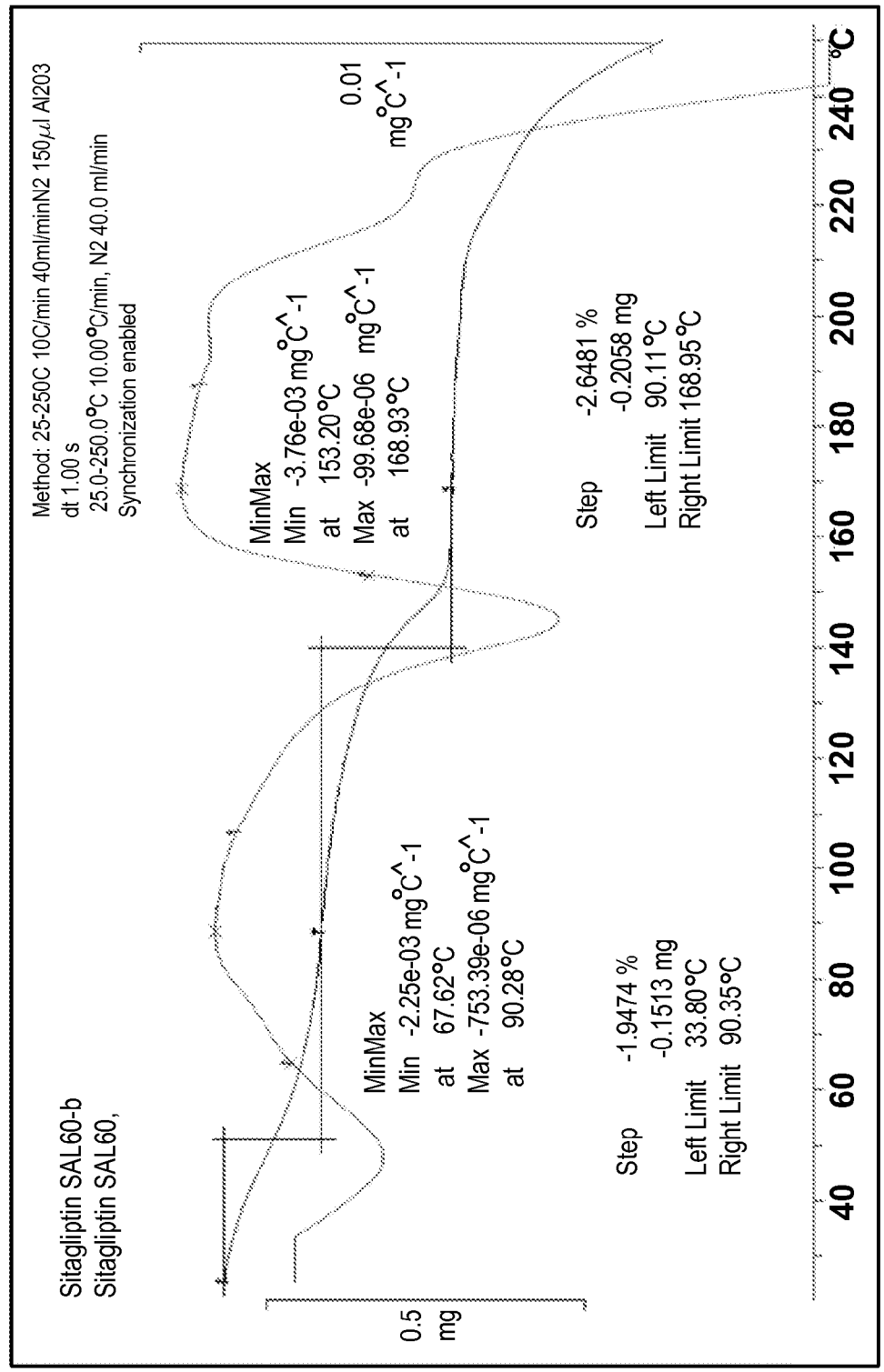
FIG. 1s shows a TGA termogram of Sitagliptin sulfate isopropanol solvate Form S7.

To STG base (5 gr), isopropanol (70 ml) was added, heated to dissolution, and cooled to room temperature. Sulfuric acid 96.5% (0.6 gr, 0.5 eq) was added and the solution became slurry and was stirred over night. The product was isolated by vacuum filtration; the cake was washed with isopropanol (20 ml), and dried at 40° C. in vacuum oven over night to obtain Form S7 as shown in FIG. 1h; 5.51 gr. The TGA termogram is shown in FIG. 1s.

Example 54

Siltagliptin Sulfate Form S8

A sample of form S2 was heated by DSC to 180° C. to obtain form S8 of Sitagliptin sulfate. X-ray diffractogram of Sitagliptin sulfate form S8 is presented in FIG. 1k. DSC thermogram of the heating process is presented in FIG. 1l.

DSC analysis was performed on Q 1000 MDSC TA instruments with heating rate of 10° C./min, under nitrogen flow of 50 ml/min. Hermetic aluminum, closed pan was used, sample mass was about 8-10 mg.
Instrument Type: DSC-TA Q1000

Samples after being heated in hermetic crucible under experimental conditions described in DSC experiment are applied directly on silicon plate holder and mixed with small amount of Si powder. The X-ray powder diffraction pattern was measured with Philips X'Pert PRO X-ray powder diffractometer, equipped with Cu irradiation source=1.54060 Å (Ångström), X'Celerator (2.022° 2theta) detector. Scanning parameters: angle range: 3-40 deg., step size 0.0167, time per step 39 s, continuous scan. The accuracy of peak positions was defined as ±0.2 degrees due to experimental differences like instrumentations and sample preparations.

Example 55

Siltagliptin Acetate Form E1

To STG base (5 gr), ethyl acetate (35 ml) was added, heated to dissolution and cooled to room temperature. Then Acetic acid (0.703 ml, 1 eq) was added and the reaction mixture was heated to 50° C. After 0.5 hour at 50° C., precipitations were observed and the mixture was stirred for 2 hours. Then the reaction mixture was cooled to room temperature and stirred for 1 hour. The product was isolated by vacuum filtration, the cake was washed with ethyl acetate, and dried at 40° C. in vacuum oven over night to obtain Form E1; 4.19 gr (73% yield).

Example 56

Transformation of Form S7 to Form S1

About 150 mg of Sitagliptin sulfate form S7 were put in an open Petrii dish and kept at 100+5% RH (relative humidity) and room temperature for 12 days. It was then analyzed by powder XRD. The resulted form S1 is presented in FIG. 1*q*.

For XRD measurement samples are mixed with small amount of Si powder and applied directly on silicon plate holder. The X-ray powder diffraction pattern was measured with Philips X'Pert PRO X-ray powder diffractometer, equipped with Cu irradiation source=1.54060 Å (Ångström), X'Celerator (2.022° 2Q) detector. Scanning parameters: angle range: 3-40 deg., step size 0.0167, time per step 39 s, continuous scan.

What is claimed is:

1. A crystalline form of Sitagliptin sulfate, designated Form S2, characterized by data selected from: a powder X-ray diffraction pattern with peaks at 9.3°, 9.7°, 15.2°, 15.6° and 25.4°±0.2° 2θ; a powder X-ray diffraction pattern as shown in FIG. 1*b*; a solid-state $^{13}$C NMR spectrum with signals at 119.2, 150.3 and 170.6±0.2 ppm; a solid-state $^{13}$C NMR spectrum having chemical shifts differences between the signal exhibiting the lowest chemical shift and another in the chemical shift range of 100 to 180 ppm of 13.7, 44.8 and 65.1±0.1 ppm; a $^{13}$C NMR spectrum as depicted in FIG. 1*m* and FIG. 1*n*; and combinations thereof.

2. A pharmaceutical composition comprising a crystalline form of claim 1, and at least one pharmaceutically acceptable excipient.

3. A crystalline form of Sitagliptin sulfate isopropanol solvate, designated Form S7, characterized by data selected from: a powder X-ray diffraction pattern with peaks at 5.2°, 15.6°, 16.6°, 18.7° and 21.1°±0.2° 2θ; a powder X-ray diffraction pattern as shown in FIG. 1*g*; a solid-state $^{13}$C NMR spectrum with signals at 120.4, 149.1 and 171.2±0.2 ppm; a solid-state $^{13}$C NMR spectrum having chemical shifts differences between the signal exhibiting the lowest chemical shift and another in the chemical shift range of 100 to 180 ppm of 15.1, 43.8 and 65.9±0.1 ppm; and a $^{13}$C NMR spectrum as depicted in FIG. 1*i* and FIG. 1*j*; and combinations thereof.

4. A pharmaceutical composition comprising a crystalline form of claim 3, and at least one pharmaceutically acceptable excipient.

5. A crystalline form of Sitagliptin sulfate, designated Form S6, characterized by a powder X-ray diffraction pattern as shown in FIG. 1*f*.

6. A pharmaceutical composition comprising a crystalline form of claim 5, and at least one pharmaceutically acceptable excipient.

7. A crystalline form of Sitagliptin sulfate isopropanol solvate characterized by data selected from: a powder X-ray diffraction pattern with peaks at 5.2°, 15.6°, 16.6°, 17.0°, 17.1°, 18.7° and 21.1°±0.2° 2θ; a powder X-ray diffraction pattern as shown in FIG. 1*g*; a solid-state $^{13}$C NMR spectrum with signals at 120.4, 149.1 and 171.2±0.2 ppm; a solid-state $^{13}$C NMR spectrum having chemical shifts differences between the signal exhibiting the lowest chemical shift and another in the chemical shift range of 100 to 180 ppm of 15.1, 43.8 and 65.9±0.1 ppm; and a $^{13}$C NMR spectrum as depicted in FIG. 1*i* and FIG. 1*j*; and combinations thereof.

8. A pharmaceutical composition comprising the crystalline form of claim 7, and at least one pharmaceutically acceptable excipient.

9. A crystalline form of Sitagliptin sulfate designated Form S1, characterized by data selected from: a powder X-ray diffraction pattern with peaks at 11.8°, 13.7°, 14.4°, 17.0° and 17.5°±0.2° 2θ; a powder X-ray diffraction pattern as shown in FIG. 1*a*; and combinations thereof.

10. A pharmaceutical composition comprising a crystalline form of claim 9, and at least one pharmaceutically acceptable excipient.

* * * * *